(12) United States Patent
Kato et al.

(10) Patent No.: US 9,487,488 B2
(45) Date of Patent: Nov. 8, 2016

(54) SULFONAMIDE COMPOUND

(71) Applicant: MITSUBISHI TANABE PHARMA CORPORATION, Osaka-shi, Osaka (JP)

(72) Inventors: Taku Kato, Machida (JP); Toshiaki Sakamoto, Saitama (JP); Akira Kubo, Tokyo (JP); Daisuke Sawamoto, Saitama (JP)

(73) Assignee: MITSUBISHI TANABE PHARMA CORPORATION, Osaka-shi (JP)

( * ) Notice: Subject to any disclaimer, the term of this patent is extended or adjusted under 35 U.S.C. 154(b) by 0 days.

(21) Appl. No.: 14/428,267

(22) PCT Filed: Sep. 13, 2013

(86) PCT No.: PCT/JP2013/074812
§ 371 (c)(1),
(2) Date: Mar. 13, 2015

(87) PCT Pub. No.: WO2014/042238
PCT Pub. Date: Mar. 20, 2014

(65) Prior Publication Data
US 2015/0307454 A1    Oct. 29, 2015

(30) Foreign Application Priority Data

Sep. 14, 2012   (JP) ................. 2012-203126
Sep. 14, 2012   (JP) ................. 2012/203128

(51) Int. Cl.
| | | |
|---|---|---|
| C07D 401/12 | (2006.01) |
| C07D 413/12 | (2006.01) |
| C07D 217/22 | (2006.01) |
| A61K 31/472 | (2006.01) |
| A61K 31/44 | (2006.01) |
| C07D 401/14 | (2006.01) |
| C07D 413/14 | (2006.01) |

(52) U.S. Cl.
CPC ........... C07D 217/22 (2013.01); C07D 401/12 (2013.01); C07D 401/14 (2013.01); C07D 413/12 (2013.01); C07D 413/14 (2013.01)

(58) Field of Classification Search
None
See application file for complete search history.

(56) References Cited

U.S. PATENT DOCUMENTS 8,987,445 B2    3/2015   Tsuzuki et al.

FOREIGN PATENT DOCUMENTS

WO    WO 2009/012430 A1    1/2009
WO    WO 2010/010435 A2    1/2010

(Continued)

OTHER PUBLICATIONS

International Preliminary Report on Patentability and Written Opinion for International Application No. PCT/JP2012/O57412, mailed Sep. 26, 2013, from the International Bureau of WIPO.

(Continued)

*Primary Examiner* — Zinna Northington Davis
(74) *Attorney, Agent, or Firm* — Finnegan, Henderson, Farabow, Garrett & Dunner, L.L.P.

(57) ABSTRACT

The present invention provides novel sulfonamide compounds having TRPM8 antagonistic activity which are useful as medicaments. Specifically, the present invention provides a sulfonamide compound of the formula (I):

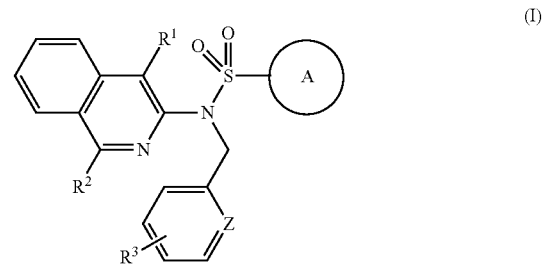

wherein Ring A is the following formula (i), (ii), or (ix):

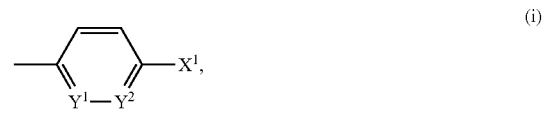

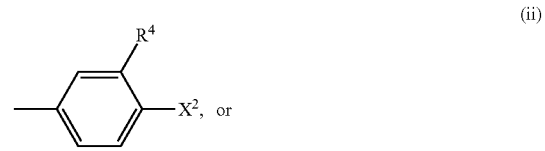

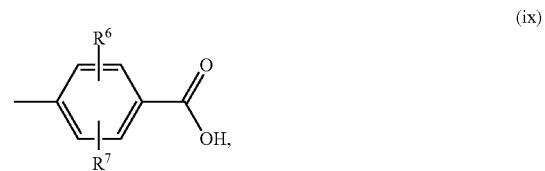

$R^4$ is optionally substituted alkyl,
$X^1$ and $X^2$ are each independently tetrazolyl, tetrazolinonyl, optionally substituted triazolyl, triazolinonyl, oxadiazolonyl, optionally substituted alkanoylaminomethyl, or optionally substituted alkylsulfonylaminomethyl, or
$R^4$ and $X^2$ combine with each other at their terminals together with the adjacent benzene to form indazolinonyl or benzoisoxazolonyl, and
the other symbols are the same as described in the specification,
or a pharmaceutically acceptable salt thereof.

17 Claims, No Drawings

(56) References Cited

FOREIGN PATENT DOCUMENTS

| WO | WO 2010/125831 A1 | 11/2010 |
|----|-------------------|---------|
| WO | WO 2012/042915 A1 | 4/2012  |
| WO | WO 2012/078994 A1 | 6/2012  |
| WO | WO 2012/124825 A1 | 9/2012  |
| WO | WO 2013/074812 A1 | 3/2015  |

OTHER PUBLICATIONS

Edited by Wolff, Manfred E., "Burger's Medicinal Chemistry and Drug Discovery, Fifth Ed., vol. 1: Principles and Practice," John Wiley & Sons (1995), pp. 975-977.

Edited by Banker, Gilbert S. et al., "Modern Pharmaceutics, 3rd Edition, Revised and Expanded," Marcel Dekker, Inc., New York (1996), pp. 451 and 596.

Srimali, S., et al., "Proton-catalyzed Rearrangement of Sulfonamides to Sulfones, I. Conversion of Substituted Arylquinolylamine Sulfonamide into the Isomeric Substituted Diarylsulfone," Revue Roumaine de Chimie, vol. 23, No. 4, pp. 613-616 (1978).

Yasuyuki Tsuzuki et al., "Sulfonamide Compounds Having TRPM8 Antagonistic Activity", U.S. Appl. No. 14/620,360, filed Feb. 12, 2015.

David D. McKemy et al., "Identification of a cold receptor reveals a role for TRP channels in thermosensation", Nature, vol. 416, No. 6876, pp. 52-58 (2002).

Junji Abe et al., "Ca2+_dependant PKC activation mediates mentol-induced desensitization of transient receptor potential M8", Neuroscience, vol. 397, No. 1-2, pp. 140-144 (2006).

Louis S. Premkumar et al., "Downregulation of Transient Receptor Potential Melastatin 8 by Protein Kinase C-Mediated Dephosphorylation", The Journal of Neuroscience, 2005, vol. 25, No. 49, pp. 11322-11329 (2005).

Hong Xing et al., "TRPM8 Mechanism of Cold Allodynia after Chronic Nerve Injury", The Journal of Neuroscience, vol. 27, No. 50, pp. 13680-13690 (2007).

Punam Gauchan et al., "Involvement of increased expression of transient receptor potential melastatin 8 in oxaliplatin-induced cold allodynia in mice", Neuroscience Letters, vol. 458, No. 2, pp. 93-95 (2009).

International Search Report from the Japanese Patent Office for International Application No. PCT/JP2013/074812 mailed Nov. 12, 2013.

International Preliminary Report on Patentability from The International Bureau of WIPO for International Application No. PCT/JP2013/074812 mailed Mar. 26, 2015.

Written Opinion from The International Bureau of WIPO for International Application No. PCT/JP2013/074812 mailed Nov. 12, 2013.

Extended European Search Report for corresponding European Application No. 13837919.3 dated Jan. 26, 2016.

SULFONAMIDE COMPOUND

TECHNICAL FIELD

The present invention relates to novel sulfonamide compounds having TRPM8 antagonistic activity which are useful as medicaments.

BACKGROUND ART

TRP (transient receptor potential) channels are non-selective cation channels that are activated by a variety of physical (e.g., temperature, osmolarity, or mechanical) and chemical stimuli. A subset of the TRP channel superfamily is thermoresponsive, each channel being activated over a discrete temperature range, cumulatively spanning from noxious cold to noxious heat. TRPM8 belongs to the melastatin subgroup of the TRP channel superfamily TRPM8 is sensitive to cold temperature and menthol, and therefore also called as cold menthol receptor-1 (CMR-1). TRPM8 is known to be stimulated by cold temperatures (8 to 28° C.) as well as by chemical substances such as menthol and icilin (e.g., Nonpatent Document 1).

TRPM8 is mainly located on primary nociceptive neurons (A-δ and C-fibers) and is also modulated by inflammation-mediated second messengers (e.g., Nonpatent Documents 2 and 3). The location of TRPM8 on both A-δ and C-fibers may provide a basis for abnormal cold sensitivity in pathologic conditions wherein these neurons are altered, resulting in pain, often of a burning nature. TRPM8 immunostaining in primary afferents was increased in rats with chronic constriction injury (CCI), a neuropathic pain model manifesting cold allodynia in hindlimbs (e.g., Nonpatent Document 4). The expression of TRPM8 in primary afferents was increased in oxaliplatin-induced cold allodynia model in mice (e.g., Nonpatent Document 5).

Cold intolerance and paradoxical burning sensations induced by chemical substances or thermal cooling are closely parallel symptoms seen in a wide range of clinical disorders and thus provide a strong rationale for the development on TRPM8 modulators as novel antihyperalgesic or antiallodynic agents. TRPM8 is also known to be expressed in the brain, lung, bladder, gastrointestinal tract, blood vessels, prostate and immune cells, thereby providing the possibility for therapeutic modulation in a variety of maladies.

N-Benzothiophenylsulfonamide compounds (e.g., Patent Document 1), N-benzimidazolylsulfonamide compounds (e.g., Patent Document 2), N-phenylsulfonamide compounds, and N-pyridylsulfonamide compounds (e.g., Patent Document 3), etc. have been known as a TRPM8 modulator. However, it has never been reported that a compound having a structure in which isoquinolyl binds to a sulfonylamino group has a TRPM8 antagonistic activity.

BACKGROUND ART DOCUMENTS

Patent Documents

[Patent Document 1] WO 2009/012430 pamphlet
[Patent Document 2] WO 2010/144680 pamphlet
[Patent Document 3] WO 2010/125831 pamphlet

Nonpatent Documents

[Nonpatent Document 1] D. D. McKemy, and other two persons, "Identification of a cold receptor reveals a general role for TRP channels in thermosensation", Nature, 2002, Vol. 416, No. 6876, p. 52-58

[Nonpatent Document 2] J. Abe, and other four persons, "$Ca^{2+}$-dependent PKC activation mediates menthol-induced desensitization of transient receptor potential M8", Neuroscience Letters, 2006, Vol. 397, No. 1-2, p. 140-144

[Nonpatent Document 3] L. S. Premkumar, and other four persons, "Downregulation of Transient Receptor Potential Melastatin 8 by Protein Kinase C-Mediated Dephosphorylation", the Journal of Neuroscience, 2005, Vol. 25, No. 49, p. 11322-11329

[Nonpatent Document 4] H. Xing, and other four persons, "TRPM8 Mechanism of Cold Allodynia after Chronic Nerve Injury", the Journal of Neuroscience, 2007, Vol. 27, No. 50, p. 13680-13690

[Nonpatent Document 5] P. Gauchan, and other three persons, "Involvement of increased expression of transient receptor potential melastatin 8 in oxaliplatin-induced cold allodynia in mice", Neuroscience Letters, 2009, Vol. 458, No. 2, p. 93-95

SUMMARY OF THE INVENTION

Problems to be Solved by the Invention

An object of the present invention is to provide novel sulfonamide compounds having TRPM8 antagonistic activity which are useful as medicaments.

Means for Solving the Problems

[1] The present invention relates to a compound of the formula (I):

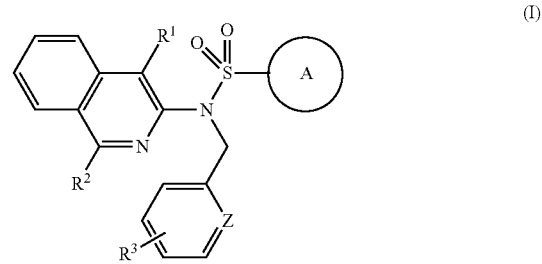

wherein
$R^1$ is optionally substituted alkyl or optionally substituted cycloalkyl,
$R^2$ is a hydrogen atom or optionally substituted cycloalkyl,
$R^3$ is optionally substituted alkyl or optionally substituted alkoxy,
Z is CH or N,
Ring A is the following formula (i), (ii), or (ix):

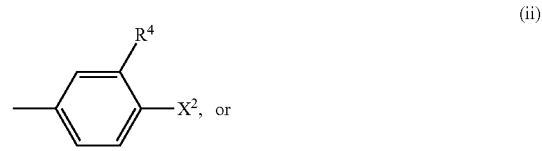

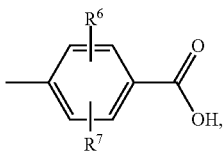

(ix)

R⁴ is optionally substituted alkyl,

R⁶ is optionally substituted alkyl, optionally substituted cycloalkyl, optionally substituted alkoxy, optionally substituted alkylamino, optionally substituted dialkylamino, an optionally substituted monocyclic nitrogen-containing non-aromatic heterocyclic group, optionally substituted phenyl, or halogen, R⁷ is a hydrogen atom, optionally substituted alkyl, or halogen, X¹ and X² are each independently tetrazolyl, tetrazolinonyl, optionally substituted triazolyl, triazolinonyl, oxadiazolonyl, optionally substituted alkanoylaminomethyl, or optionally substituted alkylsulfonylaminomethyl, or R⁴ and X² combine with each other at their terminals together with the adjacent benzene to form indazolinonyl or benzoisoxazolonyl, and Y¹ and Y² are both CH, or one of Y¹ and Y² is CH, and the other is N, or a pharmaceutically acceptable salt thereof.

Also, the present invention relates to a method for treating or preventing various diseases involving TRPM8 (e.g., a chronic pain such as neuropathic pain), which comprises administering an effective amount of the compound of the above formula (I) (hereinafter also referred to as compound (I)) or a pharmaceutically acceptable salt thereof to a subject.

In addition, the present invention relates to a pharmaceutical composition comprising the above compound (I) or a pharmaceutically acceptable salt thereof as an active ingredient, and use of the above compound (I) or a pharmaceutically acceptable salt thereof in the manufacture of the pharmaceutical composition.

Further, the present invention relates to a process for preparing the above compound (I) or a pharmaceutically acceptable salt thereof.

Effects of the Invention

The compound of the formula (I) shows an excellent inhibitory effect on behavior induced by TRPM8 agonists as well as an excellent TRPM8 antagonistic activity. Accordingly, the compound of the formula (I) is useful as a medicament for prevention or treatment of various diseases involving TRPM8 (e.g., a chronic pain such as neuropathic pain (preferably, neuropathic pain caused by cold allodynia or diabetic neuropathy)).

Also, the compound of the formula (I) or a pharmaceutically acceptable salt thereof shows preferable properties as an active ingredient of a medicament (e.g., excellent pharmacokinetic properties and excellent safety).

EMBODIMENTS TO CARRY OUT THE INVENTION

Each definition of each term used herein is as follows.

The term "alkyl" refers to straight or branched-chain saturated hydrocarbon chain with 1 to 6 carbons, and includes methyl, ethyl, propyl, isopropyl, butyl, t-butyl, isobutyl, and various branched-chain isomers thereof, preferably straight or branched-chain saturated hydrocarbon chain with 1 to 4 carbons.

The term "alkenyl" refers to straight or branched-chain unsaturated hydrocarbon chain with 2 to 6 carbons containing one carbon-carbon double bond, and includes vinyl, propenyl, butenyl, and various branched-chain isomers thereof, preferably straight or branched-chain unsaturated hydrocarbon chain with 2 to 4 carbons.

The term "alkylene" refers to straight or branched-chain divalent saturated hydrocarbon chain with 1 to 6 carbons, and includes methylene, ethylene, propylene, trimethylene, butylene, tetramethylene, pentamethylene, 1,1,2,2-tetramethylethylene, and various branched-chain isomers thereof, preferably straight or branched-chain divalent saturated hydrocarbon chain with 1 to 4 carbons.

The term "cycloalkyl" refers to an alicyclic saturated hydrocarbon group with 3 to 7 carbons, and includes cyclopropyl, cyclobutyl, cyclopentyl or cyclohexyl, preferably an alicyclic saturated hydrocarbon group with 3 to 6 carbons.

The term "cycloalkenyl" refers to an alicyclic unsaturated hydrocarbon group with 3 to 7 carbons containing one carbon-carbon double bond, and includes cyclopropenyl, cyclobutenyl, cyclopentenyl or cyclohexenyl, preferably an alicyclic unsaturated hydrocarbon group with 3 to 6 carbons.

The term "halogen" or "halogeno" refers to fluorine, chlorine, bromine and iodine.

The term "alkoxy" refers to a group wherein an oxygen atom binds to the above straight or branched-chain alkyl with 1 to 6 carbons, and includes methoxy, ethoxy, propoxy, isopropoxy, butoxy, t-butoxy, isobutoxy, and various branched-chain isomers thereof, preferably a group wherein an oxygen atom binds to straight or branched-chain saturated hydrocarbon chain with 1 to 4 carbons.

The term "alkanoyl" refers to a group with 2 to 7 carbons wherein the above alkyl binds to carbonyl, and includes acetyl, propanoyl, butyryl, pentanoyl and various branched-chain isomers thereof, preferably a group with 2 to 5 carbons wherein straight or branched-chain saturated hydrocarbon chain with 1 to 4 carbons binds to carbonyl.

The terms "halogenoalkyl", "halogenoalkoxy" and "halogenocycloalkyl" refer to the above alkyl, alkoxy and cycloalkyl which are substituted with 1 to 7 halogen atoms, respectively.

The terms "fluoroalkyl", "fluoroalkoxy" and "fluorocycloalkyl" refer to the above alkyl, alkoxy and cycloalkyl which are substituted with 1 to 7 fluorine atoms, respectively.

The term "monocyclic aromatic heterocyclic group" refers to a 5 to 6-membered monocyclic aromatic heterocyclic group containing carbon atoms and 1 to 4 heteroatoms selected from oxygen atom, sulfur atom and nitrogen atom, and includes pyrrolyl, furyl, thienyl, pyrazolyl, imidazolyl, oxazolyl, isooxazolyl, thiazolyl, isothiazolyl, thiadiazolyl, pyridyl, pyrimidyl or pyridazyl.

The term "monocyclic non-aromatic heterocyclic group" refers to a 4 to 7-membered monocyclic non-aromatic heterocyclic group containing carbon atoms and 1 to 4 heteroatoms selected from oxygen atom, sulfur atom and nitrogen atom, and includes pyrrolidinyl, piperidinyl, tetrahydrofuryl, tetrahydrothienyl, and morpholyl.

The term "monocyclic nitrogen-containing non-aromatic heterocyclic group" refers to the above monocyclic non-aromatic heterocyclic group containing at least one nitrogen atom, and includes pyrrolidyl, piperidinyl and morpholyl.

Each definition of each symbol in the compound of the formula (I) is explained in detail as follows.

The number of the substituents in the "optionally substituted alkyl" of $R^1$ may be one or more (for example, 1 to 7), and the substituents may be the same or different. As for such substituents, cycloalkyl, alkoxy, halogen, oxo and hydroxy can be mentioned for example.

The number of the substituents in the "optionally substituted cycloalkyl" of $R^1$ may be one or more (for example, 1 to 7), and the substituents may be the same or different. As for such substituents, alkyl, alkoxy and halogen can be mentioned for example.

$R^1$ is preferably $C_1$-$C_6$ alkyl optionally substituted with 1 to 7 halogen (particularly, fluorine atom(s)), or $C_3$-$C_7$ cycloalkyl, and specifically, methyl, trifluoromethyl, or cyclopropyl is preferable.

The number of the substituents in the "optionally substituted cycloalkyl" of $R^2$ may be one or more (for example, 1 to 7), and the substituents may be the same or different. As for such substituents, alkyl, alkoxy and halogen can be mentioned for example.

$R^2$ is preferably hydrogen or $C_3$-$C_7$ cycloalkyl, and specifically, hydrogen or cyclopropyl is preferable.

The number of the substituents in the "optionally substituted alkyl" of $R^3$ may be one or more (for example, 1 to 7), and the substituents may be the same or different. As for such substituents, cycloalkyl, halogenocycloalkyl (in which the cycloalkyl and halogenocycloalkyl may be optionally substituted with 1 to 3 groups each independently selected from alkyl and halogenoalkyl), alkoxy, halogenoalkoxy, phenyl, a monocyclic aromatic heterocyclic group, a monocyclic non-aromatic heterocyclic group (in which the phenyl, aromatic heterocyclic group and non-aromatic heterocyclic group may be optionally substituted with 1 to 3 groups each independently selected from alkyl, halogenoalkyl, cycloalkyl, halogenocycloalkyl, alkoxy, halogenoalkoxy and halogen), halogen, oxo and hydroxy can be mentioned for example.

The number of the substituents in the "optionally substituted alkoxy" of $R^3$ may be one or more (for example, 1 to 7), and the substituents may be the same or different. As for such substituents, cycloalkyl, halogenocycloalkyl (in which the cycloalkyl and halogenocycloalkyl may be optionally substituted with 1 to 3 groups each independently selected from alkyl and halogenoalkyl), alkoxy, halogenoalkoxy, phenyl, a monocyclic aromatic heterocyclic group, a monocyclic non-aromatic heterocyclic group (in which the phenyl, aromatic heterocyclic group and non-aromatic heterocyclic group may be optionally substituted with 1 to 3 groups each independently selected from alkyl, halogenoalkyl, cycloalkyl, halogenocycloalkyl, alkoxy, halogenoalkoxy and halogen), halogen and hydroxy can be mentioned for example.

$R^3$ is preferably (a) $C_1$-$C_6$ alkyl optionally substituted with 1 to 7 groups selected from $C_3$-$C_7$ cycloalkyl (in which the cycloalkyl may be optionally substituted with 1 to 3 groups selected from $C_1$-$C_6$ alkyl and $C_1$-$C_6$ halogenoalkyl), $C_1$-$C_6$ alkoxy, $C_1$-$C_6$ halogenoalkoxy and halogen; or (b) $C_1$-$C_6$ alkoxy optionally substituted with 1 to 7 groups selected from $C_3$-$C_7$ cycloalkyl, $C_1$-$C_6$ alkoxy, $C_1$-$C_6$ halogenoalkoxy and halogen, particularly, $C_1$-$C_6$ alkyl optionally substituted with 1 to 7 halogen (particularly, fluorine atom(s)) or $C_1$-$C_6$ alkoxy optionally substituted with 1 to 7 halogen (particularly, fluorine atom(s)) is preferable, and specifically, trifluoromethyl or trifluoromethoxy is preferable.

The number of the substituents in the "optionally substituted alkyl" of $R^4$ may be one or more (for example, 1 to 7), and the substituents may be the same or different. As for such substituents, cycloalkyl, alkoxy, halogen, oxo and hydroxy can be mentioned for example.

$R^4$ is preferably $C_1$-$C_6$ alkyl, and specifically, methyl is preferable.

The number of the substituents in the "optionally substituted alkyl" of $R^6$ may be one or more (for example, 1 to 7), and the substituents may be the same or different. As for such substituents, cycloalkyl, alkoxy, halogen, oxo and hydroxy can be mentioned for example.

The number of the substituents in the "optionally substituted cycloalkyl" of $R^6$ may be one or more (for example, 1 to 7), and the substituents may be the same or different. As for such substituents, alkyl, alkoxy and halogen can be mentioned for example.

The number of the substituents in the "optionally substituted alkoxy" of $R^6$ may be one or more (for example, 1 to 7), and the substituents may be the same or different. As for such substituents, alkoxy, cycloalkyl and halogen can be mentioned for example.

The number of the substituents in the "optionally substituted alkylamino" of $R^6$ may be one or more (for example, 1 to 7), and the substituents may be the same or different. As for such substituents, alkoxy, cycloalkyl and halogen can be mentioned for example.

The number of the substituents in the "optionally substituted dialkylamino" of $R^6$ may be one or more (for example, 1 to 7), and the substituents may be the same or different. As for such substituents, alkoxy, cycloalkyl and halogen can be mentioned for example.

The number of the substituents in the "optionally substituted monocyclic nitrogen-containing non-aromatic heterocyclic group" of $R^6$ may be one or more (for example, 1 to 3), and the substituents may be the same or different. As for such substituents, alkyl, halogenoalkyl, cycloalkyl, halogenocycloalkyl, alkoxy, halogenoalkoxy and halogen can be mentioned for example.

The number of the substituents in the "optionally substituted phenyl" of $R^6$ may be one or more (for example, 1 to 3), and the substituents may be the same or different. As for such substituents, alkyl, halogenoalkyl, cycloalkyl, halogenocycloalkyl, alkoxy, halogenoalkoxy and halogen can be mentioned for example.

$R^6$ is preferably (a) $C_1$-$C_6$ alkyl optionally substituted with 1 to 7 groups selected from $C_1$-$C_6$ alkoxy and halogen (particularly, fluorine atom(s)); (b) $C_3$-$C_7$ cycloalkyl; (c) $C_1$-$C_6$ alkoxy; (d) $C_1$-$C_6$ alkylamino; (e) $C_2$-$C_{12}$ dialkylamino; (f) a monocyclic nitrogen-containing non-aromatic heterocyclic group; (g) phenyl; or (h) halogen, and specifically, methyl, ethyl, propyl, isopropyl, trifluoromethyl, methoxymethyl, cyclopropyl, methoxy, methylamino, dimethylamino, pyrrolidyl, piperidyl, morpholyl, phenyl, fluoro, chloro, or bromo is preferable. More preferably, $R^6$ is (a) $C_1$-$C_6$ alkyl optionally substituted with 1 to 7 groups selected from $C_1$-$C_6$ alkoxy and halogen (particularly, fluorine atom(s)); (b) $C_3$-$C_7$ cycloalkyl; (c) $C_1$-$C_6$ alkoxy; (d) $C_1$-$C_6$ alkylamino; (e) $C_2$-$C_{12}$ dialkylamino; (f) a monocyclic nitrogen-containing non-aromatic heterocyclic group; or (g) phenyl, and specifically, methyl, ethyl, propyl, isopropyl, trifluoromethyl, methoxymethyl, cyclopropyl, methoxy, methylamino, dimethylamino, pyrrolidyl, piperidyl, morpholyl, or phenyl is preferable. Particularly preferably, $R^6$ is (a) $C_1$-$C_6$ alkyl; (b) $C_3$-$C_7$ cycloalkyl; (c) $C_1$-$C_6$ alkylamino; (d) $C_2$-$C_{12}$ dialkylamino; or (e) a monocyclic nitrogen-containing non-aromatic heterocyclic group is preferable, and specifically, methyl, ethyl, propyl, isopropyl, cyclopropyl, methoxy, methylamino, dimethylamino, pyrrolidyl, piperidyl, or morpholyl.

The number of the substituents in the "optionally substituted alkyl" of $R^7$ may be one or more (for example, 1 to 7), and the substituents may be the same or different. As for such substituents, cycloalkyl, alkoxy, halogen, oxo and hydroxy can be mentioned for example.

$R^7$ is preferably a hydrogen atom, $C_1$-$C_6$ alkyl, or halogen (particularly, fluoro), and specifically, a hydrogen atom, methyl, or fluoro is preferable.

The number of the substituents in the "optionally substituted triazolyl" of $X^1$ or $X^2$ may be one. As for such substituents, alkyl and halogenoalkyl (particularly, fluoroalkyl) can be mentioned for example.

The number of the substituents in the "optionally substituted alkanoylaminomethyl" of $X^1$ or $X^2$ may be one or more (for example, 1 to 3), and the substituents may be the same or different. As for such substituents, halogen can be mentioned for example.

The number of the substituents in the "optionally substituted alkylsulfonylaminomethyl" of $X^1$ or $X^2$ may be one or more (for example, 1 to 3), and the substituents may be the same or different. As for such substituents, halogen (particularly, fluorine) can be mentioned for example.

$X^1$ or $X^2$ is preferably each independently (a) tetrazolyl; (b) tetrazolinonyl; (c) triazolyl optionally substituted with one group selected from $C_1$-$C_6$ alkyl, and $C_1$-$C_6$ halogenoalkyl (particularly, $C_1$-$C_6$ fluoroalkyl); (d) triazolinonyl; (e) oxadiazolonyl; (f) $C_2$-$C_7$ alkanoylaminomethyl optionally substituted with 1 to 3 halogen (particularly, fluorine); (g) $C_1$-$C_6$ alkylsulfonylaminomethyl optionally substituted with 1 to 3 halogen (particularly, fluorine), and specifically, tetrazolyl, tetrazolinonyl, triazolyl, methyltriazolyl, trifluoromethyltriazolyl, triazolinonyl, oxadiazolonyl, acetylaminomethyl, methylsulfonylaminomethyl, or trifluoromethylsulfonylaminomethyl is preferable.

The pharmaceutically acceptable salt of the compound of the formula (I) includes an alkali metal salt such as lithium, sodium, or potassium, etc.; a group-II metal salt such as calcium, or magnesium, etc.; a salt with zinc or aluminum; a salt with an amine such as ammonia, choline, diethanolamine, lysine, ethylenediamine, t-butylamine, t-octylamine, tris(hydroxymethyl)aminomethane, N-methyl-glucosamine, triethanolamine, or dehydroabietylamine; a salt with an inorganic acid such as hydrochloric acid, hydrobromic acid, hydroiodic acid, sulfuric acid, nitric acid, or phosphoric acid; a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, or benzenesulfonic acid; or a salt with an acidic amino acid such as aspartic acid, or glutamic acid.

The pharmaceutically acceptable salt of the compound of the formula (I) includes an intramolecular salt, a hydrate, and a solvate thereof.

The compound (I) of the present invention may exist in the form of a tautomer or a mixture thereof. The compound (I) of the present invention may optionally have one or more asymmetric carbon atoms which are contained in any one of substituents. Further, the compound of the formula (I) may exist in the form of a stereoisomer such as enantiomer or diastereomer, or a mixture thereof. The compound of the present invention encompasses a mixture of tautomers or stereoisomers, or each pure or substantially pure isomer.

The compound of the formula (I) which is obtained in the form of a stereoisomer such as diastereomer or enantiomer may be separated by a conventional method known in the art, for example, chromatography or fractional crystallization.

A preferable embodiment of the present invention relates to

[2] the compound according to the above item [1], wherein
$R^1$ is $C_1$-$C_6$ alkyl, $C_1$-$C_6$ halogenoalkyl, or $C_3$-$C_7$ cycloalkyl, and
$R^2$ is a hydrogen atom or $C_3$-$C_7$ cycloalkyl,
or a pharmaceutically acceptable salt thereof.

Another preferable embodiment of the present invention relates to

[3] the compound according to the above item [1] or [2], wherein $R^3$ is $C_1$ halogenoalkyl (particularly, $C_1$-$C_6$ fluoroalkyl) or $C_1$-$C_6$ halogenoalkoxy (particularly, $C_1$-$C_6$ fluoroalkoxy), or a pharmaceutically acceptable salt thereof.

Another preferable embodiment of the present invention relates to

[4] the compound according to any one of the above items [1] to [3], wherein
Ring A is the formula (i) or formula (ii),
$R^4$ is $C_1$-$C_6$ alkyl, and
$X^1$ and $X^2$ are each independently tetrazolyl, tetrazolinonyl, triazolyl, $C_1$-$C_6$ alkyltriazolyl, $C_1$-$C_6$ halogenoalkyltriazolyl, triazolinonyl, oxadiazolonyl, $C_2$-$C_7$ alkanoylaminomethyl, $C_1$-$C_6$ alkylsulfonylaminomethyl, or $C_1$-$C_6$ halogenoalkylsulfonylaminomethyl, or
$R^4$ and $X^2$ combine with each other at their terminals together with the adjacent benzene to form indazolinonyl or benzoisoxazolonyl,
or a pharmaceutically acceptable salt thereof.

More preferable embodiment of the present invention relates to

[5] the compound according to any one of the above items [1] to [3], wherein
Ring A is the formula (i) or formula (ii),
$R^4$ is $C_1$-$C_6$ alkyl, and
$X^1$ and $X^2$ are each independently tetrazolyl, tetrazolinonyl, triazolyl, $C_1$-$C_6$ alkyltriazolyl, $C_1$-$C_6$ halogenoalkyltriazolyl, triazolinonyl, or oxadiazolonyl, or
$R^4$ and $X^2$ combine with each other at their terminals together with the adjacent benzene to form indazolinonyl or benzoisoxazolonyl,
or a pharmaceutically acceptable salt thereof.

Another preferable embodiment of the present invention relates to

[6] the compound according to the above item [1], wherein
$R^1$ is $C_1$-$C_6$ alkyl, $C_1$-$C_6$ halogenoalkyl, or $C_3$-$C_7$ cycloalkyl,
$R^2$ is a hydrogen atom or $C_3$-$C_7$ cycloalkyl,
$R^3$ is $C_1$-$C_6$ halogenoalkyl or $C_1$-$C_6$ halogenoalkoxy,
Ring A is the formula (i) or (ii),
$R^4$ is $C_1$-$C_6$ alkyl, and
$X^1$ and $X^2$ are each independently tetrazolyl, tetrazolinonyl, triazolyl, $C_1$-$C_6$ alkyltriazolyl, $C_1$-$C_6$ halogenoalkyltriazolyl, triazolinonyl, oxadiazolonyl, $C_2$-$C_7$ alkanoylaminomethyl, $C_1$-$C_6$ alkylsulfonylaminomethyl, or $C_1$-$C_6$ halogenoalkylsulfonylaminomethyl, or
$R^4$ and $X^2$ combine with each other at their terminals together with the adjacent benzene to form indazolinonyl or benzoisoxazolonyl,
or a pharmaceutically acceptable salt thereof.

Still another preferable embodiment of the present invention relates to

[7] the compound according to any one of the above items [1] to [6], wherein
Ring A is the formula (i) or formula (ii),
$R^4$ is $C_1$-$C_6$ alkyl, and $X^1$ and $X^2$ are each independently the following formula (iii), (iv), (v), (vi), or (vii):

(iii)

(iv)

(v)

(vi)

(vii)

wherein $R^5$ is a hydrogen atom, $C_1$-$C_6$ alkyl, or $C_1$-$C_6$ halogenoalkyl, and $V^1$ is NH or O, or $R^4$ and $X^2$ combine with each other at their terminals together with the adjacent benzene to form the following formula (viii):

(viii)

wherein $V^2$ is NH or O, or a pharmaceutically acceptable salt thereof.

More preferable embodiment of the present invention relates to

[8] the compound according to any one of the above items [1] to [6], wherein

Ring A is the formula (i) or formula (ii), $R^4$ is $C_1$-$C_6$ alkyl, $X^1$ and $X^2$ are each independently the following formula (iii), (iv), (v-a), or (vii-a):

(iii)

(iv)

(v-a)

(vii-a)

wherein $R^{5a}$ is a hydrogen atom or $C_1$-$C_6$ alkyl, or $R^4$ and $X^2$ combine with each other at their terminals together with the adjacent benzene to form the following formula (viii-a):

(viii-a)

$Y^1$ is CH, and
$Y^2$ is CH or N,
or a pharmaceutically acceptable salt thereof.

Another preferable embodiment of the present invention relates to

[9] the compound according to any one of the above items [1] to [8], wherein $R^1$ is cyclopropyl, $R^2$ is a hydrogen atom, $R^3$ is $C_1$-$C_6$ fluoroalkyl or $C_1$-$C_6$ fluoroalkoxy, and Ring A is the formula (i) or formula (ii), or a pharmaceutically acceptable salt thereof.

Still another preferable embodiment of the present invention relates to

[10] the compound according to any one of the above items [1] to [8], wherein $R^1$ is trifluoromethyl, $R^2$ is a hydrogen atom, $R^3$ is $C_1$-$C_6$ fluoroalkoxy, Z is CH, and Ring A is the formula (i) or formula (ii), or a pharmaceutically acceptable salt thereof.

A preferable embodiment of the present invention relates to

[11] the compound according to any one of the above items [1] to [8], wherein $R^1$ is methyl, $R^2$ is cyclopropyl, $R^3$ is $C_1$-$C_6$ fluoroalkoxy, Z is CH, and Ring A is the formula (i) or formula (ii), or a pharmaceutically acceptable salt thereof.

Another preferable embodiment of the present invention relates to

[12] the compound according to the above item [1], wherein $R^1$ is $C_1$-$C_6$ alkyl, $C_1$-$C_6$ halogenoalkyl, or $C_3$-$C_7$ cycloalkyl, $R^2$ is a hydrogen atom or $C_3$-$C_7$ cycloalkyl, $R^3$ is $C_1$-$C_6$ halogenoalkyl (particularly, $C_1$-$C_6$ fluoroalkyl) or $C_1$-$C_6$ halogenoalkoxy (particularly, $C_1$-$C_6$ fluoroalkoxy), Z is CH or N, Ring A is the formula (i) or (ii), $R^4$ is $C_1$-$C_6$ alkyl, $X^1$ and $X^2$ are each independently the following formula (iii), (iv), (v-a), or (vii-a):

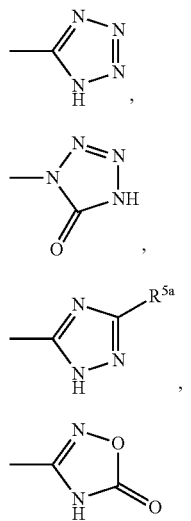

wherein $R^{5a}$ is a hydrogen atom or $C_1$-$C_6$ alkyl, or $R^4$ and $X^2$ combine with each other at their terminals together with the adjacent benzene to form the following formula (viii-a):

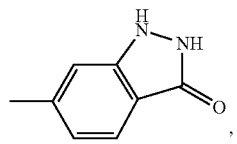

$Y^1$ is CH, and $Y^2$ is CH or N, or a pharmaceutically acceptable salt thereof.

More preferable embodiment of the present invention relates to

[13] the compound according to the above item [12], wherein $R^1$ is $C_1$-$C_6$ halogenoalkyl or $C_3$-$C_7$ cycloalkyl, $R^2$ is a hydrogen atom, $R^3$ is $C_1$-$C_6$ halogenoalkoxy (particularly, $C_1$-$C_6$ fluoroalkoxy), Ring A is the formula (i), $X^1$ is the formula (iv), (v-a), or (vii-a), and Z is CH, or a pharmaceutically acceptable salt thereof.

Another preferable embodiment of the present invention relates to

[14] the compound according to any one of the above items [1] to [3], wherein

Ring A is the formula (ix), $R^6$ is (a) $C_1$-$C_6$ alkyl optionally substituted with 1 to 7 groups selected from $C_1$-$C_6$ alkoxy and halogen (particularly, fluorine atom(s)); (b) $C_3$-$C_7$ cycloalkyl; (c) $C_1$-$C_6$ alkoxy; (d) $C_1$-$C_6$ alkylamino; (e) $C_2$-$C_{12}$ dialkylamino; (f) a monocyclic nitrogen-containing non-aromatic heterocyclic group; (g) phenyl; or (h) halogen, and $R^7$ is a hydrogen atom, $C_1$-$C_6$ alkyl, or halogen (particularly, fluoro), or a pharmaceutically acceptable salt thereof.

More preferable embodiment of the present invention relates to

[15] the compound according to any one of the above items [1] to [3], wherein

Ring A is the formula (ix), and $R^6$ is (a) $C_1$-$C_6$ alkyl optionally substituted with 1 to 7 groups selected from $C_1$-$C_6$ alkoxy and halogen; (b) $C_3$-$C_7$ cycloalkyl; (c) $C_1$-$C_6$ alkoxy; (d) $C_1$-$C_6$ alkylamino; (e) $C_2$-$C_{12}$ dialkylamino; (f) a monocyclic nitrogen-containing non-aromatic heterocyclic group; or (g) phenyl, or a pharmaceutically acceptable salt thereof.

Another preferable embodiment of the present invention relates to

[16] the compound according to the above item [1], wherein $R^1$ is $C_1$-$C_6$ alkyl, $C_1$-$C_6$ halogenoalkyl, or $C_3$-$C_7$ cycloalkyl, $R^2$ is a hydrogen atom or $C_3$-$C_7$ cycloalkyl, $R^3$ is $C_1$-$C_6$ halogenoalkyl or $C_1$-$C_6$ halogenoalkoxy, Ring A is the formula (ix), $R^6$ is (a) $C_1$-$C_6$ alkyl optionally substituted with 1 to 7 groups selected from $C_1$-$C_6$ alkoxy and halogen; (b) $C_3$-$C_7$ cycloalkyl; (c) $C_1$-$C_6$ alkoxy; (d) $C_1$-$C_6$ alkylamino; (e) $C_2$-$C_{12}$ dialkylamino; (f) a monocyclic nitrogen-containing non-aromatic heterocyclic group; (g) phenyl; or (h) halogen, and $R^7$ is a hydrogen atom, $C_1$-$C_6$ alkyl, or halogen, or a pharmaceutically acceptable salt thereof.

Still another preferable embodiment of the present invention relates to

[17] the compound according to any one of the above items [1] to [3] and [14] to [16], wherein Ring A is the following formula (ix-a):

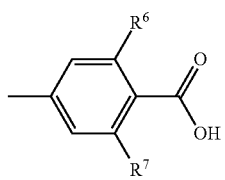

wherein the symbols are the same as defined above, or a pharmaceutically acceptable salt thereof.

More preferable embodiment of the present invention relates to

[18] the compound according to any one of the above items [1] to [3] and [14] to [16], wherein Ring A is the formula (ix) or formula (ix-a), $R^6$ is (a) $C_1$-$C_6$ alkyl optionally substituted with 1 to 7 groups selected from $C_1$-$C_6$ alkoxy and halogen; (b) $C_3$-$C_7$ cycloalkyl; (c) $C_1$-$C_6$ alkoxy; (d) $C_1$-$C_6$ alkylamino; (e)

$C_2$-$C_{12}$ dialkylamino; (f) a monocyclic nitrogen-containing non-aromatic heterocyclic group; or (g) phenyl, and $R^7$ is a hydrogen atom, $C_1$-$C_6$ alkyl, or halogen (particularly, fluoro), or a pharmaceutically acceptable salt thereof.

Particularly preferable embodiment of the present invention relates to

[19] the compound according to any one of the above items [1] to [3] and [14] to [16], wherein Ring A is the formula (ix) or formula (ix-a), $R^6$ is (a) $C_1$-$C_6$ alkyl; (b) $C_3$-$C_7$ cycloalkyl; (c) $C_1$-$C_6$ alkylamino; (d) $C_2$-$C_{12}$ dialkylamino; or (e) a monocyclic nitrogen-containing non-aromatic heterocyclic group, and $R^7$ is a hydrogen atom, or a pharmaceutically acceptable salt thereof.

Another preferable embodiment of the present invention relates to

[20] the compound according to any one of the above items [1] to [3] and [14] to [19], wherein $R^1$ is cyclopropyl, $R^2$ is a hydrogen atom, $R^3$ is $C_1$-$C_6$ fluoroalkyl or $C_1$-$C_6$ fluoroalkoxy, Ring A is the formula (ix) or formula (ix-a), or a pharmaceutically acceptable salt thereof.

Still another preferable embodiment of the present invention relates to

[21] the compound according to any one of the above items [1] to [3] and [14] to [19], wherein $R^1$ is trifluoromethyl, $R^2$ is a hydrogen atom, $R^3$ is $C_1$-$C_6$ fluoroalkoxy, Z is CH, Ring A is the formula (ix) or formula (ix-a), or a pharmaceutically acceptable salt thereof.

A preferable embodiment of the present invention relates to

[22] the compound according to any one of the above items [1] to [3] and [14] to [19], wherein $R^1$ is methyl, $R^2$ is cyclopropyl, $R^3$ is $C_1$-$C_6$ fluoroalkoxy, Z is CH, Ring A is the formula (ix) or formula (ix-a), or a pharmaceutically acceptable salt thereof.

Another preferable embodiment of the present invention relates to

[23] the compound according to the above item [1], wherein $R^1$ is $C_1$-$C_6$ alkyl, $C_1$-$C_6$ halogenoalkyl, or $C_3$-$C_7$ cycloalkyl, $R^2$ is a hydrogen atom or $C_3$-$C_7$ cycloalkyl, $R^3$ is $C_1$-$C_6$ halogenoalkyl (particularly, $C_1$-$C_6$ fluoroalkyl) or $C_1$-$C_6$ halogenoalkoxy (particularly, $C_1$-$C_6$ fluoroalkoxy), Z is CH or N, Ring A is the formula (ix-a), $R^6$ is (a) $C_1$-$C_6$ alkyl; (b) $C_3$-$C_7$ cycloalkyl; (c) $C_1$-$C_6$ alkylamino; (d) $C_2$-$C_{12}$ dialkylamino; or (e) a monocyclic nitrogen-containing non-aromatic heterocyclic group, and $R^7$ is a hydrogen atom, or a pharmaceutically acceptable salt thereof.

A preferable embodiment of the present invention relates to

[24] the compound according to the above item [23], wherein $R^1$ is cyclopropyl, $R^2$ is a hydrogen atom, $R^3$ is $C_1$-$C_6$ halogenoalkoxy (particularly, $C_1$-$C_6$ fluoroalkoxy), Z is CH, and $R^6$ is $C_1$-$C_6$ alkyl or $C_2$-$C_{12}$ dialkylamino or a pharmaceutically acceptable salt thereof.

A preferable compound of the present invention is selected from the group consisting of:

N-(4-cyclopropylisoquinolin-3-yl)-4-(5-oxo-4,5-dihydro-1H-tetrazol-1-yl)-N-[4-(trifluoromethoxy)benzyl]benzenesulfonamide;

N-(4-cyclopropylisoquinolin-3-yl)-6-(5-oxo-4,5-dihydro-1,2,4-oxadiazol-3-yl)-N-[4-(trifluoromethoxy)benzyl]pyridine-3-sulfonamide;

N-(4-(trifluoromethyl)isoquinolin-3-yl)-6-(1H-1,2,4-triazol-5-yl)-N-[4-(trifluoromethoxy)benzyl]pyridine-3-sulfonamide;

N-(4-(trifluoromethyl)isoquinolin-3-yl)-6-(3-methyl-1H-1,2-yl)-N-[4 (trifluoromethoxy)benzyl]pyridine-3-sulfonamide;

4-({(4-cyclopropylisoquinolin-3-yl)[4-(trifluoromethoxy)benzyl]amino}sulfonyl)-2-(dimethylamino)benzoic acid, or a pharmaceutically acceptable salt thereof.

The compounds of the present invention have novel structures in which isoquinolyl binds to a sulfonylamino group, and show excellent TRPM8 antagonistic activities in the menthol-induced calcium influx inhibiting test. The compound of the present invention also shows excellent inhibitory effects on Wet Dog Shakes induced by a TRPM8 agonist (e.g., menthol or icilin) in rat, for example.

Accordingly, the compound of the present invention is useful for the prevention or treatment of (a) chronic pain: such as a neuropathic pain (for example, cold allodynia, diabetic neuropathy, posttherapeutic neuralgia, complex regional pain syndrome, chemotherapy-induced peripheral neuropathy, trigeminal neuralgia, post stroke pain, spinal cord injury pain, neuralgia, or nerve injury-induced neuropathic pain), a nociceptive pain (for example, rheumatoid arthritis, osteoarthritis, postoperative pain, or myofascial pain), or a mixed pain (for example, cancer pain, fibromyalgia syndrome, or chronic low back pain);

(b) cephalalgia: such as migraine, or cluster or tension headache;

(c) urologic disease: such as detrusor overactivity, overactive bladder, urinary incontinence, neurogenic bladder, detrusor hyperreflexia, idiopathic detrusor overactivity, detrusor instability, interstitial cystitis, benign prostatic hyperplasia, chronic prostatitis, or lower urinary tract symptom;

(d) carcinoma: such as prostate cancer or breast cancer;

(e) respiratory disease: such as asthma, COPD (chronic obstructive pulmonary disease), or pulmonary hypertension;

(f) gastrointestinal disease: such as irritable bowel syndrome;

(g) psychiatric disease: such as a mood disorder (for example, depression or bipolar disorder) or an anxiety disorder (for example, anxiety);

(h) neurological disease: such as neurodegenerative disease or stroke; or (i) dermatosis: such as pruritus.

The compound of the present invention is preferably useful for the prevention or treatment of chronic pain or urologic disease, particularly chronic pain.

The compound of the present invention or a pharmaceutically acceptable salt thereof, or a prodrug thereof may be administered orally or parenterally, and may be used in the form of suitable pharmaceutical formulation. The pharmaceutical formulation suitable for oral administration includes a solid formulation such as tablet, granule, capsule, or powder, or a solution formulation, a suspension formulation, or an emulsion formulation. The pharmaceutical formulation suitable for parenteral administration includes suppository; injection or intravenous infusion in which distilled water for injection, physiological saline or an aqueous glucose solution is used; and an inhalant formulation.

The pharmaceutical composition herein may comprise about 0.01 mg/kg to about 100 mg/kg (preferably, about 0.01 mg/kg to about 50 mg/kg, more preferably about 0.01 mg/kg to about 30 mg/kg) of an active ingredient per a unit dose, for example per a tablet, a capsule, a powder, an injection, a suppository, or a teaspoon, and may be administered in the dose of about 0.01 mg/kg/day to about 100 mg/kg/day (preferably, about 0.01 mg/kg/day to about 50 mg/kg/day, more preferably about 0.01 mg/kg/day to about 30 mg/kg/day). The pharmaceutical composition comprising any one of the compounds defined herein and a pharmaceutically acceptable carrier may be used in the method of treating diseases described herein. The dosage form may comprise about 0.01 mg/kg to about 100 mg/kg (preferably, about 0.01 mg/kg to about 50 mg/kg, more preferably about 0.01 mg/kg to about 30 mg/kg) of an active ingredient, and may be formed in any forms suitable for the selected administration mode. The dose may vary according to the administration route, the need of subject, the severity of condition to be treated and the compound to be used. The pharmaceutical composition may be daily or periodically administered.

The compound (I) of the present invention may be prepared by the following method, but the preparation method of said compound is not limited thereto.

It is required and/or desired that a sensitive or reactive group in the interest molecule may be protected during any preparation process of the compound of the present invention. The protection may be achieved by a conventional protecting group. The protecting group and the use thereof are generally described in T. W. Greene, et al., "Protecting Groups in Organic Synthesis", John Wiley & Sons, New York, 2006. The protecting group may be removed in the subsequent process by a conventional method for those skilled in the art.

Among the compound (I) of the present invention, a compound of the formula (I-a):

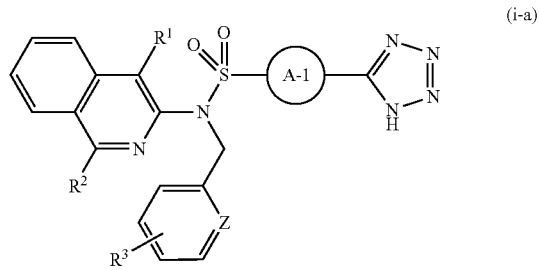

(i-a)

wherein Ring A-1 is the following formula (i-a) or (ii-a):

, or

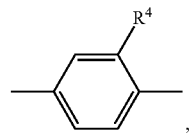

(ii-a)

wherein each bond at the left is the bond to the aminosulfonyl, and the other symbols are the same as defined above, can be prepared according to, for example, the following Scheme I.

Scheme I:

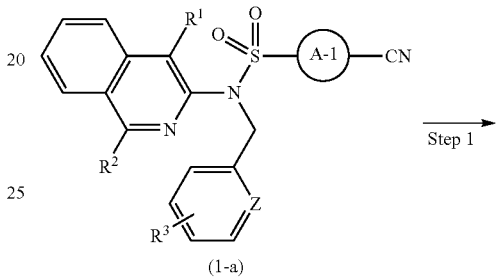

(1-a)

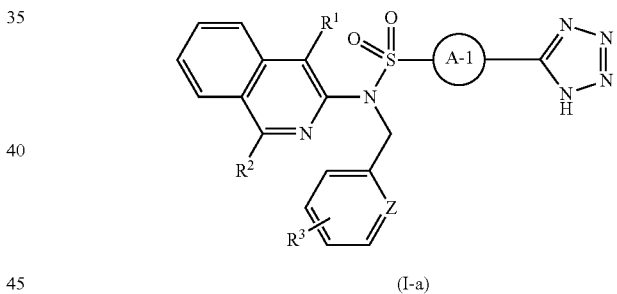

(I-a)

[In the above Scheme, the symbols are the same as defined above.]

The compound of the target formula (I-a) can be prepared from compound (1-a) by tetrazole ring formation.

Step 1:

The tetrazole ring formation reaction of the compound (1-a) can be carried out in a solvent, with or without an acid, and in the presence of an azide.

Examples of the azide include sodium azide, trimethylsilyl azide, and tributyltin azide. Examples of the acid include an ammonium salt such as ammonium chloride. Any solvent which does not affect the reaction may be preferably used as the solvent, and examples of the solvent include an aromatic hydrocarbon such as toluene or xylene; an amide such as N,N-dimethylformamide, N,N-dimethylacetamide, 1,3-dimethyl-2-imidazolidinone, or N-methylpyrrolidone. The reaction may be preferably carried out at 20° C. to 120° C.

Among the compound (I) of the present invention, a compound of the formula (I-b):

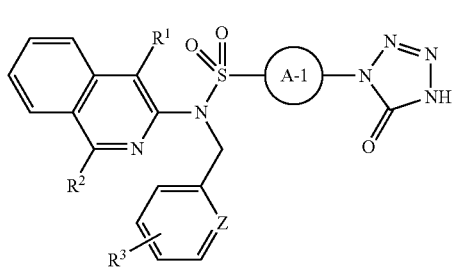

wherein the symbols are the same as defined above, can be prepared according to, for example, the following Scheme II.

Scheme II:

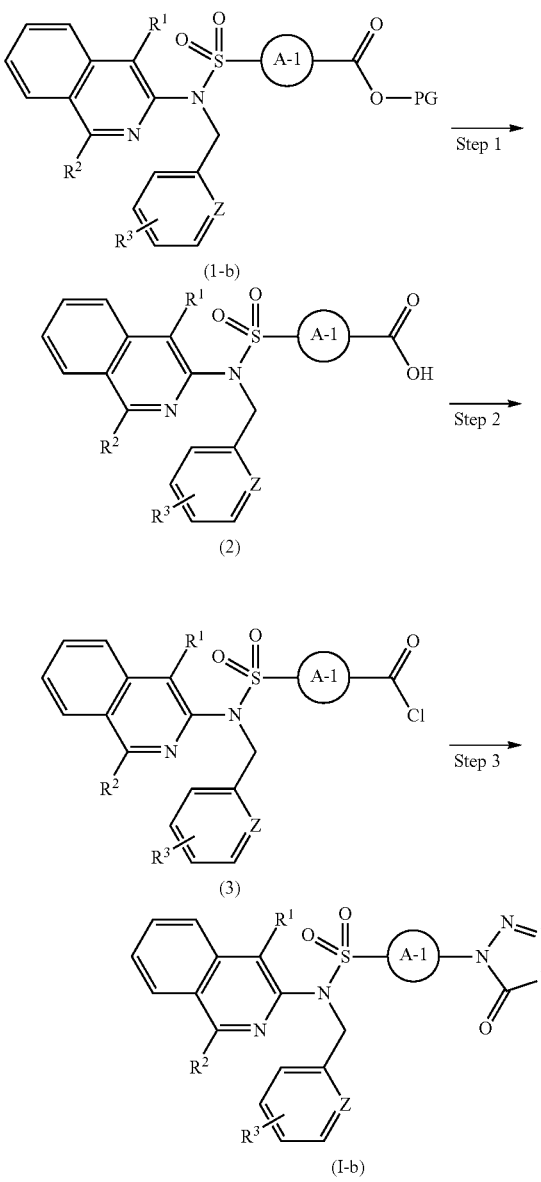

[In the above Scheme, PG is a carboxy protecting group such as alkyl, and the other symbols are the same as defined above.]

The compound of the formula (2) can be obtained by hydrolyzing the compound of the formula (1-b). The compound (3) can be obtained by acid-chloridizing the compound of the formula (2) or a salt thereof. The target compound of the formula (I-b) can be prepared by tetrazolinonylating the compound (3).

Step 1:

The hydrolysis reaction of the compound (1-b) wherein PG is alkyl can be carried out by treating the compound (1-b) with a base and water in a solvent.

Examples of the base include an alkali metal hydroxide such as lithium hydroxide, sodium hydroxide, or potassium hydroxide; and a sodium alkoxide such as sodium methoxide or sodium ethoxide. Any solvent which does not affect the reaction may be preferably used as the solvent, and examples of the solvent include an ether such as tetrahydrofuran or 1,4-dioxane; an alkyl alcohol such as methanol or ethanol; water, and a mixed solvent thereof. The reaction may be preferably carried out at 0° C. to 100° C.

Step 2:

The chlorination reaction of the compound (2) or a salt thereof can be carried out in a solvent, with or without a catalyst, and in the presence of an acid-chloridizing agent.

Examples of the acid-chloridizing agent include oxalyl chloride or thionyl chloride. Examples of the catalyst include N,N-dimethylformamide Any solvent which does not affect the reaction may be preferably used as the solvent, and examples of the solvent include an ether such as tetrahydrofuran, 1,4-dioxane, or 1,2-dimethoxyethane; a halogenohydrocarbon such as dichloromethane, chloroform or 1,2-dichloroethane; and the above-mentioned thionyl chloride; and a mixed solvent thereof. The reaction may be preferably carried out at 20° C. to 80° C.

Step 3:

The tetrazolinonylation reaction of the compound (3) can be carried out in a solvent or without a solvent, and in the presence of an azide.

Examples of the azide include trimethylsilyl azide. Any solvent which does not affect the reaction may be preferably used as the solvent. Preferably, the reaction may be carried out without a solvent. The reaction may be preferably carried out at 60° C. to 120° C.

Among the compound (I) of the present invention, a compound of the formula (I-c):

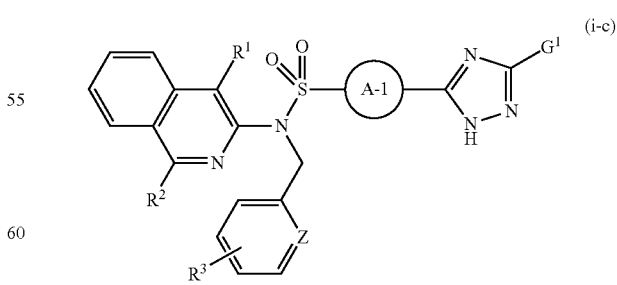

wherein $G^1$ is a hydrogen atom, alkyl, or halogenoalkyl, and the other symbols are the same as defined above, can be prepared according to, for example, the following Scheme III or Scheme IV.

Scheme III:

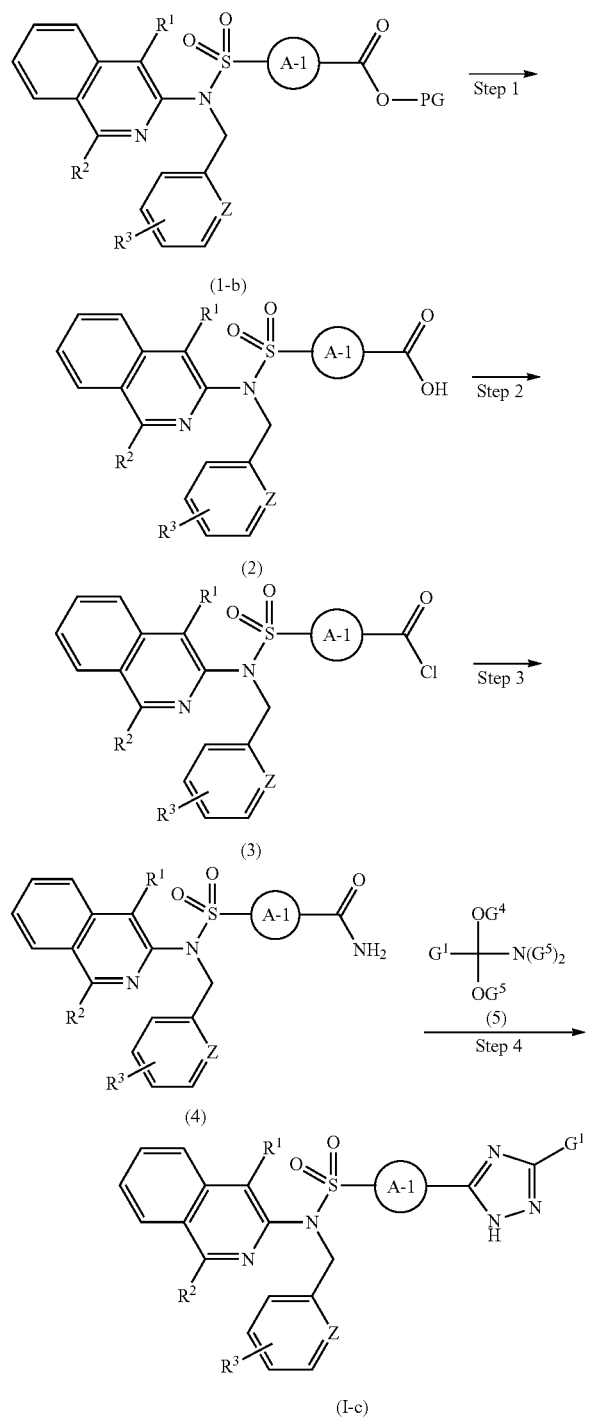

[In the above Scheme, $G^4$ is alkyl, $G^5$ is alkyl, and the other symbols are the same as defined above.]

The compound of the formula (2) can be obtained by hydrolyzing the compound of the formula (1-b). The compound (3) can be obtained by acid-chloridizing the compound of the formula (2) or a salt thereof. The compound of the formula (4) can be obtained by amidating the compound (3). The target compound of the formula (I-c) can be prepared by reacting the compound of the formula (4) with the compound (5) and hydrazine.

Step 1:

The hydrolysis reaction of the compound (1-b) wherein PG is alkyl can be carried out in a similar manner to the hydrolysis reaction of the compound (1-b) in the above Scheme II.

Step 2:

The chlorination reaction of the compound (2) or a salt thereof can be carried out in a similar manner to the chlorination reaction of the compound (2) or a salt thereof in the above Scheme II.

Step 3:

The amidation reaction of the compound (3) can be carried out by treating the compound (3) with ammonia in a solvent.

Any solvent which does not affect the reaction may be preferably used as the solvent, and examples of the solvent include an ether such as tetrahydrofuran, 1,4-dioxane, or 1,2-dimethoxyethane; a halogenohydrocarbon such as dichloromethane, chloroform, or 1,2-dichloroethane; and a mixed solvent thereof. The reaction may be preferably carried out at 0° C. to 50° C.

Step 4:

The reaction to obtain the compound (I-c) can be carried out by condensing the compound (4) with the compound (5) in a solvent or without a solvent, followed by treating the obtained compound with hydrazine monohydrate in a solvent.

Any solvent which does not affect the reaction may be preferably used as the solvent in the condensation reaction of the compound (4) with the compound (5). Preferably, the reaction may be carried out without a solvent. The reaction may be preferably carried out at 80° C. to 150° C.

Any solvent which does not affect the reaction may be preferably used as the solvent in the treatment with hydrazine monohydrate, and examples of the solvent include acetic acid. The reaction may be preferably carried out at 60° C. to 120° C.

Scheme IV:

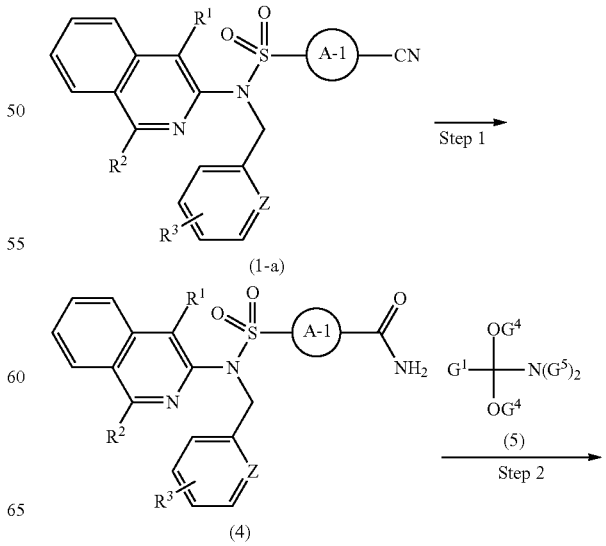

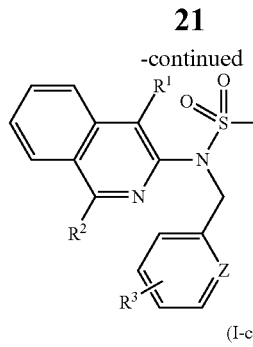

(I-c)

Scheme V:

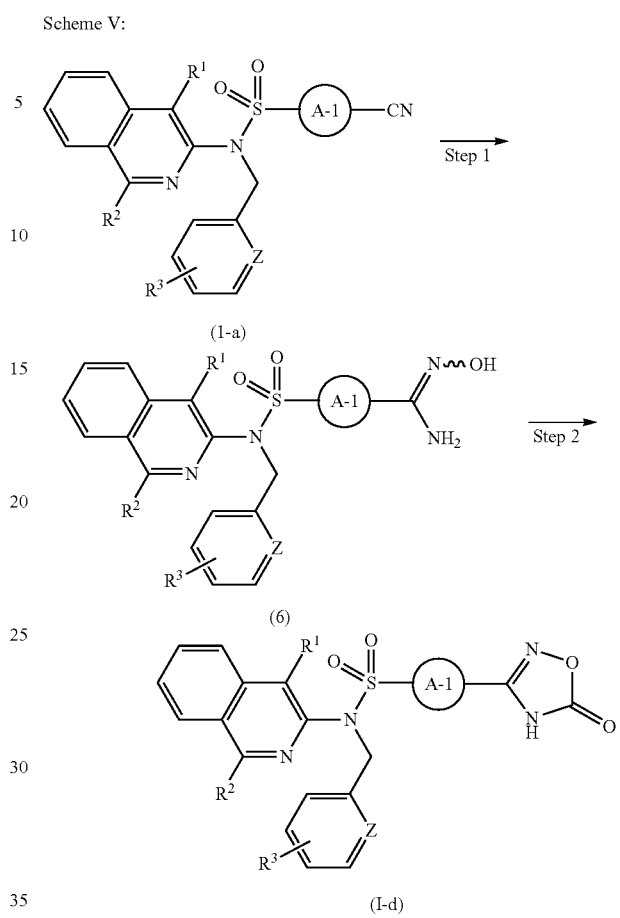

[In the above Scheme, the symbols are the same as defined above.]

The compound of the formula (4) can be obtained by hydrolyzing the compound of the formula (1-a). The target compound of the formula (I-c) can be prepared by reacting the compound of the formula (4) with the compound (5) and hydrazine.

Step 1:

The hydrolysis reaction of the compound (1-a) can be carried out by treating the compound (1-a) with a base in a solvent.

Examples of the base include an alkali metal hydroxide such as sodium hydroxide or potassium hydroxide; and an alkali metal t-butoxide such as sodium t-butoxide or potassium t-butoxide. Any solvent which does not affect the reaction may be preferably used as the solvent, and examples of the solvent include an ether such as tetrahydrofuran, 1,2-dimethoxyethane, or 1,4-dioxane; an alcohol such as t-butanol; and a mixed solvent thereof. The reaction may be preferably carried out at 20° C. to 100° C.

Alternatively, the hydrolysis reaction of the compound (1-a) can be carried out by treating the compound (1-a) with an acid without a solvent.

Examples of the acid include sulfuric acid. The reaction may be preferably carried out at 0° C. to 100° C.

Step 2:

The reaction to obtain the compound (I-c) can be carried out in a similar manner to the reaction to obtain the compound (I-c) in the above Scheme III.

Among the compound (I) of the present invention, a compound of the formula (I-d):

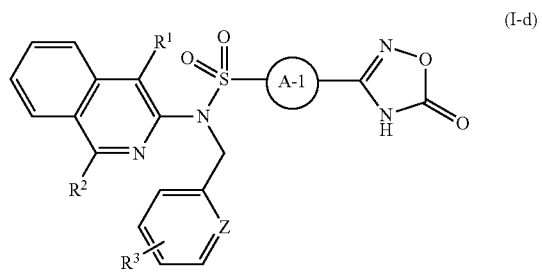

(I-d)

wherein the symbols are the same as defined above, can be prepared according to, for example, the following Scheme V.

[In the above Scheme, the symbols are the same as defined above.]

The compound of the formula (6) can be obtained by amidoximating the compound of the formula (1-a). The target compound of the formula (I-d) can be prepared by oxadiazolonylating the compound of the formula (6).

Step 1:

The amidoximation reaction of the compound (1-a) can be carried out in a solvent, and in the presence of hydroxyamine hydrochloride and a base.

Examples of the base include an amine such as triethylamine, diisopropylethylamine, pyridine, or N-methylmorpholine. Any solvent which does not affect the reaction may be preferably used as the solvent, and examples of the solvent include an alcohol such as methanol or ethanol. The reaction may be preferably carried out at 20° C. to 80° C.

Step 2:

The reaction to obtain the compound (I-d) from the compound (6) can be carried out by condensing the compound (6) with a chloroformate in a solvent and in the presence of a base, followed by cyclizing the obtained compound in a solvent.

Examples of the chloroformate in the condensation reaction include 2-ethylhexyl chloroformate. Examples of the base include an amine such as triethylamine, diisopropylethylamine, pyridine, or N-methylmorpholine. Any solvent which does not affect the reaction may be preferably used as the solvent, and examples of the solvent include an amide such as N,N-dimethylformamide, N,N-dimethylacetamide, 1,3-dimethyl-2-imidazolidinone or N-methylpyrrolidone. The reaction may be preferably carried out at 80° C. to 150° C.

Any solvent which does not affect the reaction may be preferably used as the solvent in the cyclization reaction, and examples of the solvent include an amide such as N,N-dimethylformamide, N,N-dimethylacetamide, 1,3-dimethyl-2-imidazolidinone, or N-methylpyrrolidone. The reaction may be preferably carried out at 100° C. to 180° C.

Alternatively, the reaction to obtain the compound (I-d) from the compound (6) can be carried out in a solvent, and in the presence of a carbonyl source and a base.

Examples of the carbonyl source include carbonyldiimidazole or triphosgene. Examples of the base include an amine such as triethylamine, diisopropylethylamine, pyridine, N-methylmorpholine, or 1,8-diazabicyclo[5.4.0]undec-7-ene; and a $C_2$-$C_7$ fatty acid alkali metal salt such as sodium acetate or potassium acetate, preferably an amine such as triethylamine or 1,8-diazabicyclo[5.4.0]undec-7-ene. Any solvent which does not affect the reaction may be preferably used as the solvent, and examples of the solvent include an ether such as tetrahydrofuran, 1,4-dioxane, or 1,2-dimethoxyethane. The reaction may be preferably carried out at 0° C. to 60° C.

Among the compound (I) of the present invention, a compound of the formula (I-e):

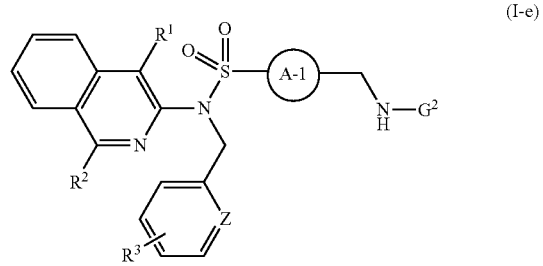

(I-e)

wherein $G^2$ is optionally substituted alkanoyl or optionally substituted alkylsulfonyl, and the other symbols are the same as defined above, can be prepared according to, for example, the following Scheme VI.

Scheme VI:

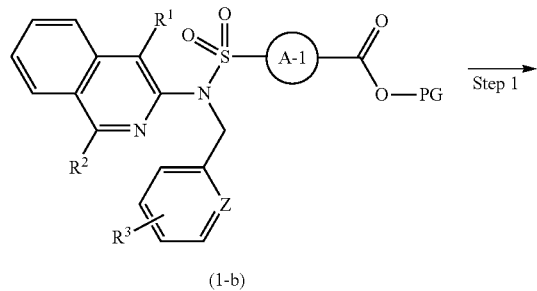

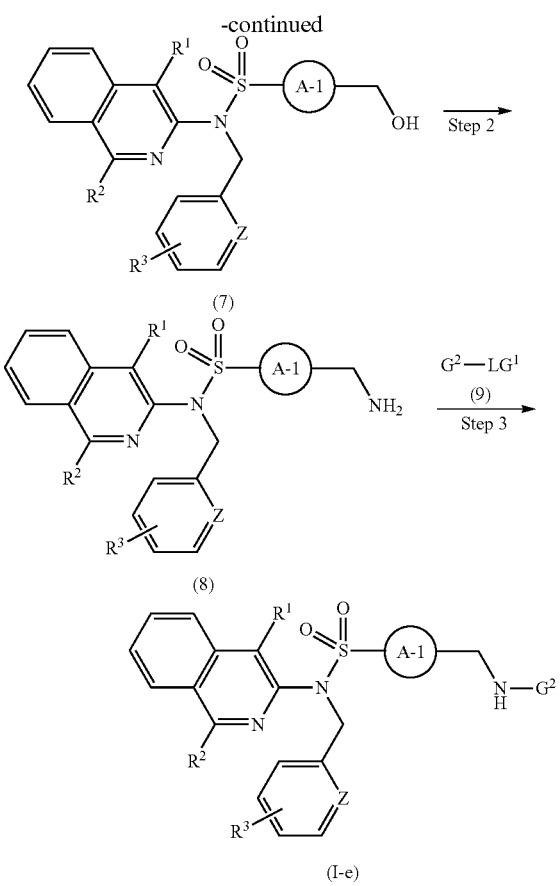

[In the above Scheme, $LG^1$ is a leaving group, for example, a halogen such as chlorine, and —O-$G^2$ (in this case, the compound (9) is an acid anhydride or a sulfonic acid anhydride), and the other symbols are the same as defined above.]

The compound (7) can be obtained by reducing the compound (1-b). The compound (8) can be obtained by aminating the compound (7). The target compound of the formula (I-e) can be prepared by alkanoylating or alkylsulfonylating the compound (8).

Step 1:

The reduction reaction of the compound (1-b) can be carried out in a solvent, and in the presence of a reducing agent.

Examples of the reducing agent include lithium borohydride, sodium borohydride, lithium aluminum hydride, and diisobutylaluminum hydride, preferably diisobutylaluminum hydride. Any solvent which does not affect the reaction may be preferably used as the solvent, and examples of the solvent include an aromatic hydrocarbon such as toluene or xylene; a halogenohydrocarbon such as dichloromethane or chloroform; an ether such as tetrahydrofuran or diethylether; an alcohol such as methanol or ethanol; and a mixed solvent thereof. The reaction may be preferably carried out at −80° C. to 120° C.

Step 2:

The amination reaction of the compound (7) can be carried out by reacting the compound (7) with an azide to obtain an azide, followed by reducing the obtained azide.

The reaction of the compound (7) with the azide can be carried out in a solvent (for example, an ether such as tetrahydrofuran), and in the presence of a base (for example, an amine such as 1,8-diazabicyclo[5.4.0]undec-7-ene). The reaction may be preferably carried out at 0° C. to 50° C.

The reduction reaction of the azide can be carried out in a solvent (for example, an ether such as tetrahydrofuran), and in the presence of a reducing agent (for example, a phosphine such as triphenylphosphine) and water. The reaction may be preferably carried out at 20° C. to 100° C.

Step 3:

The reaction of the compound (8) with the compound (9) can be carried out in a solvent (for example, a halogenohydrocarbon such as dichloromethane), and in the presence of a base (for example, an amine such as triethylamine) The reaction may be preferably carried out at −80° C. to 20° C.

Among the compound (I) of the present invention, a compound of the formula (I-f):

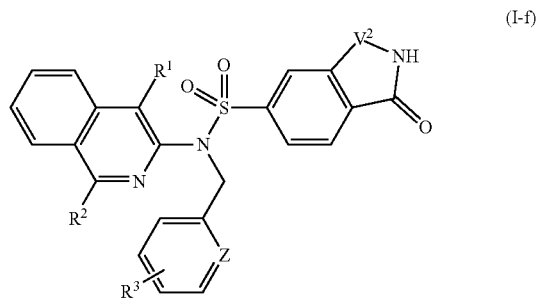

wherein the symbols are the same as defined above, can be prepared according to, for example, the following Scheme VII.

Scheme VII:

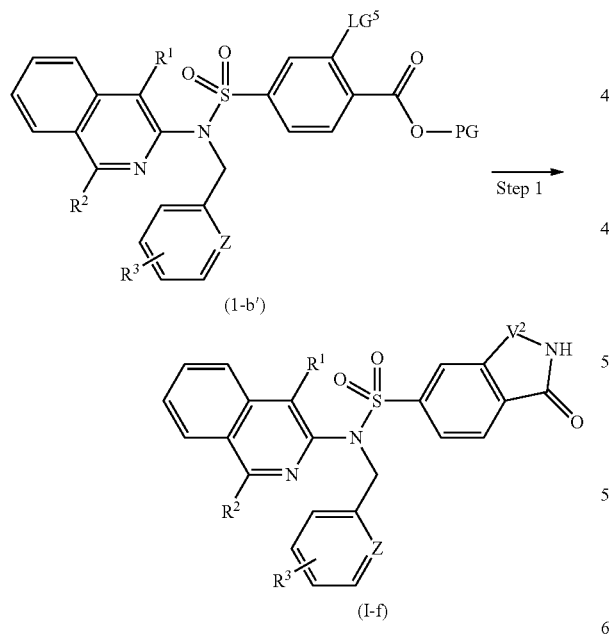

[In the above Scheme, $LG^5$ is a halogen such as fluorine, chlorine, or bromine, and the other symbols are the same as defined above.]

The target compound of the formula (I-f) can be prepared by reacting the compound of the formula (1-b') with hydrazine or hydroxyamine Step 1:

The compound of the formula (I-f) wherein $V^2$ is NH can be prepared by treating the compound (1-b') wherein PG is alkyl with hydrazine in a solvent (for example, an alcohol such as methanol, ethanol, or 2-propanol). The reaction may be preferably carried out at 50° C. to 120° C.

The compound of the formula (I-f) wherein $V^2$ is O can be prepared by hydrolyzing the compound (1-b') wherein PG is alkyl in a solvent (for example, an ether such as tetrahydrofuran, an alcohol such as ethanol, water, or a mixed solvent thereof), followed by condensing the obtained carboxylic acid compound with hydroxyamine by a conventional method known to those skilled in the art, and treating the obtained hydroxamide compound with a base (for example, an alkali metal hydride such as sodium hydride, or an alkali metal hydroxide such as sodium hydroxide) in a solvent.

Among the compound (I) of the present invention, a compound of the formula (I-g):

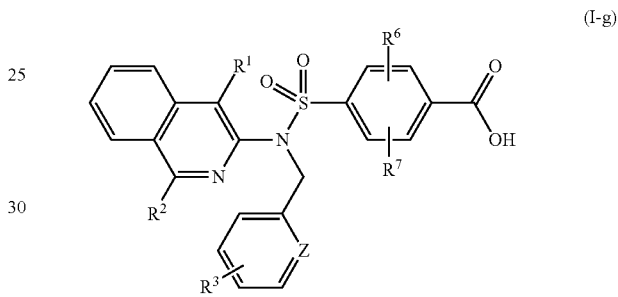

wherein the symbols are the same as defined above, can be prepared, for example, by hydrolyzing a compound of the formula (22):

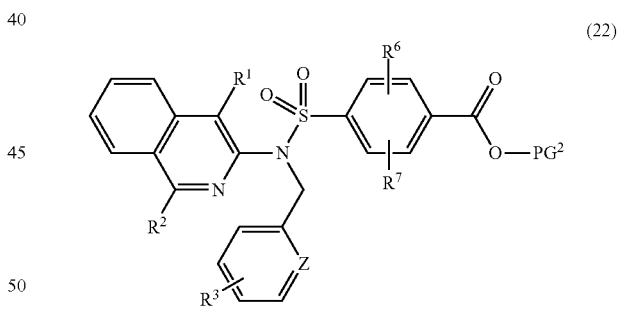

wherein $PG^2$ is a carboxy protecting group, and the other symbols are the same as defined above.

Examples of the protecting group $PG^2$ include alkyl.

The hydrolysis reaction of the compound (22) wherein $PG^2$ is alkyl can be carried out by treating the compound (22) with a base and water in a solvent.

Examples of the base include an alkali metal hydroxide such as lithium hydroxide, sodium hydroxide, or potassium hydroxide; and a sodium alkoxide such as sodium methoxide or sodium ethoxide. Any solvent which does not affect the reaction may be preferably used as the solvent, and examples of the solvent include an ether such as tetrahydrofuran or 1,4-dioxane; an alkyl alcohol such as methanol or ethanol; water; and a mixed solvent thereof. The reaction may be preferably carried out at 0° C. to 100° C.

[Preparation of Intermediate Compounds]
An intermediate compound (1) of the present invention:

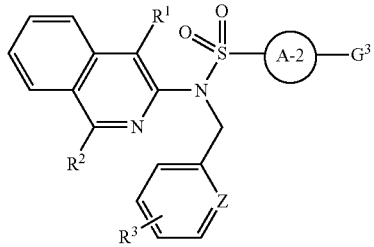
(1)

wherein Ring A-2 is the following formula (i-a), (ii-a), or (ii-b):

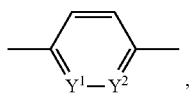
(i-a)

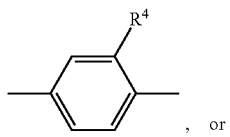
(ii-a)

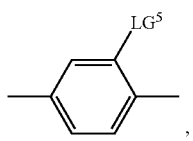
(ii-b)

$G^3$ is cyano or the following formula

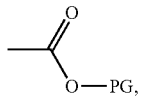

and the other symbols are the same as defined above,
can be prepared according to the following Scheme A, B, C, or D.

Scheme A:

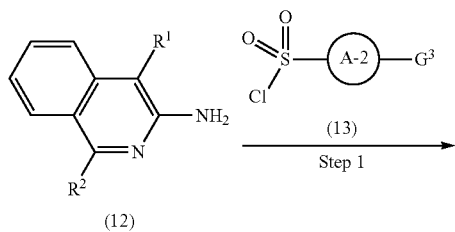

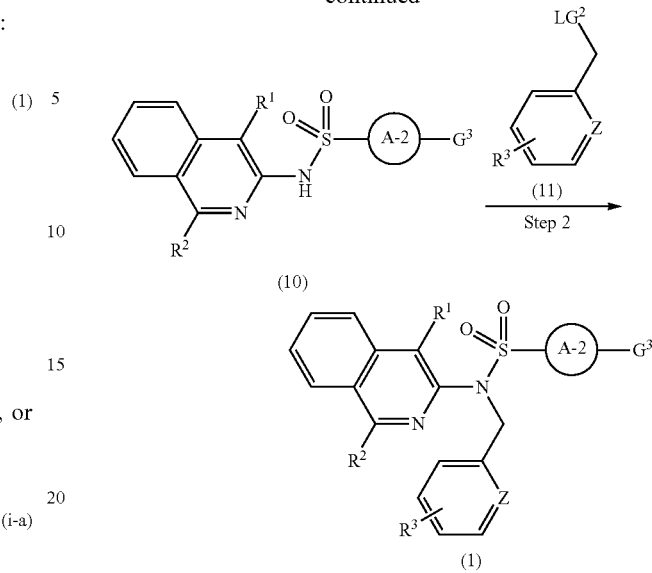

[In the above Scheme, $LG^2$ is a leaving group, for example, a halogen such as chlorine or bromine; and a substituted sulfonyloxy such as p-toluenesulfonyloxy, methanesulfonyloxy, or trifluoromethanesulfonyloxy, and the other symbols are the same as defined above.]

The compound of the formula (10) can be obtained by reacting the compound of the formula (12) with the compound of the formula (13). The target compound of the formula (1) can be prepared by reacting the compound of the formula (10) with the compound of the formula (11).

Step 1:

The reaction of the compound (12) with the compound (13) can be carried out in a solvent, and in the presence of a base.

Examples of the base include an alkali metal amide such as lithium diisopropylamide, sodium amide, or lithium bis(trimethylsilyl)amide; an alkali metal carbonate such as sodium carbonate, potassium carbonate, sodium hydrogen carbonate, or potassium hydrogen carbonate; an alkali metal phosphate such as sodium phosphate or potassium phosphate; an amine such as triethylamine, diisopropylethylamine, pyridine, or N-methylmorpholine, preferably an amine such as pyridine. Any solvent which does not affect the reaction may be preferably used as the solvent, and examples of the solvent include an ether such as tetrahydrofuran, 1,4-dioxane, or 1,2-dimethoxyethane; a hydrocarbon such as hexane, toluene, or xylene; a halogenohydrocarbon such as dichloromethane, chloroform, or 1,2-dichloroethane; an ester such as ethyl acetate or butyl acetate; a ketone such as acetone or butanone; an amide such as N,N-dimethylformamide, N,N-dimethylacetamide, 1,3-dimethyl-2-imidazolidinone, or N-methylpyrrolidone; a sulfoxide such as dimethylsulfoxide; and the above-mentioned amine such as pyridine; and a mixed solvent thereof. Preferable solvent in the present reaction is an amine such as pyridine and/or a halogenohydrocarbon such as chloroform. The reaction may be preferably carried out at 0° C. to 120° C.

In case a sulfonimide compound wherein two equivalents of the compound (13) are condensed with one equivalent of the compound (12) is obtained in said reaction, the corresponding compound (10) can be obtained by treating said sulfonimide compound with tetrabutylammonium fluoride.

Step 2: The reaction of the compound (10) with the compound (11) can be carried out in a solvent, and in the presence of a base.

Examples of the base include an alkali metal amide such as lithium diisopropylamide, sodium amide, or lithium bis(trimethylsilyl)amide; an alkali metal carbonate such as sodium carbonate, potassium carbonate, cesium carbonate, sodium hydrogen carbonate, or potassium hydrogen carbonate; an alkali metal phosphate such as sodium phosphate or potassium phosphate; and an amine such as triethylamine, diisopropylethylamine, pyridine, or N-methylmorpholine, preferably an alkali metal carbonate such as potassium carbonate. Any solvent which does not affect the reaction may be preferably used as the solvent, and examples of the solvent include an ether such as tetrahydrofuran, 1,4-dioxane, or 1,2-dimethoxyethane; a hydrocarbon such as toluene, hexane, or xylene; an ester such as ethyl acetate or butyl acetate; a ketone such as acetone or butanone; an amide such as N,N-dimethylformamide, N,N-dimethylacetamide, 1,3-dimethyl-2-imidazolidinone, or N-methylpyrrolidone; a sulfoxide such as dimethylsulfoxide; and the above-mentioned amine such as pyridine; and a mixed solvent thereof. Preferable solvent in the present reaction is an amide such as N,N-dimethylformamide. The reaction may be preferably carried out at −20° C. to 80° C.

Step 1:
The reaction of the compound (12) with the compound (13) can be carried out in a similar manner to the reaction of the compound (12) with the compound (13) in the above Scheme A.

Step 2:
The reaction of the compound (10) with the compound (14) can be carried out in a solvent, and in the presence of a phosphine and an azodicarboxylic acid compound.

Examples of the phosphine include triphenylphosphine, diphenyl(2-pyridyl)phosphine, (4-dimethylaminophenyl)diphenylphosphine, isopropyldiphenylphosphine, diethylphenylphosphine, dicyclohexylphenylphosphine, tributylphosphine, tri-t-butylphosphine, and tricyclohexylphosphine. Examples of the azodicarboxylic acid compound include diethylazodicarboxylate, diisopropylazodicarboxylate, dibutylazodicarboxylate, azodicarbonyl dipiperazine, and tetramethylazodicarboxamide. Alternatively, the reaction can be carried out in the presence of cyanomethylenetributylphosphorane in place of a phosphine and an azodicarboxylic acid compound. Any solvent which does not affect the reaction may be preferably used as the solvent, and examples of the solvent include an ether such as tetrahydrofuran, 1,4-dioxane, or 1,2-dimethoxyethane; a hydrocarbon such as toluene, hexane, or xylene; an ester such as ethyl acetate or butyl acetate; a ketone such as acetone or butanone; an amide such as N,N-dimethylformamide, N,N-dimethylacetamide, 1,3-dimethyl-2-imidazolidinone, or N-methylpyrrolidone; a sulfoxide such as dimethylsulfoxide; and a mixed solvent thereof. Preferable solvent in the present reaction is an ether such as tetrahydrofuran. The reaction may be preferably carried out at −20° C. to 120° C.

Scheme B:

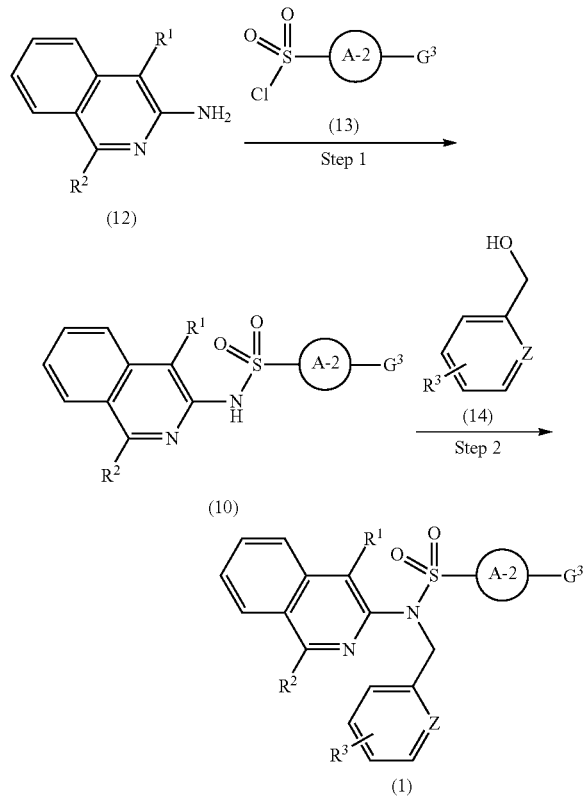

[In the above Scheme, the symbols are the same as defined above.]

The compound (10) can be obtained by reacting the compound (12) with the compound (13). The target compound of the formula (1) can be prepared by reacting the compound (10) with the compound (14).

Scheme C:

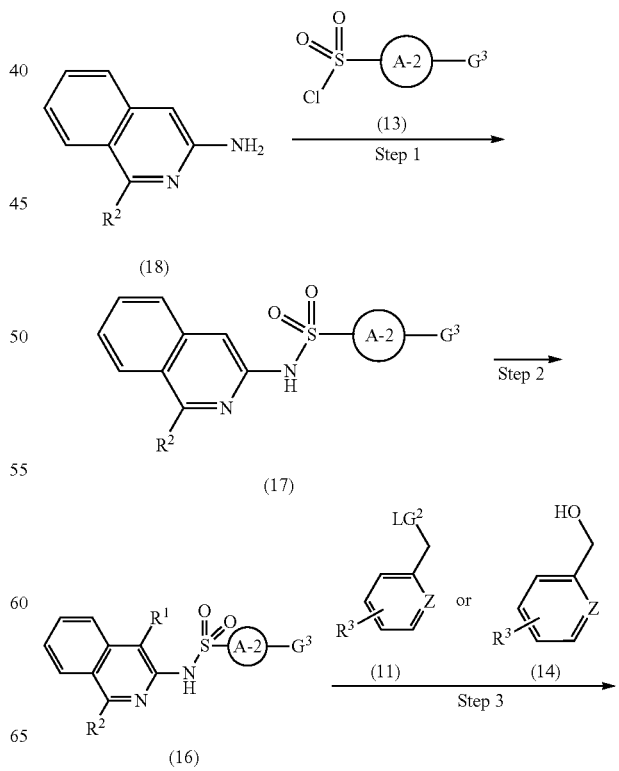

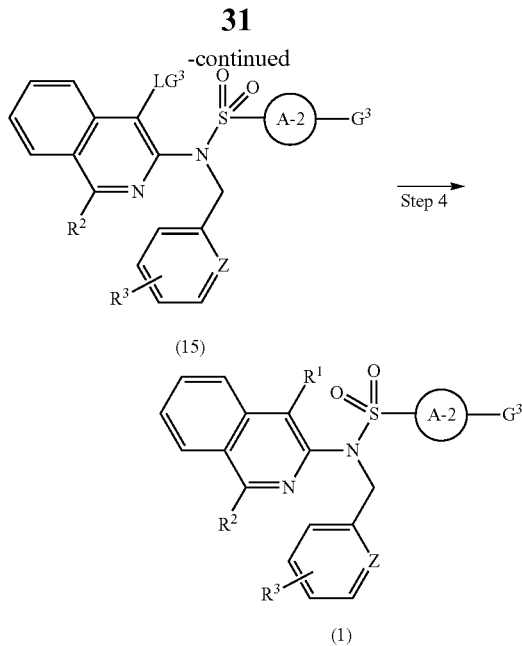

[In the above Scheme, LG$^3$ is a halogen such as bromine or iodine, and the other symbols are the same as defined above.]

The compound of the formula (17) can be obtained by reacting the compound of the formula (18) with the compound of the formula (13). The compound of the formula (16) can be obtained by introducing LG$^3$ to the compound of the formula (17). The compound of the formula (15) can be obtained by reacting the compound of the formula (16) with the compound of the formula (11) or the compound of the formula (14). The target compound of the formula (1) can be prepared by introducing R$^1$ to the compound of the formula (15).

Step 1:

The reaction of the compound (18) with the compound (13) can be carried out in a similar manner to the reaction of the compound (12) with the compound (13) in the above Scheme A.

Step 2:

The synthesis of the compound (16) wherein LG$^3$ is halogen can be carried out in a solvent (for example, an amide such as N,N-dimethylformamide), and in the presence of the corresponding N-halogenosuccinimide and an acid (for example, an alkylcarboxylic acid such as acetic acid). The reaction may be preferably carried out at 20° C. to 80° C.

Step 3:

The reaction of the compound (16) with the compound (11) can be carried out in a similar manner to the reaction of the compound (10) with the compound (11) in the above Scheme A.

Further, the reaction of the compound (16) with the compound (14) can be carried out in a similar manner to the reaction of the compound (10) with the compound (14) in the above Scheme B.

Step 4:

The reaction to obtain the compound (1) can be carried out by a suitable coupling reaction depending on R$^1$ to be introduced.

The compound (1) wherein R$^1$ is optionally substituted alkyl or optionally substituted cycloalkyl can be prepared by coupling the compound (15) with R$^1$B(OH)$_2$ or R$^1$BF$_3$K [wherein the symbol is the same as defined above].

The coupling reaction of the compound (15) with R$^1$B(OH)$_2$ or R$^1$BF$_3$K can be carried out in a solvent, with or without a ligand, and in the presence of a base and a palladium catalyst.

Examples of the base include an alkali metal carbonate such as cesium carbonate, potassium carbonate, sodium carbonate, or sodium hydrogen carbonate; an alkali metal phosphate such as tripotassium phosphate, trisodium phosphate, or disodium hydrogen phosphate; an amine such as N,N-diisopropylethylamine; an alkali metal fluoride such as cesium fluoride or potassium fluoride; and an alkali metal alkoxide such as sodium t-butoxide or potassium t-butoxide. Examples of the palladium catalyst include tetrakis(triphenylphosphine)palladium(0), palladium(II) acetate, bis(acetonitrile)dichloropalladium(II), dichlorobis(triphenylphosphine)palladium(II), a dichloromethane complex of [1,1'-bis(diphenylphosphino)ferrocene]dichloropalladium(II), a chloroform complex of tris(dibenzylidene-acetone)dipalladium(0), and palladium(II) chloride. Examples of the ligand include triphenylphosphine, tributylphosphine, tri-t-butylphosphine tetrafluoroborate, tricyclohexylphosphine, di(1-adamantyl)butylphosphine 1,3-bis(diphenylphosphino)propane, 2,2'-bis(diphenylphosphino)-1,1'-binaphthyl, and 1,1'-bis(diphenylphosphino)ferrocene. Any solvent which does not affect the reaction may be preferably used as the solvent, and examples of the solvent include an aromatic hydrocarbon such as toluene or xylene; an ether such as tetrahydrofuran, 1,2-dimethoxyethane, or 1,4-dioxane; an amide such as N,N-dimethylformamide, N,N-dimethylacetamide, 1,3-dimethyl-2-imidazolidinone, or N-methylpyrrolidone; an alcohol such as methanol, ethanol, or 2-propanol; water; and a mixed solvent thereof. The reaction may be preferably carried out at 20° C. to 150° C.

Alternatively, the compound (1) can be prepared by coupling the compound (15) with G$^4$B(OH)$_2$ or G$^4$BF$_3$K [wherein G$^4$ is the corresponding optionally substituted alkyl or optionally substituted cycloalkenyl.] to obtain an alkenyl compound or a cycloalkenyl compound, followed by hydrogenating the obtained compound.

The coupling reaction of the compound (15) with G$^4$B(OH)$_2$ or G$^4$BF$_3$K can be carried out in a similar manner to the coupling reaction of the above compound (15) with R$^1$B(OH)$_2$ or R$^1$BF$_3$K.

The hydrogenation reaction of the alkenyl compound or the cycloalkenyl compound can be carried out under hydrogen atmosphere, in a solvent, and in the presence of a metal catalyst.

Examples of the metal catalyst include palladium carbon, palladium hydroxide, or platinum oxide. Any solvent which does not affect the reaction may be preferably used as the solvent, and examples of the solvent include an ether such as tetrahydrofuran, 1,2-dimethoxyethane, or 1,4-dioxane; an alcohol such as methanol, ethanol, or 2-propanol; an ester such as ethyl acetate; a carboxylic acid such as acetic acid; and a mixed solvent thereof. The reaction may be preferably carried out at 20° C. to 80° C.

The compound (1) wherein R$^1$ is fluoroalkyl can be prepared by coupling the compound (15) with methyl fluorosulfonyldifluoroacetate, sodium fluoroalkylcarboxylate, potassium fluoroalkylcarboxylate, or fluoroalkyltrimethylsilane.

The coupling reaction can be carried out in a solvent, with or without an additive, and in the presence of a copper complex.

Examples of the copper complex include copper(I) bromide and copper(I) iodide. Examples of the additive include potassium fluoride. Any solvent which does not affect the reaction may be preferably used as the solvent, and examples of the solvent include an ether such as tetrahydrofuran, 1,4-dioxane, or 1,2-dimethoxyethane; an amide such as N,N-dimethylformamide, N,N-dimethylacetamide, 1,3-dimethyl-2-imidazolidinone, or N-methylpyrrolidone; an aprotic polar solvent such as dimethylsulfoxide or hexamethylphosphorictriamide; and a mixed solvent thereof. Preferably, an amide such as N,N-dimethylformamide and an aprotic polar solvent such as hexamethylphosphorictriamide are used in combination. The reaction may be preferably carried out at 20° C. to 120° C.

Scheme D:

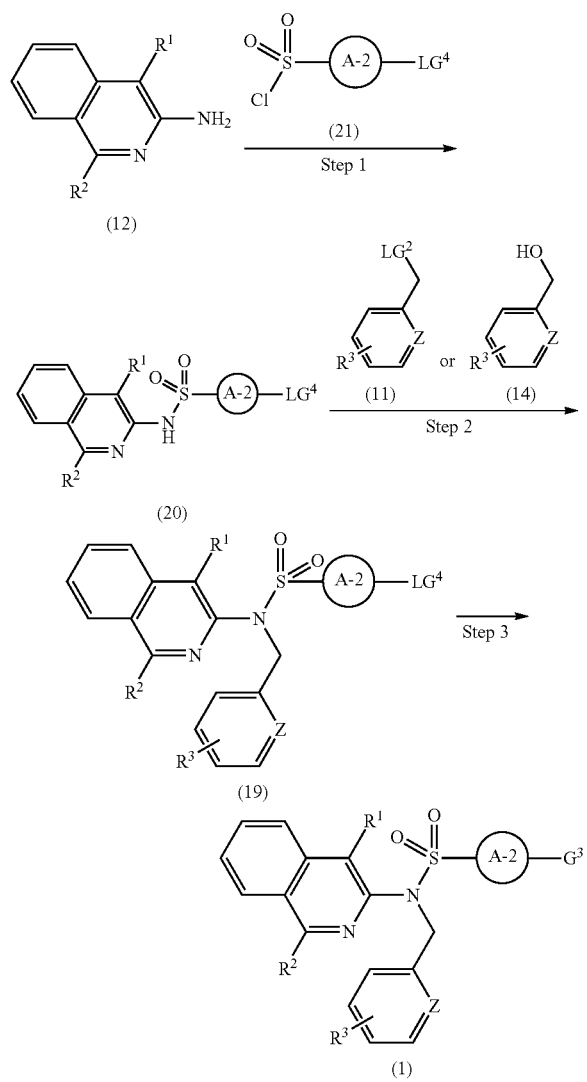

[In the above Scheme, $LG^4$ is a halogen such as chlorine, bromine, or iodine; or a substituted sulfonyloxy such as trifluoromethanesulfonyloxy, and the other symbols are the same as defined above.]

The compound of the formula (20) can be obtained by reacting the compound of the formula (12) with the compound of the formula (21). The compound of the formula (19) can be obtained by reacting the compound of the formula (20) with the compound of the formula (11) or the compound of the formula (14). The target compound of the formula (1) can be prepared by introducing $G^3$ to the compound of the formula (19).

Step 1:

The reaction of the compound (12) with the compound (21) can be carried out in a similar manner to the reaction of the compound (12) with the compound (13) in the above Scheme A.

Step 2:

The reaction of the compound (20) with the compound (11) can be carried out in a similar manner to the reaction of the compound (10) with the compound (11) in the above Scheme A.

Further, the reaction of the compound (20) with the compound (14) can be carried out in a similar manner to the reaction of the compound (10) with the compound (14) in the above Scheme B.

Step 3:

The reaction to obtain the compound (1) can be carried out by a suitable coupling reaction depending on $G^3$ to be introduced.

The compound (1) wherein $G^3$ is cyano can be prepared by cyanating the compound (19).

The cyanation reaction of the compound (19) can be carried out in a solvent, with or without a base and/or a ligand, and in the presence of a cyanating agent and a palladium catalyst.

Examples of the cyanating agent include zinc(II) cyanide, copper(I) cyanide, and potassium hexacyanoferrate(II). Examples of the palladium catalyst include tetrakis(triphenylphosphine)palladium(0) and palladium(II) acetate. Examples of the base include an alkali metal carbonate such as sodium carbonate. Examples of the ligand include triphenylphosphine and tri-o-tolylphosphine. Any solvent which does not affect the reaction may be preferably used as the solvent, and examples of the solvent include an amide such as N,N-dimethylformamide, N,N-dimethylacetamide, 1,3-dimethyl-2-imidazolidinone, or N-methylpyrrolidone. The reaction may be preferably carried out at 60° C. to 200° C.

The compound (1) wherein $G^3$ is the following formula:

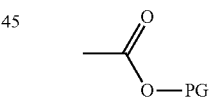

[wherein the symbol is the same as defined above.]

can be prepared by esterifying the compound (19).

The esterification reaction of the compound (19) can be carried out in a solvent, with or without a ligand, and in the presence of a carbon monoxide source, the corresponding alcohol (PG-OH), a base, and a palladium catalyst.

Examples of the carbon monoxide source include carbon monoxide gas and molybdenum hexacarbonyl. Examples of the base include an amine such as triethylamine, diisopropylethylamine, pyridine, N-methylmorpholine, or 1,8-diazabicyclo[5.4.0]undec-7-ene; an alkali metal salt of alkylcarboxylic acid such as sodium acetate or potassium acetate, preferably an amine such as triethylamine or 1,8-diazabicyclo[5.4.0]undec-7-ene. Examples of the palladium catalyst include tetrakis(triphenylphosphine)palladium(0), palladium(II) acetate, a dichloromethane complex of [1,1'-bis(diphenylphosphino)ferrocene]dichloropalladium(II), trans-di(μ-acetato)bis[o-(di-o-tolylphosphino)benzyl]dipalladium (II), [2,2'-bis(diphenylphosphino)-1,1'-binaphthyl]dichloropalladium(II), [1,3-bis(diphenylphosphino)propane]dichloropalladium(II), preferably palladium(II) acetate or trans-di(μ-acetato)bis[o-(di-o-tolylphosphino)benzyl]dipalladium(II). Examples of the ligand include triphenylphosphine, tributylphosphine, tri-t-butylphosphine tetrafluoroborate, 1,3-bis(diphenylphosphino)propane, 2,2'-bis(diphenylphosphino)-1,1'-binaphthyl, and 1,1'-bis(diphenylphosphino)ferrocene, preferably tributylphosphine, tri-t-butylphosphine tetrafluoroborate, or 1,1'-bis(diphenylphosphino)ferrocene. Any solvent which does not affect the reaction may be preferably used as the solvent, and examples of the solvent include an aromatic hydrocarbon such as toluene or xylene; an amide such as N,N-dimethylformamide, N,N-dimethylacetamide, 1,3-dimethyl-2-imidazolidinone, or N-methylpyrrolidone; an alkylnitrile such as acetonitrile or propionitrile; and the above-mentioned corresponding alcohol (PG-OH); and a mixed solvent thereof. Preferable solvent in the present reaction is a mixed solvent of an alkylnitrile such as acetonitrile and the corresponding alcohol (PG-OH) or a mixed solvent of an amide such as N,N-dimethylacetamide and the corresponding alcohol (PG-OH). The reaction may be preferably carried out at 60° C. to 160° C.

The compound of the formula (1-a) of the present invention, for example, can be converted from the compound of the formula (1-b) according to the following Scheme E.

Scheme E:

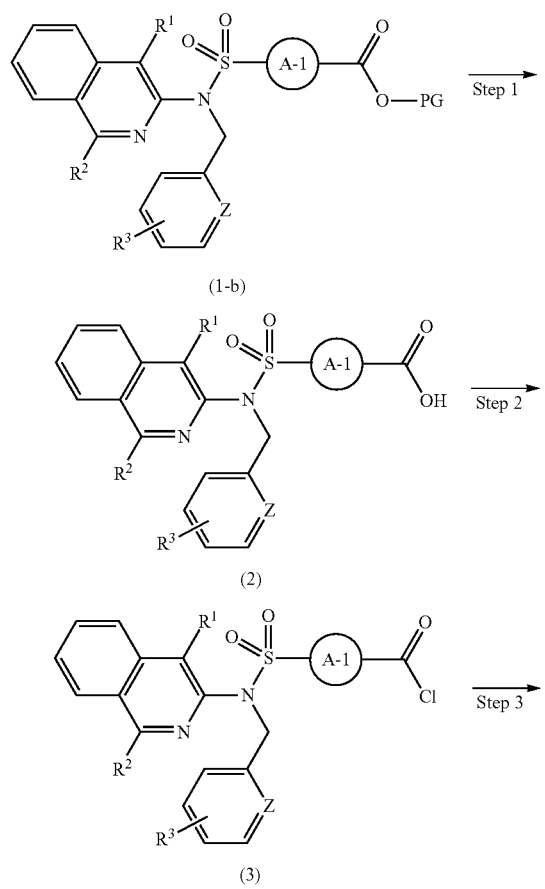

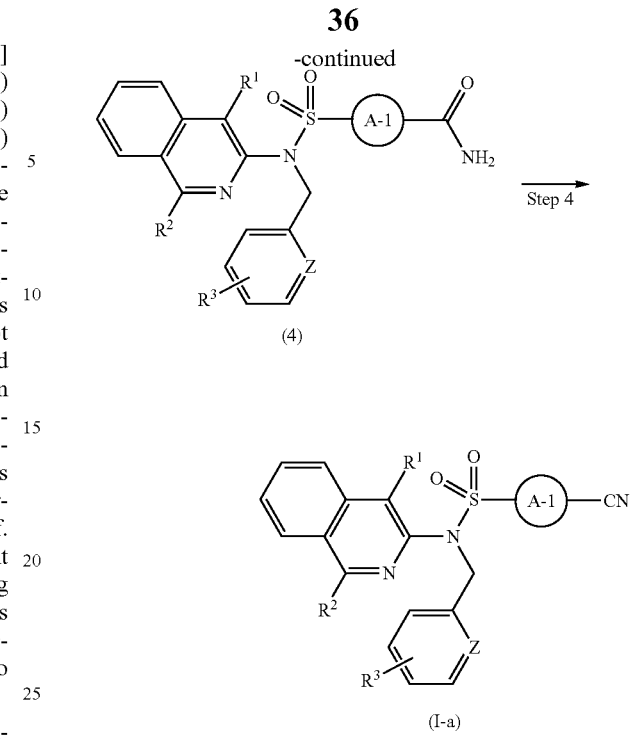

[In the above Scheme, the symbols are the same as defined above.]

The compound of the formula (2) can be obtained by hydrolyzing the compound of the formula (1-b). The compound (3) can be obtained by acid-chloridizing the compound of the formula (2) or a salt thereof. The compound of the formula (4) can be obtained by amidating the compound (3). The target compound of the formula (1-a) can be prepared by dehydrating the compound of the formula (4).

Step 1:

The hydrolysis reaction of the compound (1-b) wherein PG is alkyl can be carried out in a similar manner to the hydrolysis reaction of the compound (1-b) in the above Scheme II.

Step 2:

The chlorination reaction of the compound (2) or a salt thereof can be carried out in a similar manner to the chlorination reaction of the compound (2) or a salt thereof in the above Scheme II.

Step 3:

The amidation reaction of the compound (3) can be carried out in a similar manner to the amidation reaction of the compound (3) in the above Scheme III.

Step 4:

The dehydration reaction of the compound (4) can be carried out in a solvent (for example, a halogenohydrocarbon such as dichloromethane, or the following phosphorus oxychloride), with or without a base (for example, an amine such as triethylamine or pyridine), in the presence of a carboxylic acid anhydride such as trifluoroacetic acid anhydride or phosphorus oxychloride. The reaction may be preferably carried out at 0° C. to 100° C.

The intermediate compound (22) of the present invention can be prepared according to the following Scheme F, G, H, J, or K.

Scheme F:

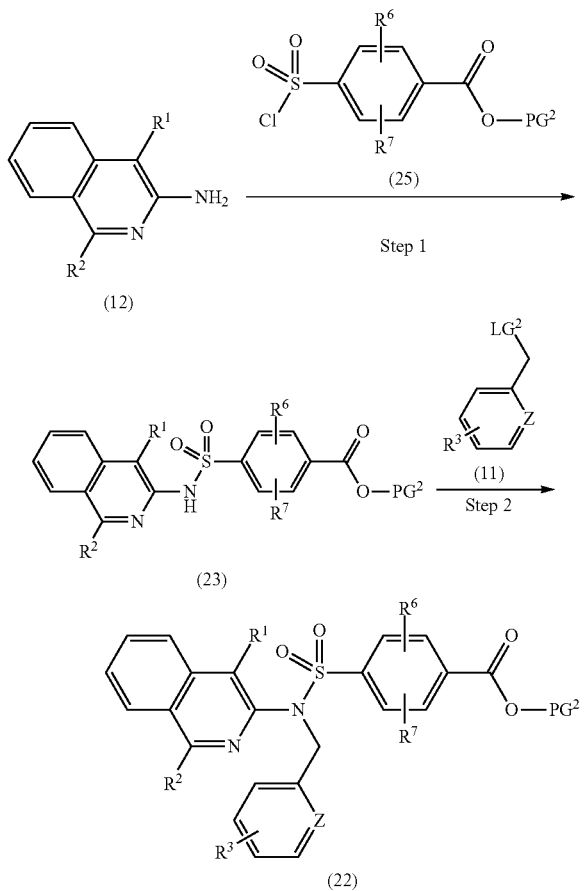

[In the above Scheme, the symbols are the same as defined above.]

The compound of the formula (23) can be obtained by reacting the compound of the formula (12) with the compound of the formula (25). The target compound of the formula (22) can be prepared by reacting the compound of the formula (23) with the compound of the formula (11).

Step 1:

The reaction of the compound (12) with the compound (25) can be carried out in a solvent, and in the presence of a base.

Examples of the base include an alkali metal amide such as lithium diisopropylamide, sodium amide, or lithium bis(trimethylsilyl)amide; an alkali metal carbonate such as sodium carbonate, potassium carbonate, sodium hydrogen carbonate, or potassium hydrogen carbonate; an alkali metal phosphate such as sodium phosphate or potassium phosphate; and an amine such as triethylamine, diisopropylethylamine, pyridine, or N-methylmorpholine, preferably an amine such as pyridine. Any solvent which does not affect the reaction may be preferably used as the solvent, and examples of the solvent include an ether such as tetrahydrofuran, 1,4-dioxane, or 1,2-dimethoxyethane; a hydrocarbon such as hexane, toluene, or xylene; a halogenohydrocarbon such as dichloromethane, chloroform, or 1,2-dichloroethane; an ester such as ethyl acetate or butyl acetate; a ketone such as acetone or butanone; an amide such as N,N-dimethylformamide, N,N-dimethylacetamide, 1,3-dimethyl-2-imidazolidinone, or N-methylpyrrolidone; a sulfoxide such as dimethylsulfoxide; and the above-mentioned amine such as pyridine; and a mixed solvent thereof. Preferable solvent in the present reaction is an amine such as pyridine, and/or a halogenohydrocarbon such as chloroform. The reaction may be preferably carried out at 0° C. to 120° C.

In case a sulfonimide compound wherein two equivalents of the compound (25) are condensed with one equivalent of the compound (12) is obtained in said reaction, the corresponding compound (23) can be obtained by treating said sulfonimide compound with tetrabutylammonium fluoride.

Step 2:

The reaction of the compound (23) with the compound (11) can be carried out in a solvent, and in the presence of a base.

Examples of the base include an alkali metal amide such as lithium diisopropylamide, sodium amide, or lithium bis(trimethylsilyl)amide; an alkali metal carbonate such as sodium carbonate, potassium carbonate, cesium carbonate, sodium hydrogen carbonate, or potassium hydrogen carbonate; an alkali metal phosphate such as sodium phosphate or potassium phosphate; and an amine such as triethylamine, diisopropylethylamine, pyridine, or N-methylmorpholine, preferably an alkali metal carbonate such as potassium carbonate. Any solvent which does not affect the reaction may be preferably used as the solvent, and examples of the solvent include an ether such as tetrahydrofuran, 1,4-dioxane, or 1,2-dimethoxyethane; a hydrocarbon such as toluene, hexane, or xylene; an ester such as ethyl acetate or butyl acetate; a ketone such as acetone or butanone; an amide such as N,N-dimethylformamide, N,N-dimethylacetamide, 1,3-dimethyl-2-imidazolidinone, or N-methylpyrrolidone; a sulfoxide such as dimethylsulfoxide; and the above-mentioned amine such as pyridine; and a mixed solvent thereof. Preferable solvent in the present reaction is an amide such as N,N-dimethylformamide. The reaction may be preferably carried out at −20° C. to 80° C.

Scheme G:

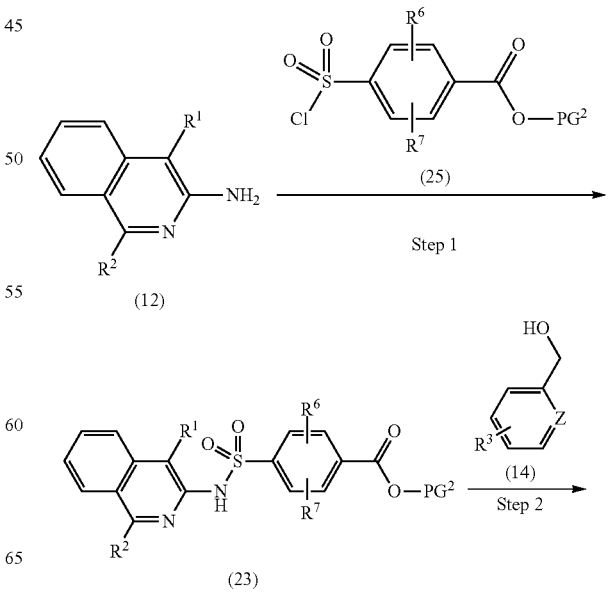

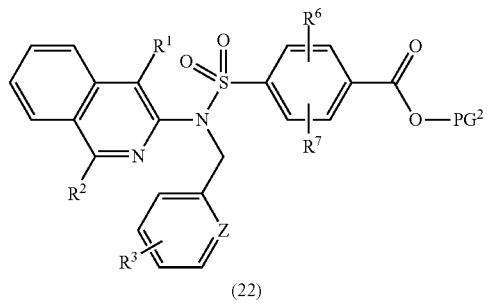

[In the above Scheme, the symbols are the same as defined above.]

The compound (23) can be obtained by reacting the compound (12) with the compound (25). The target compound of the formula (22) can be prepared by reacting the compound (23) with the compound (14).

Step 1:

The reaction of the compound (12) with the compound (25) can be carried out in a similar manner to the reaction of the compound (12) with the compound (25) in the above Scheme F.

Step 2:

The reaction of the compound (23) with the compound (14) can be carried out in a solvent, and in the presence of a phosphine and an azodicarboxylic acid compound.

Examples of the phosphine include triphenylphosphine, diphenyl(2-pyridyl)phosphine, (4-dimethylaminophenyl)diphenylphosphine, isopropyldiphenylphosphine, diethylphenylphosphine, dicyclohexylphenylphosphine, tributylphosphine, tri-t-butylphosphine, and tricyclohexylphosphine. Examples of the azodicarboxylic acid compound include diethylazodicarboxylate, diisopropylazodicarboxylate, dibutylazodicarboxylate, azodicarbonyl dipiperazine, and tetramethylazodicarboxamide. Alternatively, the reaction can be carried out in the presence of cyanomethylenetributylphosphorane in place of a phosphine and an azodicarboxylic acid compound. Any solvent which does not affect the reaction may be preferably used as the solvent, and examples of the solvent include an ether such as tetrahydrofuran, 1,4-dioxane, or 1,2-dimethoxyethane; a hydrocarbon such as toluene, hexane, or xylene; an ester such as ethyl acetate or butyl acetate; a ketone such as acetone or butanone; an amide such as N,N-dimethylformamide, N,N-dimethylacetamide, 1,3-dimethyl-2-imidazolidinone, or N-methylpyrrolidone; a sulfoxide such as dimethylsulfoxide; and a mixed solvent thereof. Preferable solvent in the present reaction is an ether such as tetrahydrofuran. The reaction may be preferably carried out at −20° C. to 120° C.

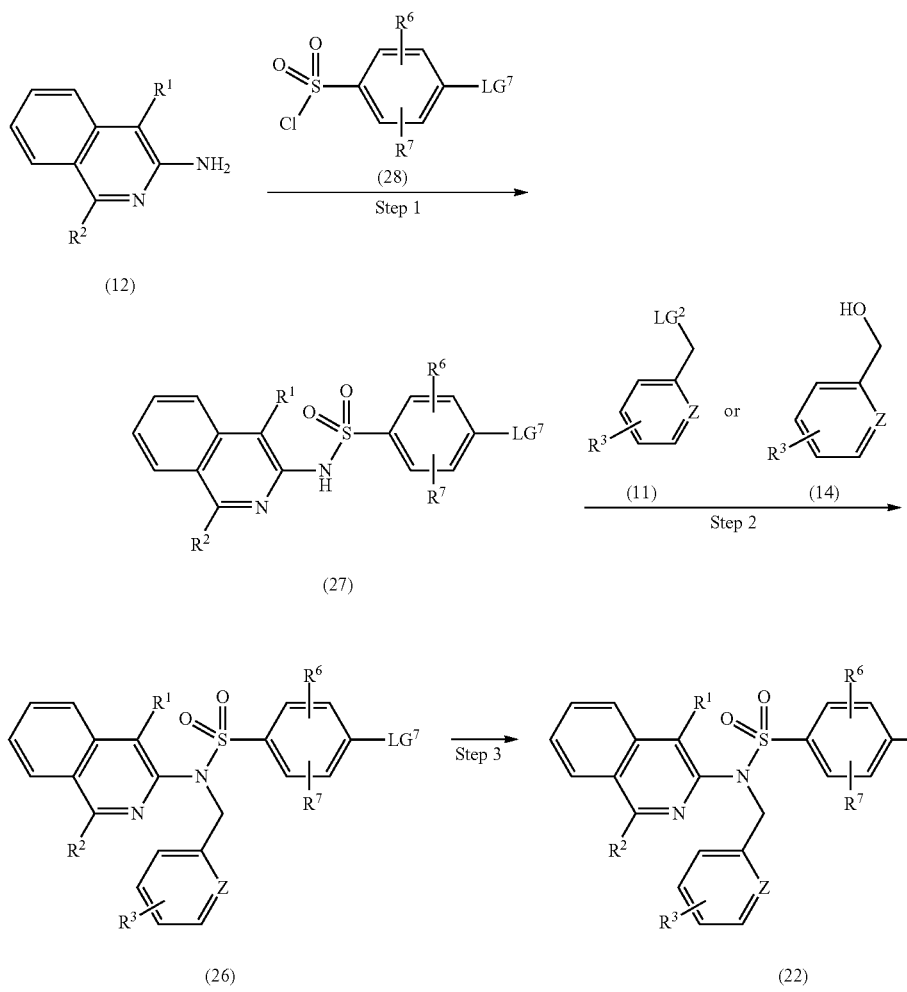

[In the above Scheme, $LG^7$ is a halogen such as bromine or iodine; or a substituted sulfonyloxy such as trifluoromethanesulfonyloxy, and the other symbols are the same as defined above.]

The compound (27) can be obtained by reacting the compound (12) with the compound (28). The compound (26) can be obtained by reacting the compound (27) with the compound (11) or the compound (14). The target compound of the formula (22) can be prepared by converting $LG^7$ in the compound (26).

Step 1:
The reaction of the compound (12) with the compound (28) can be carried out in a similar manner to the reaction of the compound (12) with the compound (25) in the above Scheme F.

Step 2:
The reaction of the compound (27) with the compound (11) can be carried out in a similar manner to the reaction of the compound (23) with the compound (11) in the above Scheme F.

Further, the reaction of the compound (27) with the compound (14) can be carried out in a similar manner to the reaction of the compound (23) with the compound (14) in the above Scheme G.

Step 3:
The conversion of $LG^7$ in the compound (26) can be carried out in a solvent, with or without a ligand, and in the presence of a carbon monoxide source, the corresponding alcohol ($PG^2$-OH), a base, and a palladium catalyst.

Examples of the carbon monoxide source include carbon monoxide gas and molybdenum hexacarbonyl. Examples of the base include an amine such as triethylamine, diisopropylethylamine, pyridine, N-methylmorpholine, or 1,8-diazabicyclo[5.4.0]undec-7-ene; an alkali metal salt of alkylcarboxylic acid such as sodium acetate or potassium acetate, preferably an amine such as triethylamine or 1,8-diazabicyclo[5.4.0]undec-7-ene. Examples of the palladium catalyst include tetrakis(triphenylphosphine)palladium(0), palladium(II) acetate, a dichloromethane complex of [1,1'-bis(diphenylphosphino)ferrocene]dichloropalladium(II), trans-di(μ-acetato)bis[o-(di-o-tolylphosphino)benzyl]dipalladium (II), [2,2'-bis(diphenylphosphino)-1,1'-binaphthyl]dichloropalladium(II), and [1,3-bis(diphenylphosphino)propane]dichloropalladium(II), preferably palladium(II) acetate or trans-di(μ-acetato)bis[o-(di-o-tolylphosphino)benzyl]dipalladium(II). Examples of the ligand include triphenylphosphine, tributylphosphine, tri-t-butylphosphine tetrafluoroborate, 1,3-bis(diphenylphosphino)propane, 2,2'-bis(diphenylphosphino)-1,1'-binaphthyl, and 1,1'-bis(diphenylphosphino)ferrocene, preferably tributylphosphine, tri-t-butylphosphine tetrafluoroborate, or 1,1'-bis(diphenylphosphino)ferrocene. Any solvent which does not affect the reaction may be preferably used as the solvent, and examples of the solvent include an aromatic hydrocarbon such as toluene or xylene; an amide such as N,N-dimethylformamide, N,N-dimethylacetamide, 1,3-dimethyl-2-imidazolidinone, or N-methylpyrrolidone; an alkylnitrile such as acetonitrile or propionitrile; and the above-mentioned the corresponding alcohol ($PG^2$-OH); and a mixed solvent thereof. Preferable solvent in the present reaction is a mixed solvent of an alkylnitrile such as acetonitrile and the corresponding alcohol ($PG^2$-OH), or a mixed solvent of an amide such as N,N-dimethylacetamide and the corresponding alcohol ($PG^2$-OH). The reaction may be preferably carried out at 60° C. to 160° C.

Among the intermediate compound (22) of the present invention, a compound of the formula (22-a):

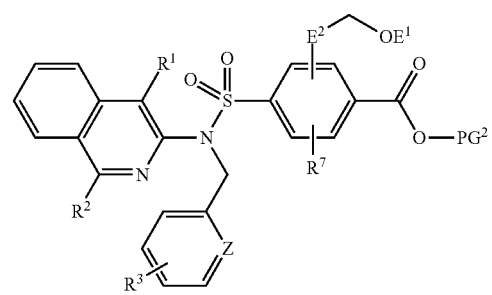

(22-a)

wherein $E^1$ is alkyl, $E^2$ is a bond, or straight or branched-chain $C_1$-$C_5$ alkylene, and the other symbols are the same as defined above,
can be prepared according to, for example, the following Scheme J.

Scheme J:

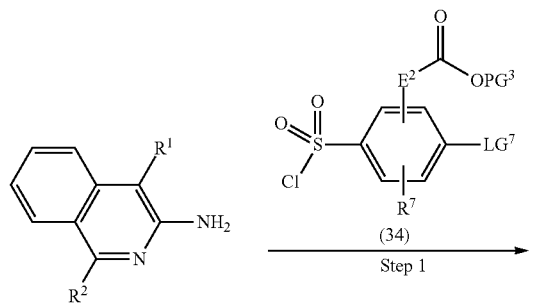

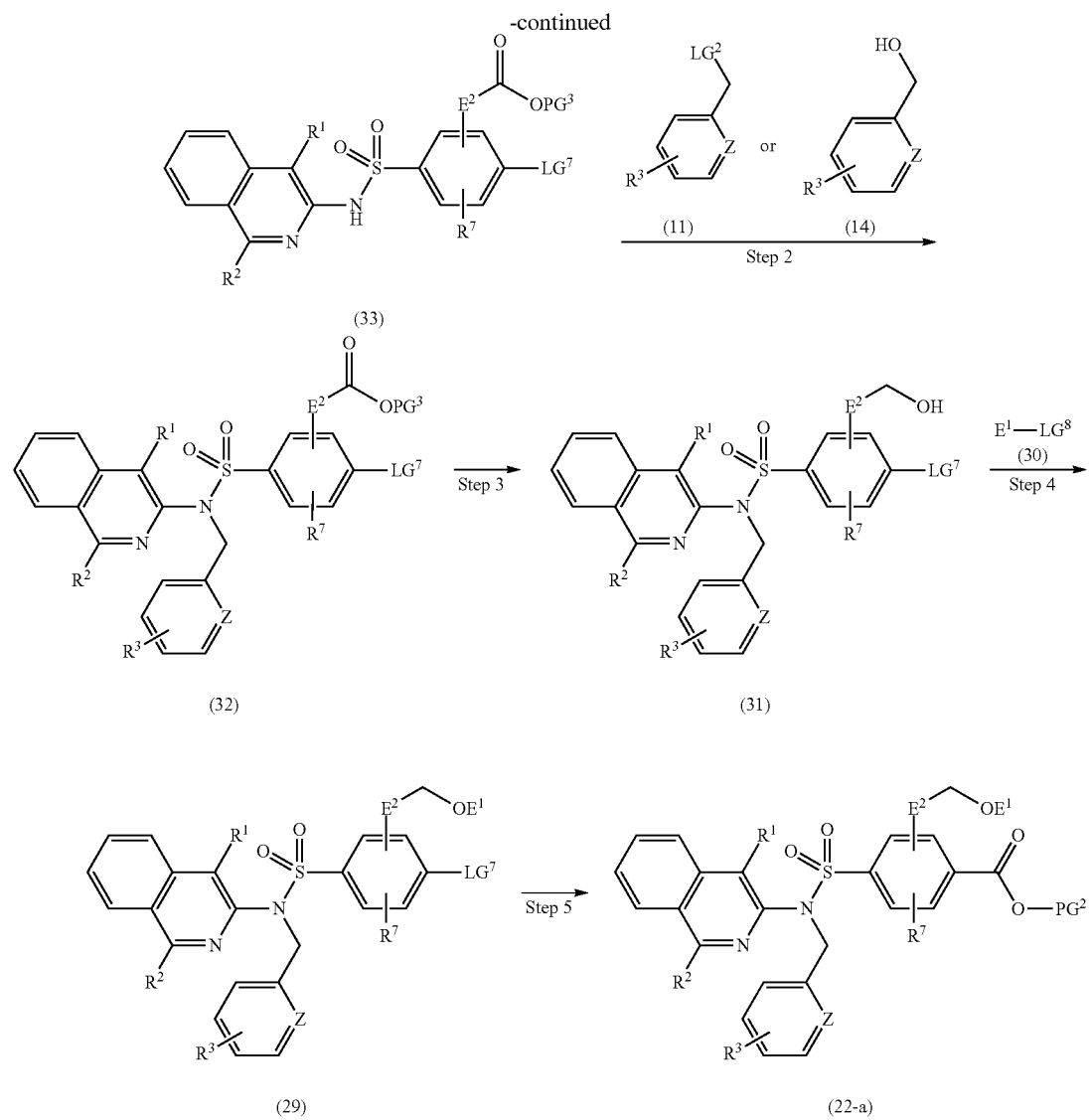

[In the above Scheme, PG³ is a carboxylic acid protecting group such as alkyl, LG⁸ is a leaving group such as a halogen, e.g., bromine or iodine; or a substituted sulfonyloxy such as trifluoromethanesulfonyloxy, and the other symbols are the same as defined above.]

The compound (33) can be obtained by reacting the compound (12) with the compound (34). The compound (32) can be obtained by reacting the compound (33) with the compound (11) or the compound (14). The compound (31) can be obtained by reducing the compound (32). The compound (29) can be obtained by reacting the compound (31) with the compound (30). The target compound of the formula (22-a) can be prepared by converting LG⁷ in the compound (29).

Step 1:
The reaction of the compound (12) with the compound (34) can be carried out in a similar manner to the reaction of the compound (12) with the compound (25) in the above Scheme F.

Step 2:
The reaction of the compound (33) with the compound (11) can be carried out in a similar manner to the reaction of the compound (23) with the compound (11) in the above Scheme F.

Further, the reaction of the compound (33) with the compound (14) can be carried out in a similar manner to the reaction of the compound (23) with the compound (14) in the above Scheme G.

Step 3:
The reduction reaction of the compound (32) can be carried out in a solvent, and in the presence of a reducing agent.

Examples of the reducing agent include lithium borohydride, sodium borohydride, lithium aluminum hydride, and diisobutylaluminum hydride, preferably diisobutylaluminum hydride. Any solvent which does not affect the reaction may be preferably used as the solvent, and examples of the solvent include an aromatic hydrocarbon such as toluene or xylene; a halogenohydrocarbon such as dichloromethane or chloroform; an ether such as tetrahydrofuran or diethylether; an alcohol such as methanol or ethanol; and a mixed solvent thereof. The reaction may be preferably carried out at −80° C. to 120° C.

Step 4:

The reaction of the compound (31) with the compound (30) can be carried out in a solvent, and in the presence of a base.

Examples of the base include an alkali metal hydride such as sodium hydride or potassium hydride; an alkali metal alkoxide such as potassium t-butoxide; and an alkali metal amide such as lithium diisopropylamide, sodium amide, or lithium bis(trimethylsilyl)amide, preferably an alkali metal hydride such as sodium hydride. Any solvent which does not affect the reaction may be preferably used as the solvent, and examples of the solvent include an ether such as tetrahydrofuran, 1,4-dioxane, or 1,2-dimethoxyethane; a hydrocarbon such as toluene, hexane, or xylene; an ester such as ethyl acetate or butyl acetate; an amide such as N,N-dimethylformamide, N,N-dimethylacetamide, 1,3-dimethyl-2-imidazolidinone, or N-methylpyrrolidone; and a mixed solvent thereof. The reaction may be preferably carried out at 0° C. to 80° C.

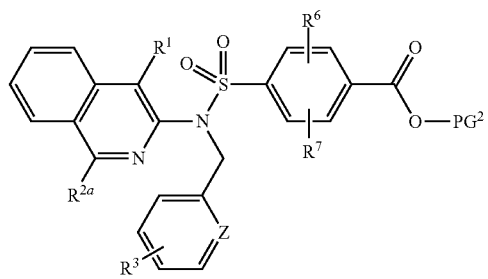

(22-b)

wherein $R^{2a}$ is optionally substituted cycloalkyl, and the other symbols are the same as defined above, can be prepared according to, for example, the following Scheme K.

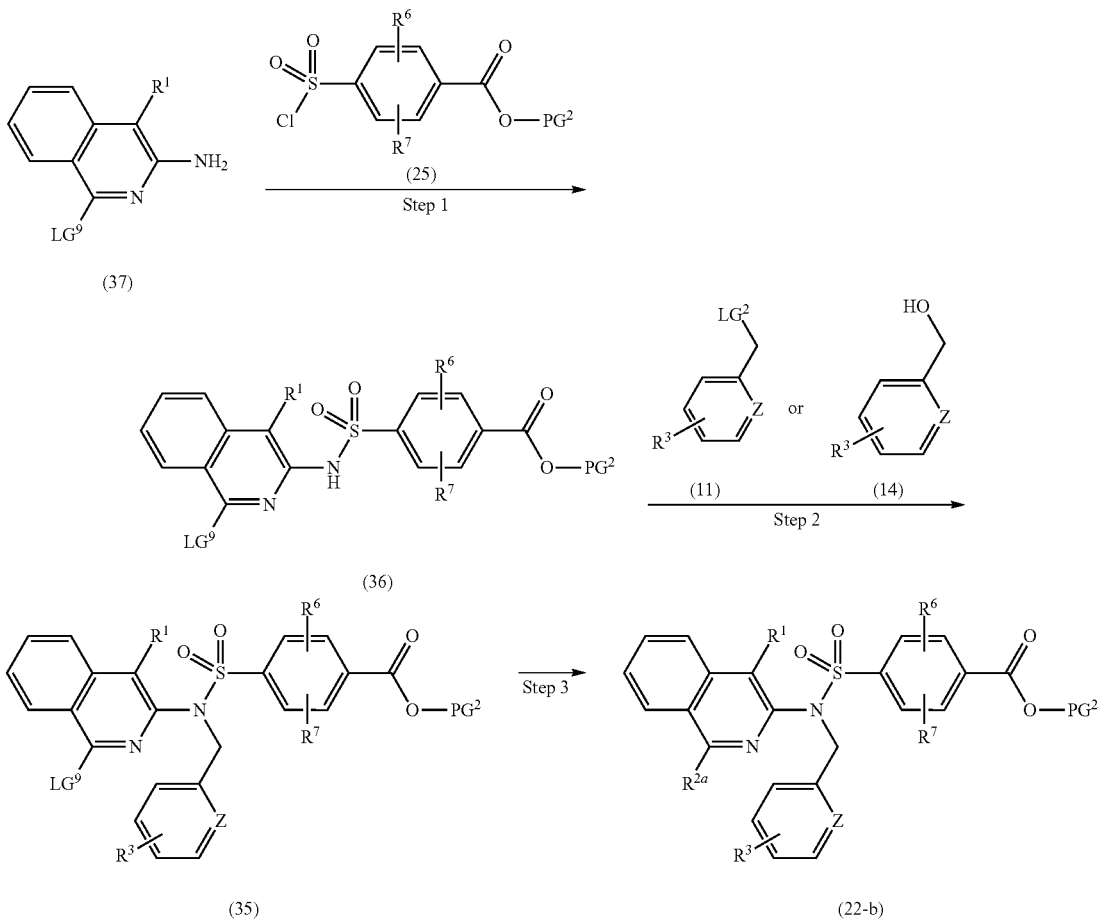

Step 5:

The conversion reaction of $LG^7$ in the compound (29) can be carried out in a similar manner to the conversion reaction of $LG^7$ in the compound (26) in the above Scheme H.

Among the intermediate compound (22) of the present invention, a compound of the formula (22-b):

[In the above Scheme, $LG^9$ is a leaving group such as a halogen, e.g., bromine or iodine; a substituted sulfonyloxy such as trifluoromethanesulfonyloxy, and the other symbols are the same as defined above.]

The compound (36) can be obtained by reacting the compound (37) with the compound (25). The compound (35) can be obtained by reacting the compound (36) with the compound (11) or the compound (14). The target compound of the formula (22-b) can be prepared by introducing an optionally substituted cycloalkyl to the compound (35).

Step 1:

The reaction of the compound (37) with the compound (25) can be carried out in a similar manner to the reaction of the compound (12) with the compound (25) in the above Scheme F.

Step 2:

The reaction of the compound (36) with the compound (11) can be carried out in a similar manner to the reaction of the compound (23) with the compound (11) in the above Scheme F.

Further, the reaction of the compound (36) with the compound (14) can be carried out in a similar manner to the reaction of the compound (23) with the compound (14) in the above Scheme G.

Step 3:

The compound (22-b) can be prepared by coupling the compound (35) with $R^{2a}B(OH)_2$ or $R^{2a}BF_3K$ [wherein the symbol is the same as defined above].

The coupling reaction of the compound (35) with $R^{2a}B(OH)_2$ or $R^{2a}BF_3K$ can be carried out in a solvent, with or without a ligand, and in the presence of a base and a palladium catalyst.

Examples of the base include an alkali metal carbonate such as cesium carbonate, potassium carbonate, sodium carbonate, or sodium hydrogen carbonate; an alkali metal phosphate such as tripotassium phosphate, trisodium phosphate, or disodium hydrogen phosphate; an amine such as N,N-diisopropylethylamine; an alkali metal fluoride such as cesium fluoride or potassium fluoride; and an alkali metal alkoxide such as sodium t-butoxide or potassium t-butoxide. Examples of the palladium catalyst include tetrakis(triphenylphosphine)palladium(0), palladium(II) acetate, bis(acetonitrile)dichloropalladium(II), dichlorobis(triphenylphosphine)palladium(II), a dichloromethane complex of [1,1'-bis(diphenylphosphino)ferrocene]dichloropalladium(II), a chloroform complex of tris(dibenzylidene-acetone)dipalladium(0), and palladium(II) chloride. Examples of the ligand include triphenylphosphine, tributylphosphine, tri-t-butylphosphine tetrafluoroborate, tricyclohexylphosphine, di(1-adamantyl)butylphosphine 1,3-bis(diphenylphosphino)propane, 2,2'-bis(diphenylphosphino)-1,1'-binaphthyl, and 1,1'-bis(diphenylphosphino)ferrocene. Any solvent which does not affect the reaction may be preferably used as the solvent, and examples of the solvent include an aromatic hydrocarbon such as toluene or xylene; an ether such as tetrahydrofuran, 1,2-dimethoxyethane, or 1,4-dioxane; an amide such as N,N-dimethylformamide, N,N-dimethylacetamide, 1,3-dimethyl-2-imidazolidinone, or N-methylpyrrolidone; an alcohol such as methanol, ethanol, or 2-propanol; water; and a mixed solvent thereof. The reaction may be preferably carried out at 20° C. to 150° C.

Alternatively, the compound (22-b) can be prepared by coupling the compound (35) with $E^3B(OH)_2$ or $E^3BF_3K$ [wherein $E^3$ is the corresponding optionally substituted cycloalkenyl] to obtain an cycloalkenyl compound, followed by hydrogenating the obtained compound.

The coupling reaction of the compound (35) with $E^3B(OH)_2$ or $E^3BF_3K$ can be carried out in a similar manner to the above coupling reaction of the compound (35) with $R^{2a}B(OH)_2$ or $R^{2a}BF_3K$.

The hydrogenation reaction of the cycloalkenyl compound can be carried out under hydrogen atmosphere, in a solvent, and in the presence of a metal catalyst.

Examples of the metal catalyst include palladium carbon, palladium hydroxide, and platinum oxide. Any solvent which does not affect the reaction may be preferably used as the solvent, and examples of the solvent include an ether such as tetrahydrofuran, 1,2-dimethoxyethane, or 1,4-dioxane; an alcohol such as methanol, ethanol, or 2-propanol; an ester such as ethyl acetate; a carboxylic acid such as acetic acid; and a mixed solvent thereof. The reaction may be preferably carried out at 20° C. to 80° C., and a hydrogen pressure of 0.1 MPa to 3 MPa.

Further, an interconversion may be carried out to the intermediate compound (22) synthesized by the above process, or a precursor compound in the synthetic route of the compound (22) by a conventional method.

The compound (22) wherein $R^6$ is optionally substituted cycloalkyl and a precursor compound thereof can be prepared by coupling the corresponding compound (22) wherein $R^6$ is halogen (particularly, bromine or iodine) and a precursor compound thereof, respectively, with $R^{6a}B(OH)_2$ or $R^{6a}BF_3K$ [wherein $R^{6a}$ is optionally substituted cycloalkyl].

The coupling reaction of the compound wherein $R^6$ is halogen with $R^{6a}B(OH)_2$ or $R^{6a}BF_3K$ can be carried out in a similar manner to the above coupling reaction of the compound (35) with $R^{2a}B(OH)_2$ or $R^{2a}BF_3K$.

Alternatively, the compound (22) wherein $R^6$ is optionally substituted cycloalkyl and a precursor compound thereof can be prepared by coupling the corresponding compound (22) wherein $R^6$ is halogen (particularly, bromine or iodine) and a precursor compound thereof, respectively, with $E^4B(OH)_2$ or $E^4BF_3K$ [wherein $E^4$ is the corresponding optionally substituted cycloalkenyl] to obtain a cycloalkenyl compound, followed by hydrogenating the obtained compound.

The coupling reaction of the compound wherein $R^6$ is halogen with $E^4B(OH)_2$ or $E^4BF_3K$ can be carried out in a similar manner to the above coupling reaction of the compound (35) with $R^{2a}B(OH)_2$ or $R^{2a}BF_3K$.

The hydrogenation reaction of the cycloalkenyl compound can be carried out in a similar manner to the hydrogenation reaction to prepare the above compound (22-b).

The compound (22) wherein $R^6$ is optionally substituted dialkylamino or an optionally substituted nitrogen-containing non-aromatic heterocyclic group and a precursor compound thereof can be prepared by reacting the corresponding compound (22) wherein $R^6$ is halogen (particularly, fluorine) and a precursor compound thereof, respectively, with $E^5E^6NH$ [wherein $E^5$ is optionally substituted alkyl, and $E^6$ is optionally substituted alkyl, or $E^5$ and $E^6$ combine with each other at their terminals together with the adjacent nitrogen atom to form an optionally substituted nitrogen-containing non-aromatic heterocyclic group].

The reaction of the compound (22) wherein $R^6$ is halogen or a precursor compound thereof with $E^5E^6NH$ can be carried out in a solvent (for example, an amide such as N,N-dimethylformamide, N,N-dimethylacetamide, 1,3-dimethyl-2-imidazolidinone, or N-methylpyrrolidone). The reaction may be preferably carried out at 20° C. to 180° C.

The compound (22) wherein $R^6$ is optionally substituted alkylamino and a precursor compound thereof can be prepared by reacting the corresponding compound (22) wherein $R^6$ is halogen (particularly, bromine or iodine) and a precursor compound thereof, respectively, with trimethylsilyl azide to obtain an amino compound, followed by reacting the obtained compound with $E^7LG^{10}$ [wherein $E^7$ is optionally substituted alkyl, and $LG^{10}$ is a leaving group such as a halogen, e.g., iodine].

The reaction of the compound wherein $R^6$ is halogen with trimethylsilyl azide can be carried out in a solvent (for example, an amide such as N,N-dimethylformamide, N,N-dimethylacetamide, 1,3-dimethyl-2-imidazolidinone, or N-methylpyrrolidone), and in the presence of copper and a ligand (for example, 2-aminoethanol). The reaction may be preferably carried out at 60° C. to 120° C.

The reaction of the amino compound with $E^7LG^{10}$ can be carried out in a solvent (for example, an amide such as N,N-dimethylformamide, N,N-dimethylacetamide, 1,3-dimethyl-2-imidazolidinone, or N-methylpyrrolidone), and in the presence of a base (for example, an alkali metal hydride such as sodium hydride or potassium hydride). The reaction may be preferably carried out at 0° C. to 60° C.

The other starting compounds are commercially available, or can be easily prepared by a conventional method known to those skilled in the art.

Hereinafter, the present invention is illustrated by EXAMPLES in more detail, but is not limited thereto.

EXAMPLES

In the following Examples, Reference Examples, and Tables, Me is methyl, and Et is ethyl. Also, an optically active substance can be obtained by resolving a racemic mixture using a chiral high performance liquid chromatography (chiral HPLC).

Example 1

Preparation of N-(4-cyclopropylisoquinolin-3-yl)-4-(1H-tetrazol-5-yl)-N-[4-(trifluoromethoxy)benzyl]benzenesulfonamide

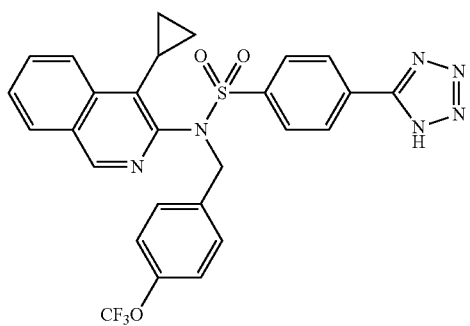

A mixture of 4-cyano-N-(4-cyclopropylisoquinolin-3-yl)-N-[4-(trifluoromethoxy)benzyl]benzenesulfonamide (78.5 mg, 0.150 mmol) obtained in Reference Example 1, sodium azide (12 mg, 0.184 mmol), and ammonium chloride (12 mg, 0.185 mmol) in N,N-dimethylformamide (1.6 mL) was stirred at 100° C. overnight. To the reaction mixture was added ethyl acetate, and the mixture was washed successively with 2 mol/L of hydrochloric acid, water, and saturated saline. The organic layer was dried over sodium sulfate, filtered, and the filtrate was concentrated under reduced pressure. The obtained residue was purified by a silica gel column chromatography (chloroform:methanol=97:3→80:20) to give N-(4-cyclopropylisoquinolin-3-yl)-4-(1H-tetrazol-5-yl)-N-[4-(trifluoromethoxy)benzyl]benzenesulfonamide (58.7 mg, 69%) as a colorless solid.

APCI-MS m/z: 567 [M+H]$^+$.

Example 2

Preparation of N-(4-cyclopropylisoquinolin-3-yl)-6-(1H-tetrazol-5-yl)-N-[4-(trifluoromethoxy)benzyl]pyridine-3-sulfonamide

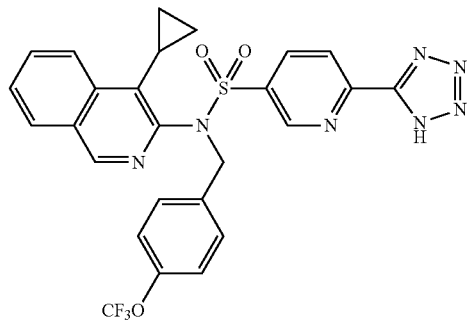

6-Cyano-N-(4-cyclopropylisoquinolin-3-yl)-N-[4-(trifluoromethoxy)benzyl]pyridine-3-sulfonamide (52.5 mg, 0.100 mmol) obtained in Reference Example 6 was treated in a similar manner to Example 1 to give N-(4-cyclopropylisoquinolin-3-yl)-6-(1H-tetrazol-5-yl)-N-[4-(trifluoromethoxy)benzyl]pyridine-3-sulfonamide (37.0 mg, 65%) as a colorless solid.

APCI-MS m/z: 568 [M+H]$^+$.

Example 3

Preparation of N-(4-cyclopropylisoquinolin-3-yl)-5-(1H-tetrazol-5-yl)-N-[4-(trifluoromethoxy)benzyl]pyridine-2-sulfonamide

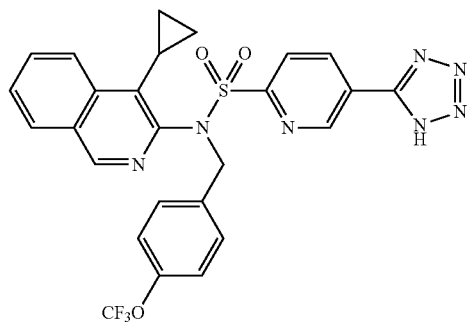

A solution of 5-cyano-N-(4-cyclopropylisoquinolin-3-yl)-N-[4-(trifluoromethoxy)benzyl]pyridine-2-sulfonamide (86.0 mg, 0.164 mmol) obtained in Reference Example 14 and tributyltin azide (109 mg, 0.328 mmol) in toluene (1 mL) was stirred at 110° C. for 19 hours. After cooling, to the reaction mixture were added 1 mol/L of hydrochloric acid and water, and the mixture was extracted with ethyl acetate. The organic layer was washed with water and saturated saline, dried over sodium sulfate, filtered, and the filtrate was concentrated under reduced pressure. The obtained residue was purified by a silica gel column chromatography (chloroform:methanol=100:0→80:20) to give N-(4-cyclopropylisoquinolin-3-yl)-5-(1H-tetrazol-5-yl)-N-[4-(trifluoromethoxy)benzyl]pyridine-2-sulfonamide (26.6 mg, 29%) as a colorless solid.

APCI-MS m/z: 568 [M+H]$^+$.

Example 4

Preparation of N-(4-cyclopropylisoquinolin-3-yl)-4-(5-oxo-4,5-dihydro-1H-tetrazol-1-yl)-N-[4-(trifluoromethoxy)benzyl]benzenesulfonamide

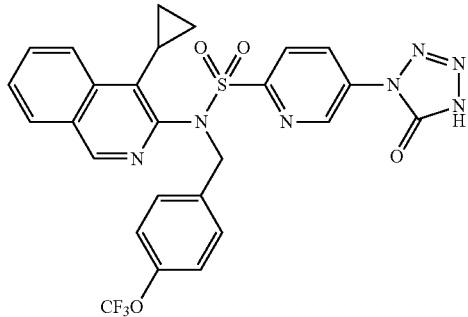

To a solution of 4-({(4-cyclopropylisoquinolin-3-yl)[4-(trifluoromethoxy)benzyl]amino}sulfonyl)benzoic acid (200 mg, 0.369 mmol) obtained in Example 5-(1) in tetrahydrofuran (6.0 mL) were added oxalyl chloride (93.6 mg, 0.737 mmol), and N,N-dimethylformamide (1 drop), and the mixture was stirred at room temperature for 1 hour. The reaction mixture was concentrated under reduced pressure, then to the residue were added hexane and diisopropylether, the obtained solid was collected by filtration, and dried under reduced pressure. To the obtained colorless solid was added trimethylsilyl azide (637 mg, 5.53 mmol), and the mixture was stirred at 95° C. for 16 hours. To the reaction mixture was added ethyl acetate, and the mixture was washed successively with 2 mol/L of hydrochloric acid, water, and saturated saline. The organic layer was dried over sodium sulfate, filtered, and the filtrate was concentrated under reduced pressure. The obtained residue was purified by a silica gel column chromatography (chloroform:methanol=100:0→96:4) to give N-(4-cyclopropylisoquinolin-3-yl)-4-(5-oxo-4,5-dihydro-1H-tetrazol-1-yl)-N-[4-(trifluoromethoxy)benzyl]benzenesulfonamide (98.8 mg, 46%) as a colorless solid.

APCI-MS m/z: 583 [M+H]$^+$.

Example 5

Preparation of N-(4-cyclopropylisoquinolin-3-yl)-4-(2H-1,2,4-triazol-3-yl)-N-[4-(trifluoromethoxy)benzyl]benzenesulfonamide (1) Synthesis of 4-({(4-cyclopropylisoquinolin-3-yl)[4-(trifluoromethoxy)benzyl]amino}sulfonyl)benzoic acid

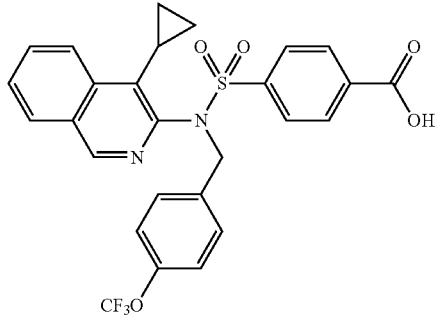

To a solution of ethyl 4-({(4-cyclopropylisoquinolin-3-yl)[4-(trifluoromethoxy)benzyl]amino}sulfonyl)benzoate (30.4 g, 53.3 mmol) obtained in Reference Example 3 in ethanol (200 mL) and tetrahydrofuran (200 mL) was added an aqueous sodium hydroxide solution (2 mol/L, 54 mL, 108 mmol), and the mixture was stirred at room temperature for 1 hour. The reaction mixture was concentrated under reduced pressure until the volume was reduced by about half, acidified by 10% aqueous citric acid solution, and extracted with ethyl acetate. The organic layer was washed with water and saturated saline, dried over sodium sulfate, filtered, and the filtrate was concentrated under reduced pressure. To the residue was added ethanol, the obtained solid was collected by filtration, and dried under reduced pressure to give 4-({(4-cyclopropylisoquinolin-3-yl)[4-(trifluoromethoxy)benzyl]amino}sulfonyl)benzoic acid (25.8 g, 89%) as a white solid. APCI-MS m/z: 543 [M+H]$^+$.

(2) Synthesis of 4-({(4-cyclopropylisoquinolin-3-yl)[4-(trifluoromethoxy)benzyl]amino}sulfonyl)benzamide

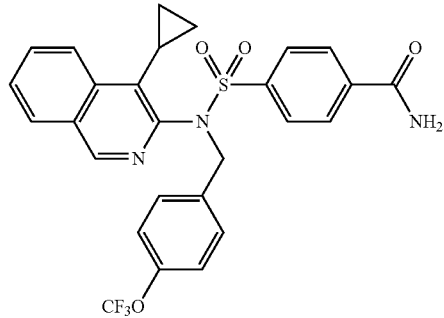

The compound obtained in (1) was treated in a similar manner to Reference Example 4-(3) to give 4-({(4-cyclopropylisoquinolin-3-yl)[4-(trifluoromethoxy)benzyl]amino}sulfonyl)benzamide.

APCI-MS m/z: 542 [M+H]$^+$.

(3) Synthesis of N-(4-cyclopropylisoquinolin-3-yl)-4-(2H-1,2,4-triazol-3-yl)-N-[4-(trifluoromethoxy)benzyl]benzenesulfonamide

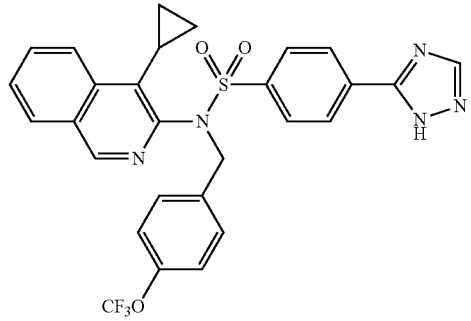

A mixture of the compound obtained in (2) (91.0 mg, 0.168 mmol) and N,N-dimethylformamide dimethylacetal (1.8 mL) was stirred at 120° C. for 2 hours. The reaction mixture was concentrated under reduced pressure, the obtained residue was dissolved in acetic acid (0.9 mL), hydrazine monohydrate (9.0 μl, 0.185 mmol) was added thereto, and the mixture was stirred at 90° C. for 2 hours. The reaction mixture was concentrated under reduced pressure, and the obtained residue was purified by a silica gel column chromatography (hexane:ethyl acetate=100:0→65:35) and an NH silica gel column chromatography (hexane:ethyl acetate=30:70→0:100) to give N-(4-cyclopropylisoquinolin-3-yl)-4-(2H-1,2,4-triazol-3-yl)-N-[4-(trifluoromethoxy)benzyl]benzenesulfonamide (29.0 mg, 31%) as a pale yellow solid.

APCI-MS m/z: 566 [M+H]⁺.

Example 6

Preparation of N-(4-cyclopropylisoquinolin-3-yl)-6-(1H-1,2,4-triazol-5-yl)-N-[4-(trifluoromethoxy)benzyl]pyridine-3-sulfonamide (1) Synthesis of 5-({(4-cyclopropylisoquinolin-3-yl)[4-(trifluoromethoxy)benzyl]amino}sulfonyl)pyridine-2-carboxamide

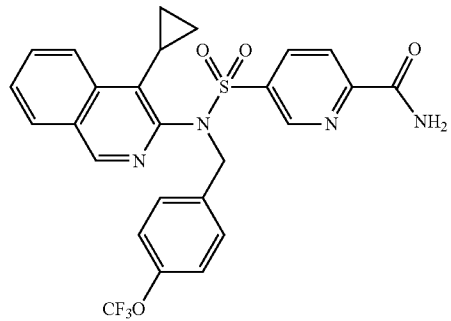

A mixture of 6-cyano-N-(4-cyclopropylisoquinolin-3-yl)-N-[4-(trifluoromethoxy)benzyl]pyridine-3-sulfonamide obtained in Reference Example 6 (80.0 mg, 0.153 mmol) and potassium hydroxide (34.2 mg, 0.610 mmol) in t-butanol (3 mL) was stirred at 80° C. for 10 minutes. 1,4-Dioxane (0.5 mL) was added thereto, and the reaction mixture was stirred at 80° C. for 20 minutes. After cooling, to the reaction mixture were added 1 mol/L of hydrochloric acid and water, and the mixture was extracted with ethyl acetate. The organic layer was separated, washed with water and saturated saline, dried over sodium sulfate, filtered, and the filtrate was concentrated under reduced pressure. The obtained residue was purified by a silica gel column chromatography (hexane:ethyl acetate=80:20→50:50) to give 5-({(4-cyclopropylisoquinolin-3-yl)[4-(trifluoromethoxy)benzyl]amino}sulfonyl)pyridine-2-carboxamide (68.0 mg, 82%) as a colorless solid.

APCI-MS m/z: 543 [M+H]⁺.

(2) Synthesis of N-(4-cyclopropylisoquinolin-3-yl)-6-(1H-1,2,4-triazol-5-yl)-N-[4-(trifluoromethoxy)benzyl]pyridine-3-sulfonamide

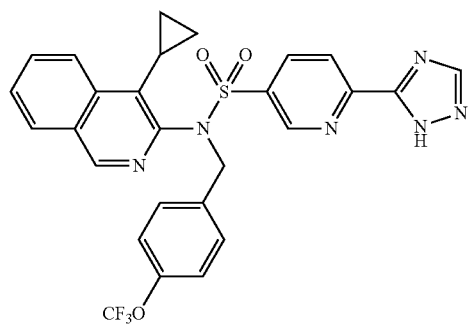

The compound obtained in (1) was treated in a similar manner to Example 5-(3) to give N-(4-cyclopropylisoquinolin-3-yl)-6-(1H-1,2,4-triazol-5-yl)-N-[4-(trifluoromethoxy)benzyl]pyridine-3-sulfonamide.

APCI-MS m/z: 567 [M+H]⁺.

Example 7

Preparation of N-(4-cyclopropylisoquinolin-3-yl)-4-(5-oxo-4,5-dihydro-1,2,4-oxadiazol-3-yl)-N-[4-(trifluoromethoxy)benzyl]benzenesulfonamide (1) Synthesis of 4-({(4-cyclopropylisoquinolin-3-yl)[4-(trifluoromethoxy)benzyl]amino}sulfonyl)-N'-hydroxybenzenecarboximidamide

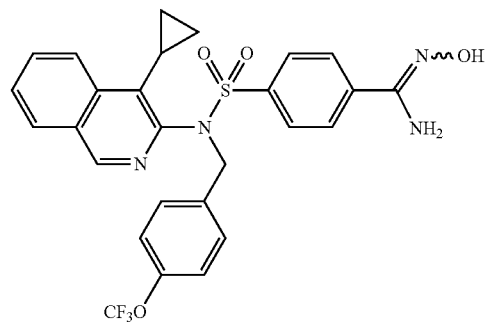

A mixture of 4-cyano-N-(4-cyclopropylisoquinolin-3-yl)-N-[4-(trifluoromethoxy)benzyl]benzenesulfonamide obtained in Reference Example 1 (78.5 mg, 0.15 mmol), hydroxyamine hydrochloride (12.5 mg, 0.18 mmol), and triethylamine (18.2 mg, 0.18 mmol) in ethanol (1.6 mL) was stirred at 50° C. for 5 hours. The reaction mixture was concentrated under reduced pressure, and to the residue were added ethyl acetate and water. The organic layer was separated, washed with saturated saline, dried over sodium sulfate, and filtered. The obtained filtrate was concentrated under reduced pressure to give a crude product of 4-({(4-cyclopropylisoquinolin-3-yl)[4-(trifluoromethoxy)benzyl]amino}sulfonyl)-N-hydroxybenzenecarboximidamide (88 mg). The resultant was used in the next step without further purification.

APCI-MS m/z: 557 [M+H]⁺.

(2) Synthesis of 4-({(4-cyclopropylisoquinolin-3-yl)[4-(trifluoromethoxy)benzyl]amino}sulfonyl)-N'-({[(2-ethylhexyl)oxy]carbonyl}oxy)benzenecarboximidamide

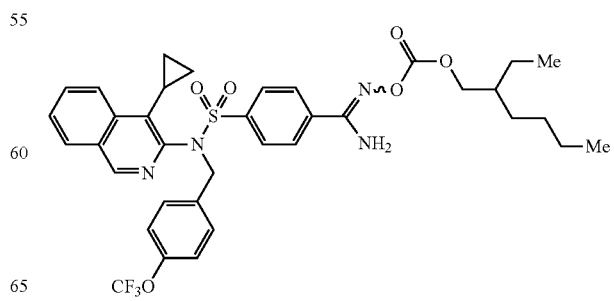

The crude product obtained in (1) was dissolved in N,N-dimethylformamide (1 mL), and to the solution was added pyridine (12 μL, 0.15 mmol) at room temperature. The reaction solution was cooled to 0° C., 2-ethylhexyl chloroformate (29 μL, 0.15 mmol) was added thereto, the mixture was stirred at the same temperature for 1 hour, and then stirred at 120° C. for 4 hours. After cooled to room temperature, to the reaction mixture was added water, and the mixture was extracted with ethyl acetate. The organic layer was washed with saturated saline, dried over sodium sulfate, filtered, and the filtrate was concentrated under reduced pressure. The obtained residue was purified by a silica gel column chromatography (hexane:ethyl acetate 85:15→65:35) to give 4-({(4-cyclopropylisoquinolin-3-yl)[4-(trifluoromethoxy)benzyl]amino}sulfonyl)-N'-({[(2-ethylhexyl)oxy]carbonyl}oxy)benzenecarboximidamide (55 mg, 51%) as a viscous material.

APCI-MS m/z: 714 [M+H]⁺.

(3) Synthesis of N-(4-cyclopropylisoquinolin-3-yl)-4-(5-oxo-4,5-dihydro-1,2,4-oxadiazol-3-yl)-N-[4-(trifluoromethoxy)benzyl]benzenesulfonamide

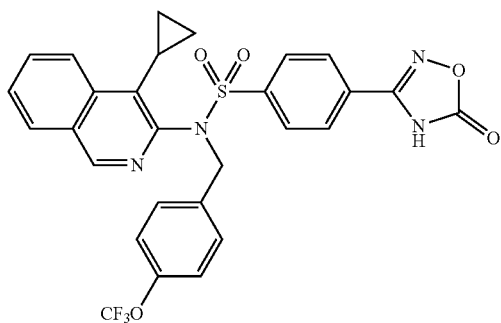

A solution of the compound obtained in (2) (50 mg, 0.070 mmol) in 1-methyl-2-pyrrolidone (1.5 mL) was stirred at 140° C. for 5 hours. After cooled to room temperature, to the reaction mixture was added water, and the mixture was extracted with ethyl acetate. The organic layer was washed with saturated saline, dried over sodium sulfate, filtered, and the filtrate was concentrated under reduced pressure. The obtained residue was purified by a silica gel column chromatography (chloroform:methanol=100:0→90:10). To the residue were added diisopropylether and hexane, the obtained solid was collected by filtration, and dried under reduced pressure to give N-(4-cyclopropylisoquinolin-3-yl)-4-(5-oxo-4,5-dihydro-1,2,4-oxadiazol-3-yl)-N-[4-(trifluoromethoxy)benzyl]benzenesulfonamide (22 mg, 53%) as a white solid.

ESI-MS m/z: 581 [M−H]⁻.

Example 8

Preparation of 4-(5-oxo-4,5-dihydro-1,2,4-oxadiazol-3-yl)-N-[4-(trifluoromethoxy)benzyl]-N-[4-(trifluoromethyl)isoquinolin-3-yl]benzenesulfonamide (1) Synthesis of N'-hydroxy-4-({[4-(trifluoromethoxy)benzyl][4-(trifluoromethyl)isoquinolin-3-yl]amino}sulfonyl)benzenecarboximidamide

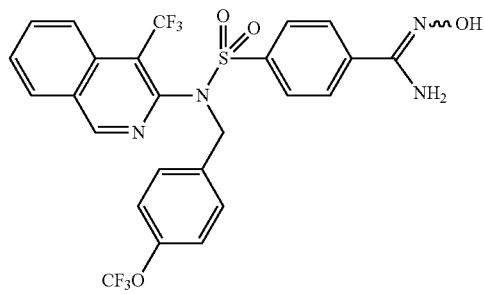

A mixture of 4-cyano-N-[4-(trifluoromethoxy)benzyl]-N-[4-(trifluoromethyl)isoquinolin-3-yl]benzenesulfonamide obtained in Reference Example 4 (120.0 mg, 0.218 mmol), triethylamine (36.4 μL, 0.261 mmol), and hydroxyamine hydrochloride (18.1 mg, 0.261 mmol) in ethanol (2.2 mL) was stirred at 50° C. overnight. The reaction mixture was cooled to room temperature, and concentrated under reduced pressure. To the residue was added water, and the mixture was extracted three times with ethyl acetate. The organic layer was combined and dried, and concentrated under reduced pressure to give a crude product of N'-hydroxy-4-({[4-(trifluoromethoxy)benzyl][4-(trifluoromethyl)isoquinolin-3-yl]amino}sulfonyl)benzenecarboximidamide (143.0 mg) as a pale yellow solid. The resultant was used in the next step without further purification.

APCI-MS m/z: 585 [M+H]⁺.

(2) Synthesis of 4-(5-oxo-4,5-dihydro-1,2,4-oxadiazol-3-yl)-N-[4-(trifluoromethoxy)benzyl]-N-[4-(trifluoromethyl)isoquinolin-3-yl]benzenesulfonamide

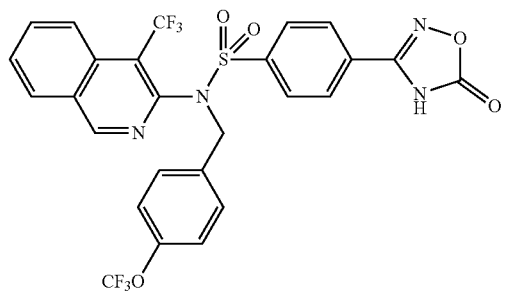

To a solution of the crude product obtained in (1) (127.0 mg) in tetrahydrofuran (1.1 mL) were added 1,8-diazabicyclo[5.4.0]undec-7-ene (65.0 μL, 0.435 mmol) and carbonyldiimidazole (70.5 mg, 0.435 mmol), and the mixture was stirred at room temperature overnight. To the reaction mixture was added water, and the mixture was extracted three times with ethyl acetate. The organic layer was combined and washed twice with water, dried, and concentrated under reduced pressure. The obtained residue was purified by a silica gel column chromatography (chloroform:methanol=100:0→93:7) to give 4-(5-oxo-4,5-dihydro-1,2,4-oxadiazol-3-yl)-N-[4-(trifluoromethoxy)benzyl]-N-[4-(trifluoromethyl)isoquinolin-3-yl]benzenesulfonamide (83.0 mg, yield for two steps: 63%) as a white solid.

APCI-MS m/z: 611 [M+H]+.

Example 9

Preparation of N-(4-cyclopropylisoquinolin-3-yl)-6-(5-oxo-4,5-dihydro-1,2,4-oxadiazol-3-yl)-N-[4-(trifluoromethoxy)benzyl]pyridine-3-sulfonamide (1) Synthesis of 5-({(4-cyclopropylisoquinolin-3-yl)[4-(trifluoromethoxy)benzyl]amino}sulfonyl)-N'-hydroxypyridine-2-carboximidamide

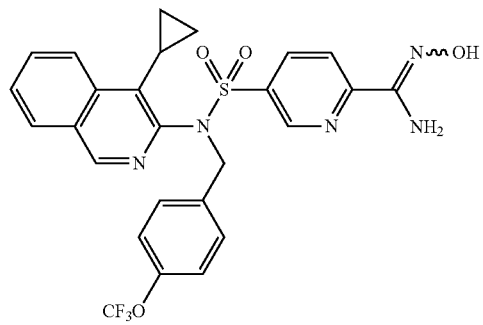

6-Cyano-N-(4-cyclopropylisoquinolin-3-yl)-N-[4-(trifluoromethoxy)benzyl]pyridine-3-sulfonamide obtained in Reference Example 6 (52.5 mg, 0.100 mmol) was treated in a similar manner to Example 8-(1) to give a crude product of 5-({(4-cyclopropylisoquinolin-3-yl)[4-(trifluoromethoxy)benzyl]amino}sulfonyl)-N'-hydroxypyridine-2-carboximidamide (61.8 mg) as a pale yellow solid. The resultant was used in the next step without further purification.

APCI-MS m/z: 558 [M+H]+.

(2) Synthesis of N-(4-cyclopropylisoquinolin-3-yl)-6-(5-oxo-4,5-dihydro-1,2,4-oxadiazol-3-yl)-N-[4-(trifluoromethoxy)benzyl]pyridine-3-sulfonamide

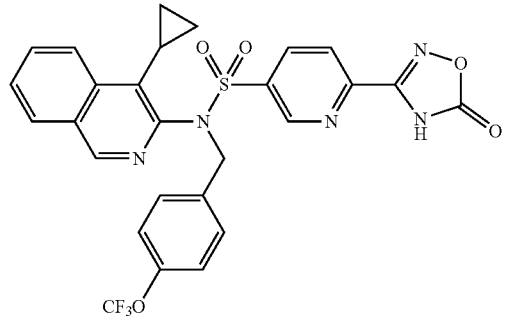

The crude product obtained in (1) (55.4 mg) was treated in a similar manner to Example 8-(2) to give N-(4-cyclopropylisoquinolin-3-yl)-6-(5-oxo-4,5-dihydro-1,2,4-oxadiazol-3-yl)-N-[4-(trifluoromethoxy)benzyl]pyridine-3-sulfonamide (36.8 mg, yield for two steps: 64%) as a colorless solid.

APCI-MS m/z: 584 [M+H]+.

Example 10

Preparation of N-[4-({(4-cyclopropylisoquinolin-3-yl)[4-(trifluoromethoxy)benzyl]amino}sulfonyl)benzyl]acetamide (1) Synthesis of N-(4-cyclopropylisoquinolin-3-yl)-4-(hydroxymethyl)-N-[4-(trifluoromethoxy)benzyl]benzenesulfonamide

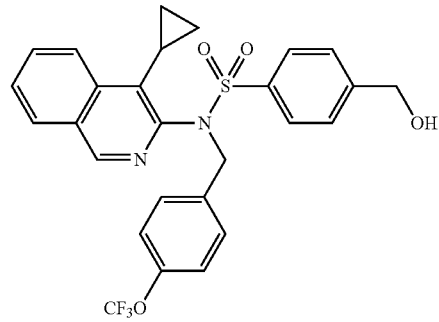

Under argon atmosphere, to a solution of ethyl 4-({4-cyclopropylisoquinolin-3-yl)[4-(trifluoromethoxy)benzyl]amino}sulfonyl)benzoate obtained in Reference Example 3 (1 g, 1.75) in tetrahydrofuran (18 mL) was added dropwise diisobutylaluminum hydride (1 mol/L solution in dichloromethane, 2.46 mL, 2.46 mmol) at −78° C., and the mixture was stirred at the same temperature for 2 hours. To the reaction mixture was added additional diisobutylaluminum hydride (1 mol/L solution in dichloromethane, 4.56 mL, 4.56 mmol), and the mixture was stirred at the same temperature for 2 hours. To the reaction mixture was added methanol, the mixture was gradually warmed to room temperature, then to the reaction mixture were added ethyl acetate and an aqueous saturated potassium sodium tartrate solution, and the reaction mixture was stirred vigorously at room temperature for 2 hours. The organic layer was separated, washed with saturated saline, dried over sodium sulfate, then filtered, and the filtrate was concentrated under reduced pressure. The obtained residue was purified by a silica gel column chromatography (hexane:ethyl acetate=65:35→35:65) to give N-(4-cyclopropylisoquinolin-3-yl)-4-(hydroxymethyl)-N-[4-(trifluoromethoxy)benzyl]benzenesulfonamide (853 mg, 92%) as a colorless viscous material.

APCI-MS m/z: 529 [M+H]+.

(2) Synthesis of 4-(aminomethyl)-N-(4-cyclopropylisoquinolin-3-yl)-N-[4-(trifluoromethoxy)benzyl]benzenesulfonamide

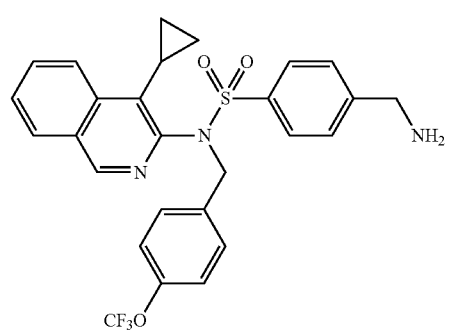

A mixture of the compound obtained in (1) (748 mg, 1.41 mmol), diphenylphosphoryl azide (366 μL, 1.70 mmol), and 1,8-diazabicyclo[5.4.0]-7-undecene (254 μL, 1.70 mmol) in tetrahydrofuran (7.5 mL) was stirred at room temperature overnight. To the reaction mixture were added triphenylphosphine (481 mg, 1.83 mmol) and water (900 μL), and the reaction mixture was stirred at 60° C. for 2.5 hours. After cooled to room temperature, to the reaction mixture were added ethyl acetate and water. The organic layer was separated, washed with saturated saline, dried over sodium sulfate, then filtered, and the filtrate was concentrated under reduced pressure. The obtained residue was purified by a silica gel column chromatography (chloroform:methanol=100:0→85:15) to give 4-(aminomethyl)-N-(4-cyclopropylisoquinolin-3-yl)-N-[4-(trifluoromethoxy)benzyl]benzenesulfonamide (708 mg, 95%) as a colorless viscous material.

APCI-MS m/z: 528 [M+H]$^+$.

(3) Synthesis of N-[4-({(4-cyclopropylisoquinolin-3-yl)[4-(trifluoromethoxy)benzyl]amino}sulfonyl)benzyl]acetamide

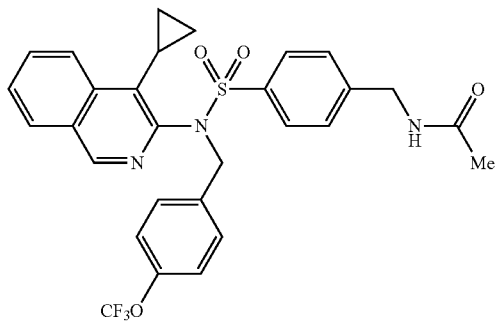

To a solution of the compound obtained in (2) (84 mg, 0.159 mmol) and triethylamine (66 μL, 0.477 mmol) in dichloromethane (2 mL) was added acetic anhydride (15 μL, 0.207 mmol) at 0° C., and the mixture was stirred at the same temperature for 1 hour. To the reaction mixture were added ethyl acetate and water, the organic layer was separated, washed with saturated saline, dried over sodium sulfate, filtered, and the filtrate was concentrated under reduced pressure. The obtained residue was purified by a silica gel column chromatography (chloroform:methanol=100:0→93:7) to give N-[4-({(4-cyclopropylisoquinolin-3-yl)[4-(trifluoromethoxy)benzyl]amino}sulfonyl)benzyl]acetamide (72 mg, 80%) as a colorless solid.

APCI-MS m/z: 570 [M+H]$^+$.

Example 11

Preparation of N-(4-cyclopropylisoquinolin-3-yl)-4-{[(methylsulfonyl)amino]methyl}-N-[4-(trifluoromethoxy)benzyl]benzenesulfonamide

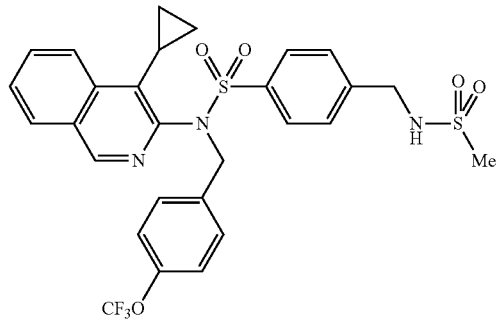

To a solution of 4-(aminomethyl)-N-(4-cyclopropylisoquinolin-3-yl)-N-[4-(trifluoromethoxy)benzyl]benzenesulfonamide obtained in Example 10-(2) (80 mg, 0.152 mmol) and triethylamine (64 μL, 0.456 mmol) in dichloromethane (2 mL) was added methanesulfonyl chloride (15 μL, 0.197 mmol) at 0° C., and the mixture was stirred at the same temperature for 20 minutes. To the reaction mixture were added ethyl acetate and water, the organic layer was separated, washed with saturated saline, dried over sodium sulfate, filtered, and the filtrate was concentrated under reduced pressure. The obtained residue was purified by a silica gel column chromatography (chloroform:methanol=100:0→93:7) to give N-(4-cyclopropylisoquinolin-3-yl)-4-{[(methylsulfonyl)amino]methyl}-N-[4-(trifluoromethoxy)benzyl]benzenesulfonamide (70 mg, 76%) as a colorless solid.

APCI-MS m/z: 606 [M+H]$^+$.

Example 12

Preparation of N-(4-cyclopropylisoquinolin-3-yl)-N-[4-(trifluoromethoxy)benzyl]-4-({[(trifluoromethyl)sulfonyl]amino}methyl)benzenesulfonamide

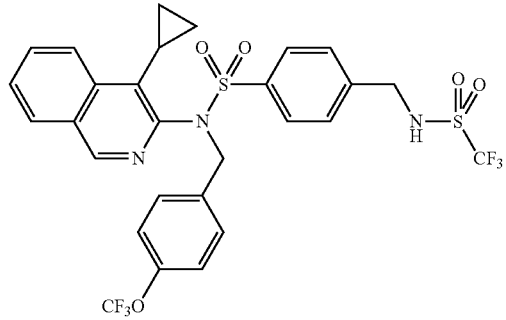

To a solution of 4-(aminomethyl)-N-(4-cyclopropylisoquinolin-3-yl)-N-[4-(trifluoromethoxy)benzyl]benzenesulfonamide obtained in Example 10-(2) (80 mg, 0.152 mmol) and triethylamine (64 μL, 0.456 mmol)) in dichloromethane (2 mL) was added trifluoromethanesulfonic acid anhydride (33 μL, 0.197 mmol) at −78° C., and the mixture was stirred at the same temperature for 20 minutes. To the mixture were added ethyl acetate and water, and the reaction mixture was warmed to room temperature. The organic layer was separated, washed with saturated saline, dried over sodium sulfate, filtered, and the filtrate was concentrated under reduced pressure. The obtained residue was purified by a silica gel column chromatography (chloroform:methanol=100:0→95:5) to give N-(4-cyclopropylisoquinolin-3-yl)-N-[4-(trifluoromethoxy)benzyl]-4-({[trifluoromethyl)sulfonyl]amino}methyl)benzenesulfonamide (79 mg, 79%) as a colorless solid.

APCI-MS m/z: 660 [M+H]+.

Example 13

Preparation of N-(4-cyclopropylisoquinolin-3-yl)-3-oxo-N-[4-(trifluoromethoxy)benzyl]-2,3-dihydro-1H-indazole-6-sulfonamide

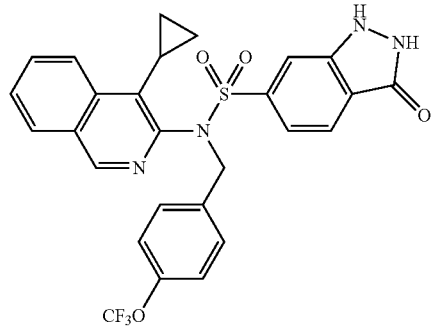

A mixture of methyl 4-({(4-cyclopropylisoquinolin-3-yl)[4-(trifluoromethoxy)benzyl]amino}sulfonyl)-2-fluorobenzoate obtained in Reference Example 7 (32.0 mg, 0.0557 mmol) and hydrazine monohydrate (55.8 mg, 1.11 mmol) in ethanol (0.558 mL) was stirred at 100° C. for 1 hour under microwave irradiation. To the reaction mixture was added ethyl acetate, the mixture was washed with water, the organic layer was dried over sodium sulfate, filtered, and the filtrate was concentrated under reduced pressure. The obtained residue was purified by a silica gel column chromatography (chloroform:methanol=100:0→93:7) to give N-(4-cyclopropylisoquinolin-3-yl)-3-oxo-N-[4-(trifluoromethoxy)benzyl]-2,3-dihydro-1H-indazole-6-sulfonamide (22.3 mg, 72%) as a colorless solid.

APCI-MS m/z: 555 [M+H]+.

Examples 14 to 17

The corresponding starting compounds were treated in a similar manner to Example 1 to give the following compounds of Table 1.

TABLE 1

| Example | Structure | Physical data |
|---------|-----------|---------------|
| 14 | 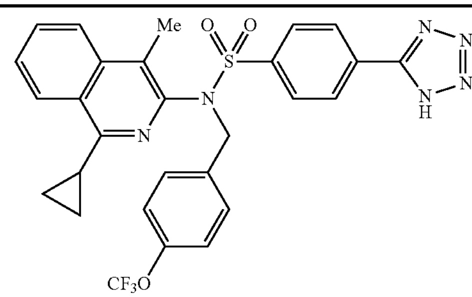 | APCI-MS m/z: 581 [M + H]+ |
| 15 | 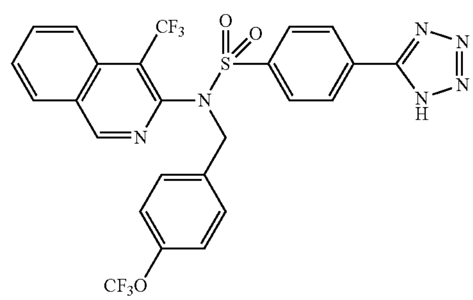 | APCI-MS m/z: 595 [M + H]+ |
| 16 | 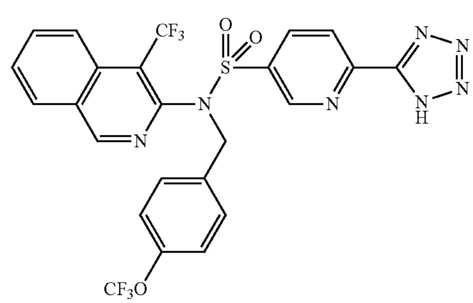 | APCI-MS m/z: 596 [M + H]+ |

TABLE 1-continued

| Example | Structure | Physical data |
|---------|-----------|---------------|
| 17 | 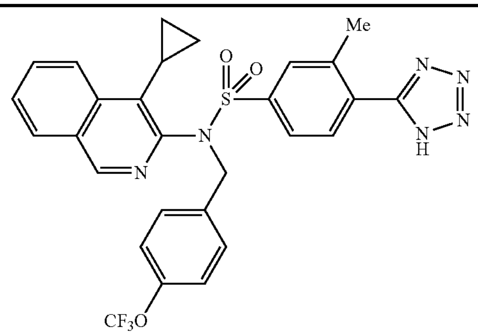 | APCI-MS m/z: 581 [M + H]+ |

Example 18

The corresponding starting compound was treated in a similar manner to Example 3 to give the following compound of Table 2.

TABLE 2

| Example | Structure | Physical data |
|---------|-----------|---------------|
| 18 | 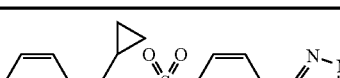 | APCI-MS m/z: 552 [M + H]+ |

Examples 19 to 27

The corresponding starting compounds were treated in a similar manner to Example 5 to give the following compounds of Table 3.

TABLE 3

| Example | Structure | Physical data |
|---------|-----------|---------------|
| 19 | 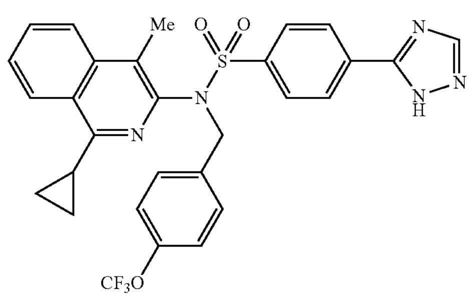 | APCI-MS m/z: 580 [M + H]+ |

TABLE 3-continued

| Example | Structure | Physical data |
|---|---|---|
| 20 | 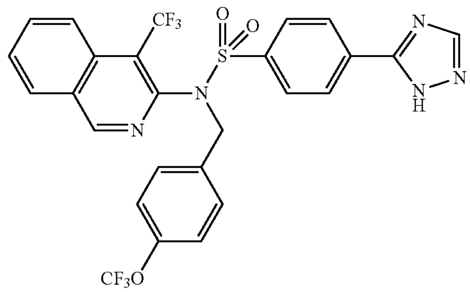 | APCI-MS m/z: 594 [M + H]+ |
| 21 | 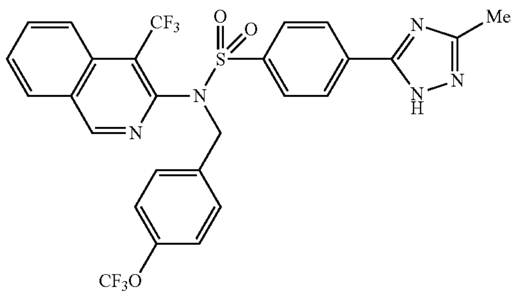 | APCI-MS m/z: 608 [M + H]+ |
| 22 | 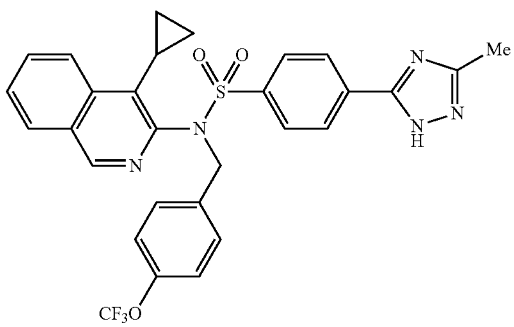 | APCI-MS m/z: 580 [M + H]+ |
| 23 | 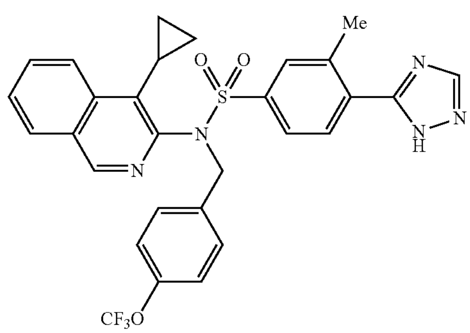 | APCI-MS m/z: 580 [M + H]+ |
| 24 | 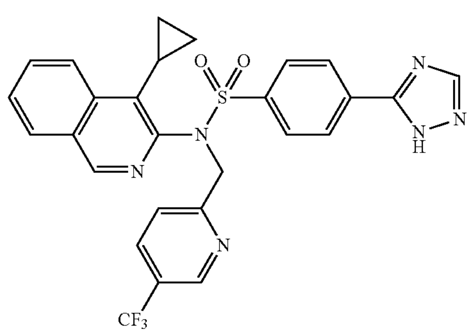 [SMILES: O=S(=O)(c1ccc(-c2ncn[nH]2)cc1)N(Cc1ccc(C(F)(F)F)cn1)c1ncc2ccccc2c1C1CC1] | APCI-MS m/z: 551 [M + H]+ |

TABLE 3-continued
| Example | Structure | Physical data |
|---|---|---|
| 25 | 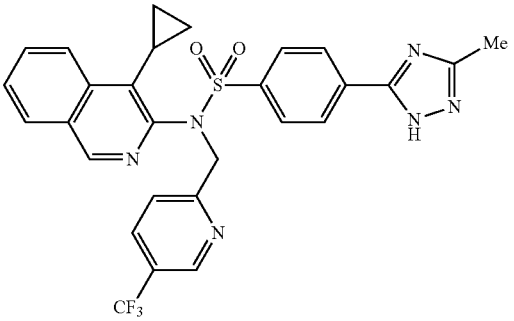 [SMILES: Cc1n[nH]c(-c2ccc(S(=O)(=O)N(Cc3ccc(C(F)(F)F)cn3)c3ncc4ccccc4c3C3CC3)cc2)n1] | APCI-MS m/z: 565 [M + H]+ |
| 26 | 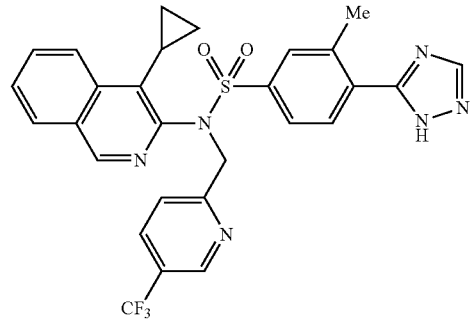 [SMILES: Cc1cc(S(=O)(=O)N(Cc2ccc(C(F)(F)F)cn2)c2ncc3ccccc3c2C2CC2)ccc1-c1ncn[nH]1] | APCI-MS m/z: 565 [M + H]+ |
| 27 | 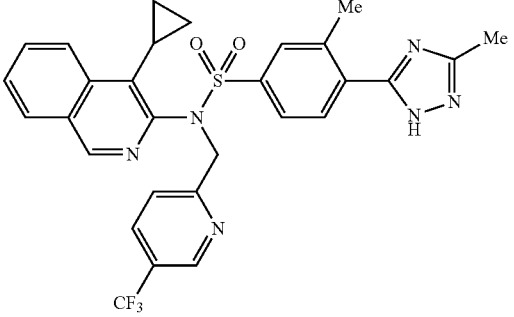 [SMILES: Cc1n[nH]c(-c2ccc(S(=O)(=O)N(Cc3ccc(C(F)(F)F)cn3)c3ncc4ccccc4c3C3CC3)cc2C)n1] | APCI-MS m/z: 579 [M + H]+ |
Examples 28 to 30
The corresponding starting compounds were treated in a similar manner to Example 6 to give the following compounds of Table 4.
TABLE 4
| Example | Structure | Physical data |
|---|---|---|
| 28 | 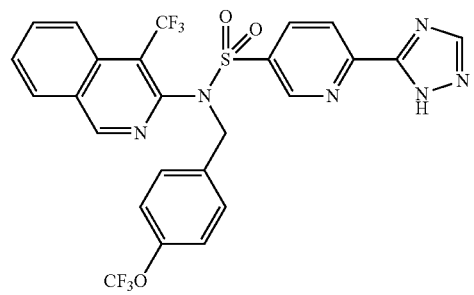 | APCI-MS m/z: 595 [M + H]+ |

TABLE 4-continued

| Example | Structure | Physical data |
|---|---|---|
| 29 | 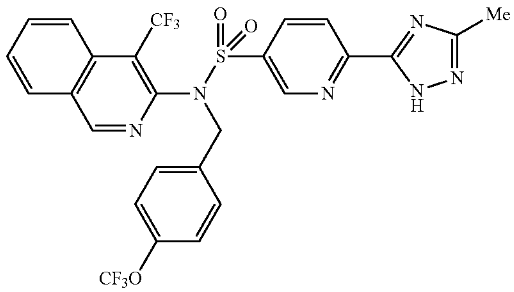 | APCI-MS m/z: 609 [M + H]+ |
| 30 | 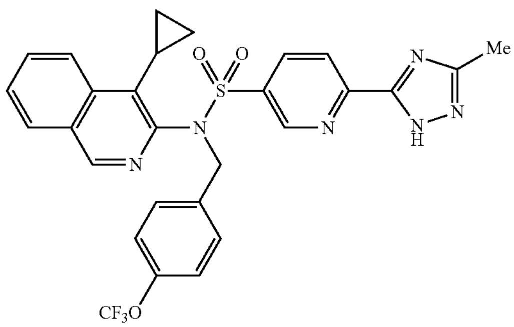 | APCI-MS m/z: 581 [M + H]+ |

Example 31

The corresponding starting compound was treated in a similar manner to Example 7 to give the following compound of Table 5.

TABLE 5

| Example | Structure | Physical data |
|---|---|---|
| 31 | 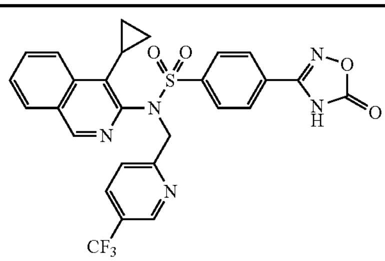 | APCI-MS m/z: 568 [M + H]+ |

Examples 32 to 35

The corresponding starting compounds were treated in a similar manner to Examples 8 and/or 9 to give the following compounds of Table 6.

TABLE 6

| Example | Structure | Physical data |
|---|---|---|
| 32 | 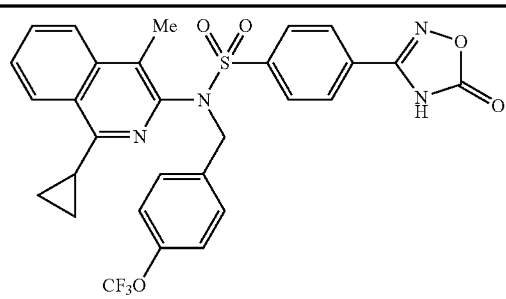 | APCI-MS m/z: 597 [M + H]+ |

TABLE 6-continued

| Example | Structure | Physical data |
|---|---|---|
| 33 | 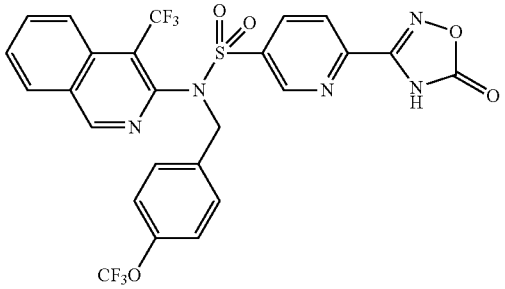 | APCI-MS m/z: 612 [M + H]+ |
| 34 | 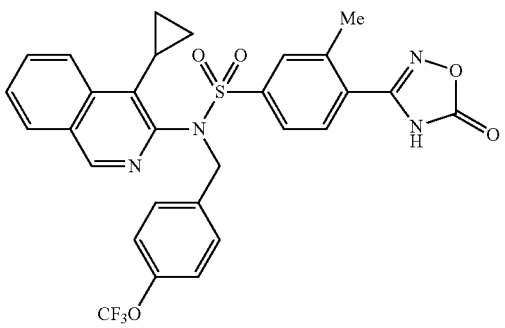 | ESI-MS m/z: 595 [M − H]− |
| 35 | 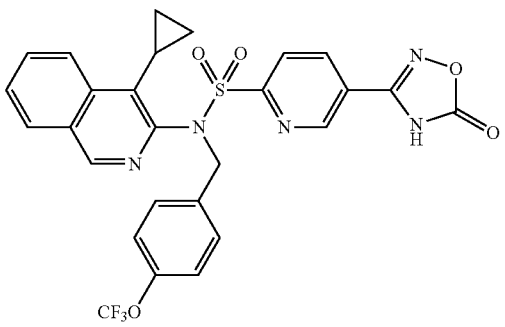 | APCI-MS m/z: 584 [M + H]+ |

Example 36

Preparation of 4-({(4-cyclopropylisoquinolin-3-yl)[4-(trifluoromethoxy)benzyl]amino}sulfonyl)-2-methylbenzoic acid

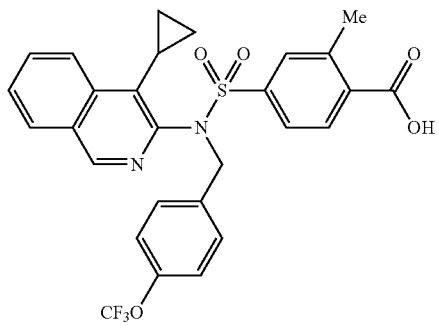

To a mixture of methyl 4-({(4-cyclopropylisoquinolin-3-yl)[4-(trifluoromethoxy)benzyl]amino}sulfonyl)-2-methylbenzoate obtained in Reference Example 15 (404.9 mg, 0.709 mmol) in ethanol (4 mL) was added an aqueous sodium hydroxide solution (2 mol/L, 0.71 mL, 1.42 mmol) at 5° C. The reaction temperature was gradually elevated, and the reaction mixture was stirred at room temperature for 3 days. The reaction mixture was concentrated under reduced pressure, water was added thereto, and the mixture was cooled to 5° C. To this solution was added dropwise concentrated hydrochloric acid to adjust the mixture to pH 1 to 2. The mixture was stirred at 5° C. for 20 minutes, the precipitated solid was collected by filtration, and washed with water to give 4-({(4-cyclopropylisoquinolin-3-yl)[4-(trifluoromethoxy)benzyl]amino}sulfonyl)-2-methylbenzoic acid (385 mg, 98%) as a white solid.

APCI-MS m/z: 557 [M+H]+.

Example 37

Preparation of 4-[((4-cyclopropylisoquinolin-3-yl){[5-(trifluoromethyl)pyridin-2-yl]methyl}amino)sulfonyl]-2-methylbenzoic acid

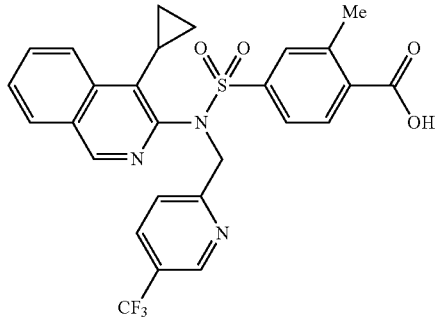 [SMILES: Cc1cc(S(=O)(=O)N(Cc2ccc(C(F)(F)F)cn2)c2ncc3ccccc3c2C2CC2)ccc1C(=O)O]

To a mixture of methyl 4-[((4-cyclopropylisoquinolin-3-yl){[5-(trifluoromethyl)pyridin-2-yl]methyl}amino)sulfonyl]-2-methylbenzoate obtained in Reference Example 16 (101.5 mg, 0.183 mmol) in ethanol (2 mL) was added an aqueous sodium hydroxide solution (2 mol/L, 0.137 mL, 0.274 mmol) at 5° C. The reaction temperature was gradually elevated, and the reaction mixture was stirred at room temperature for 7 hours, then tetrahydrofuran (0.4 mL) was added thereto, and the mixture was stirred overnight. The reaction mixture was poured into saturated saline, and concentrated hydrochloric acid was added thereto to adjust the mixture to pH 1 to 2. The mixture was extracted with chloroform, the organic layer was washed with saturated saline, dried over magnesium sulfate, filtered, and the filtrate was concentrated under reduced pressure. The obtained pale green oil was purified by a silica gel column chromatography (chloroform:methanol=100:0→95:5) to give 4-[((4-cyclopropylisoquinolin-3-yl){[5-(trifluoromethyl)pyridin-2-yl]methyl}amino)sulfonyl]-2-methylbenzoic acid (24.4 mg, 25%) as a pale yellow solid.

APCI-MS m/z: 542 [M+H]+,

1H-NMR (DMSO-d6) δ 0.58 (2H, br), 1.11 (2H, br), 2.09-2.13 (1H, m), 2.51 (3H, s), 5.11 (2H, s), 7.50 (1H, d, J=8.2 Hz), 7.58 (1H, dd, J=1.8 Hz, 8.5 Hz), 7.62 (1H, s), 7.71-7.75 (1H, m), 7.85-7.89 (2H, m), 8.03 (1H, dd, J=2.4, 8.5 Hz), 8.15 (1H, d, J=7.9 Hz), 8.48 (1H, d, J=8.5 Hz), 8.75 (1H, m), 9.07 (1H, s).

Example 38

Preparation of 4-({(4-cyclopropylisoquinolin-3-yl)[4-(trifluoromethoxy)benzyl]amino}sulfonyl)-3-methylbenzoic acid

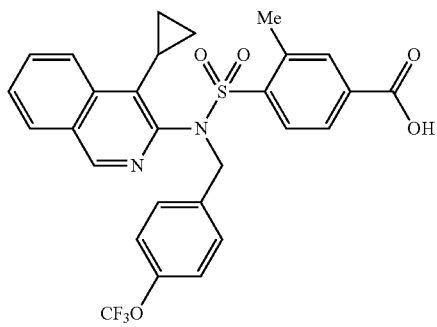

To a mixture of methyl 4-({(4-cyclopropylisoquinolin-3-yl)[4-(trifluoromethoxy)benzyl]amino}sulfonyl)-3-methylbenzoate obtained in Reference Example 17 (60 mg, 0.105 mmol) in ethanol (2 mL) was added an aqueous sodium hydroxide solution (1 mol/L, 210 μL, 0.210 mmol) at 5° C. The reaction temperature was gradually elevated, and the reaction mixture was stirred at room temperature overnight. The reaction mixture was concentrated, and then water and hydrochloric acid (6 mol/L) were successively added thereto to adjust the mixture to pH 1 to 2. The precipitated solid was collected by filtration, and washed with water and hexane to give 4-({(4-cyclopropylisoquinolin-3-yl)[4-(trifluoromethoxy)benzyl]amino}sulfonyl)-3-methylbenzoic acid (54.7 mg, 94%) as a white solid.

APCI-MS m/z: 557 [M+H]+,

1H-NMR (DMSO-d6) δ 0.15 (2H, br), 1.01 (2H, br), 2.11 (1H, m), 2.02 (3H, s), 4.89 (2H, s), 7.19 (2H, d, J=7.9 Hz), 7.27 (1H, d, J=8.8 Hz), 7.72-7.76 (1H, m), 7.85-7.92 (3H, m), 8.12 (1H, d, J=8.5 Hz), 8.17 (1H, d, J=7.9 Hz), 8.46 (1H, d, J=8.5 Hz), 9.14 (1H, s), 13.4 (1H, br).

Example 39

Preparation of 4-({(4-cyclopropylisoquinolin-3-yl)[4-(trifluoromethoxy)benzyl]amino}sulfonyl)-2-(methoxymethyl)benzoic acid

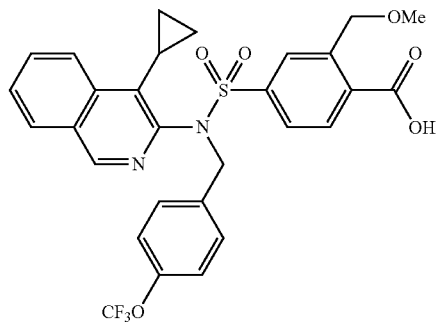

To a mixture of methyl 4-({(4-cyclopropylisoquinolin-3-yl)[4-(trifluoromethoxy)benzyl]amino}sulfonyl)-2-(methoxymethyl)benzoate obtained in Reference Example 19 (44 mg, 0.073 mmol) in ethanol (2 mL) was added an aqueous sodium hydroxide solution (2 mol/L, 0.73.3 μL, 0.147 mmol) at 5° C., then the reaction temperature was gradually elevated, and the mixture was stirred at room temperature overnight. To the reaction mixture was added water, then hydrochloric acid (2 mol/L) was added thereto to adjust the mixture to pH 1 to 2. The precipitated solid was collected by filtration, and washed with water to give 4-({(4-cyclopropylisoquinolin-3-yl)[4-(trifluoromethoxy)benzyl]amino}sulfonyl)-2-(methoxymethyl)benzoic acid (38.8 mg, 90%) as a white solid.

APCI-MS m/z: 587 [M+H]+.

Example 40

Preparation of 4-({(1-cyclopropyl-4-methylisoquinolin-3-yl)[4-(trifluoromethoxy)benzyl]amino}sulfonyl)-2-methylbenzoic acid

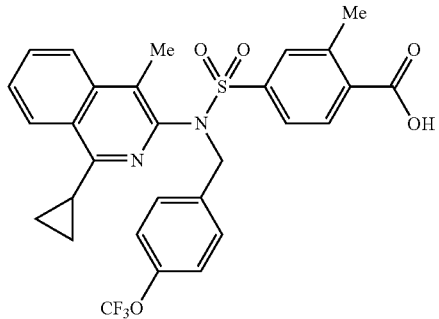

Methyl 4-({(1-cyclopropyl-4-methylisoquinolin-3-yl)[4-(trifluoromethoxy)benzyl]amino}sulfonyl)-2-methylbenzoate obtained in Reference Example 22 (520 mg, 0.889 mmol) was treated in a similar manner to Example 36 to give 4-({(1-cyclopropyl-4-methylisoquinolin-3-yl)[4-(trifluoromethoxy)benzyl]amino}sulfonyl)-2-methylbenzoic acid (445 mg, 88%) as a pale yellow solid.

APCI-MS m/z: 571 [M+H]$^+$.

Example 41

Preparation of 4-({(4-cyclopropylisoquinolin-3-yl)[4-(trifluoromethoxy)benzyl]amino}sulfonyl)-2-(methylamino)benzoic acid

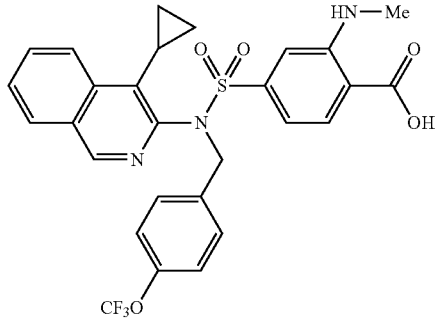

To a solution of methyl 2-amino-4-({(4-cyclopropylisoquinolin-3-yl)[4-(trifluoromethoxy)benzyl]amino}sulfonyl)benzoate obtained in Reference Example 24 (22.0 mg, 0.038 mmol) in N,N-dimethylformamide (0.4 mL) was added sodium hydride (60% oil dispersion, 1.7 mg, 0.042 mmol) at 0° C., and the mixture was stirred at 0° C. for 30 minutes. To the reaction mixture was added methyl iodide (2.6 μL, 0.042 mmol), then the reaction temperature was gradually elevated, the mixture was stirred at room temperature for 1 hour, then additional methyl iodide (2.6 μL, 0.042 mmol) was added thereto, and stirred at room temperature overnight. To the reaction mixture were added sodium hydride (1.7 mg, 0.042 mmol) and methyl iodide (2.6 μL, 0.042 mmol) at 0° C., then the reaction temperature was gradually elevated, the mixture was stirred at room temperature for 1 hour, then additional methyl iodide (5.2 μL, 0.084 mmol) was added thereto, and the reaction mixture was stirred at room temperature overnight. To the reaction mixture was added water, and the mixture was extracted three times with ethyl acetate. The organic layer was combined, washed twice with water, dried, and concentrated under reduced pressure. The obtained residue was dissolved in N,N-dimethylformamide (0.4 mL), then sodium hydride (1.7 mg, 0.042 mmol) was added thereto at 0° C., and the mixture was stirred at 0° C. for 30 minutes. To the mixture was added methyl iodide (5.2 μL, 0.084 mmol) at 0° C., the reaction temperature was gradually elevated, the reaction mixture was stirred at room temperature for 2 hours, then additional methyl iodide (5.2 μL, 0.084 mmol) was added thereto, and the mixture was stirred at room temperature overnight. To the reaction mixture was added an aqueous sodium hydroxide solution (2 mol/L, 57.0 μL, 0.115 mmol), and the mixture was stirred at room temperature for 3 hours. To the reaction mixture was added hydrochloric acid (2 mol/L) to acidify the reaction mixture, and the mixture was extracted three times with ethyl acetate. The organic layer was combined, washed twice with water, dried, and concentrated under reduced pressure. The obtained residue was purified by a silica gel column chromatography (hexane:ethyl acetate=50:50→0:100) to give 4-({(4-cyclopropylisoquinolin-3-yl)[4-(trifluoromethoxy)benzyl]amino}sulfonyl)-2-(methylamino)benzoic acid (7.6 mg, 35%) as a yellow solid.

APCI-MS m/z: 572 [M+H]$^+$.

Examples 42 to 60

The corresponding starting compounds were treated in a similar manner to Examples 36, 37, 38, 39, 40 and/or 41 to give the following compounds of Table 7. Interconversions of a carboxylic acid compound and a salt thereof to each other may be carried out by a conventional salt formation and a conventional desalination, respectively.

TABLE 7

| Example | Structure | Physical data |
|---|---|---|
| 42 | ![structure] | APCI-MS m/z: 575 [M + H]$^+$ |

TABLE 7-continued
| Example | Structure | Physical data |
|---|---|---|
| 43 | 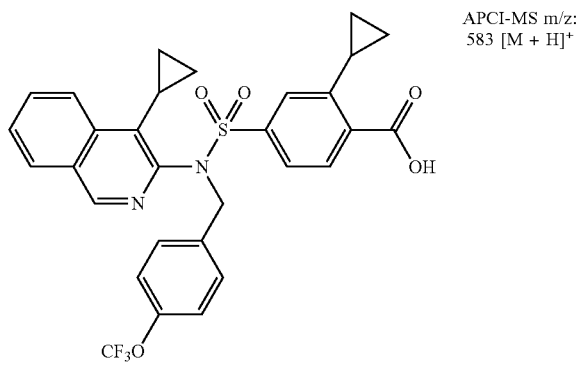 | APCI-MS m/z: 583 [M + H]+ |
| 44 | 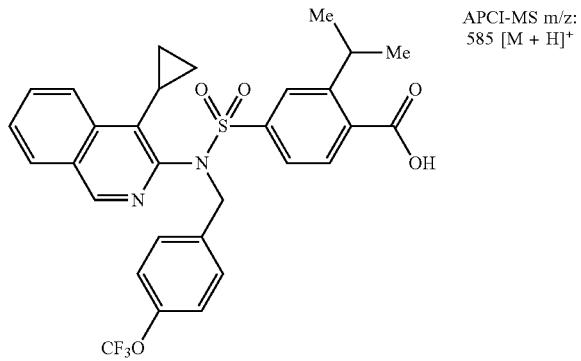 | APCI-MS m/z: 585 [M + H]+ |
| 45 | 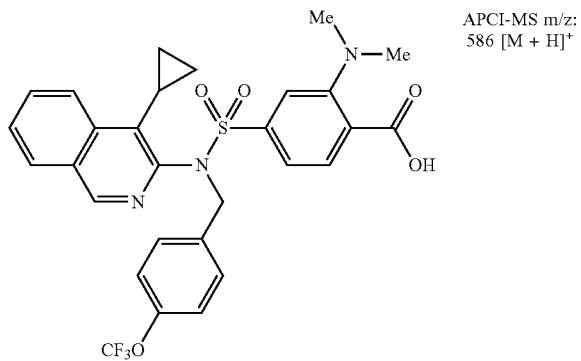 | APCI-MS m/z: 586 [M + H]+ |
| 46 | 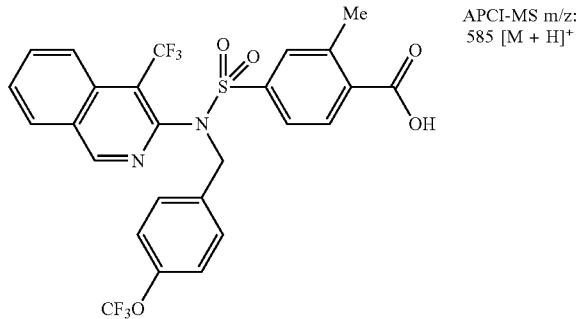 | APCI-MS m/z: 585 [M + H]+ |

TABLE 7-continued

| Example | Structure | Physical data |
|---|---|---|
| 47 | 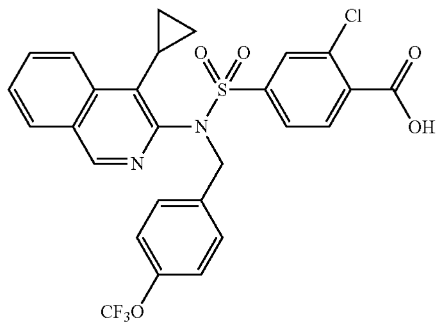 | APCI-MS m/z: 577/579 [M + H]+ |
| 48 | 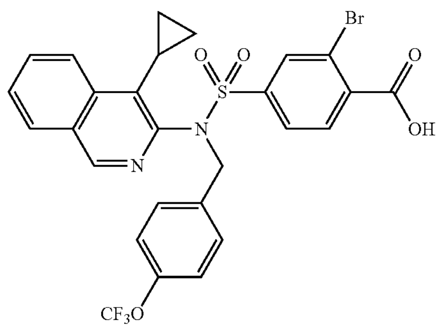 | APCI-MS m/z: 621/623 [M + H]+ |
| 49 | 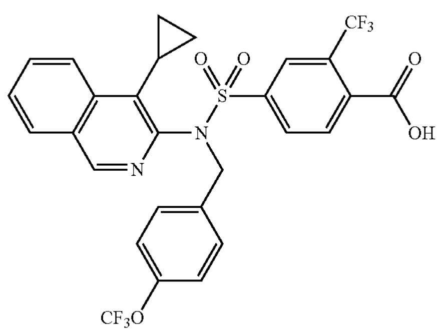 | ESI-MS m/z: 609 [M − H]− |
| 50 | 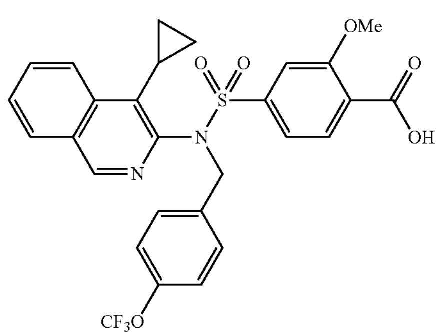 | APCI-MS m/z: 573 [M + H]+ |

TABLE 7-continued
| Example | Structure | Physical data |
|---|---|---|
| 51 | 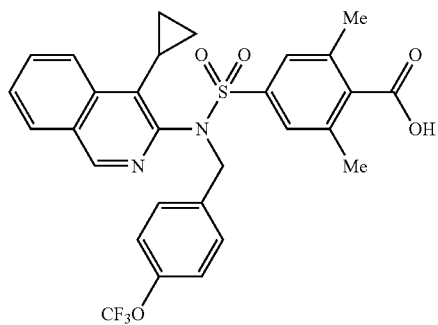 | APCI-MS m/z: 571 [M + H]+ |
| 52 | 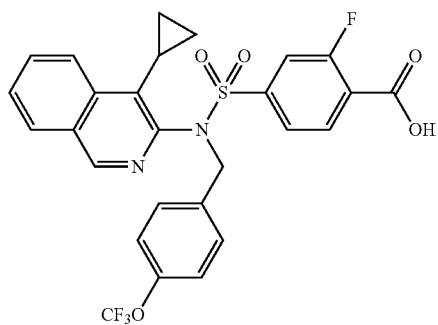 | APCI-MS m/z: 561 [M + H]+ |
| 53 | 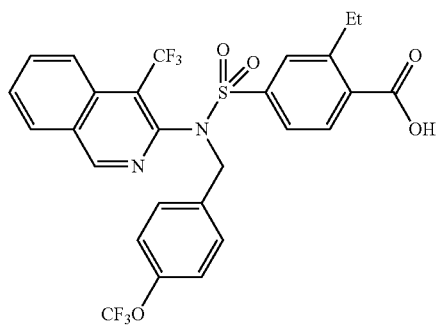 | APCI-MS m/z: 599 [M + H]+ |
| 54 | 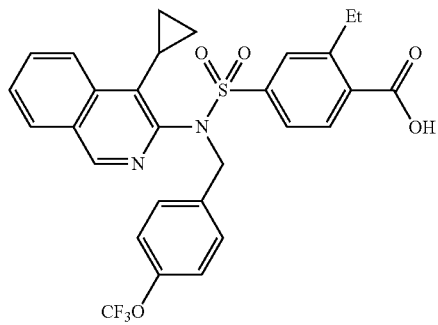 | APCI-MS m/z: 571 [M + H]+ |

TABLE 7-continued
| Example | Structure | Physical data |
|---------|-----------|---------------|
| 55 | 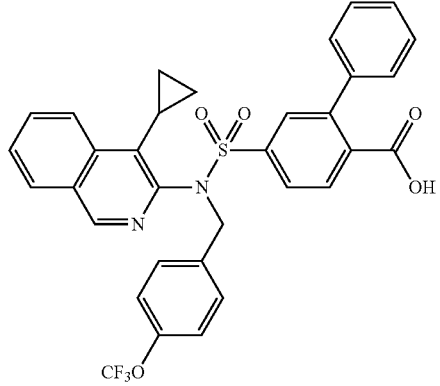 | APCI-MS m/z: 619 [M + H]⁺ |
| 56 | 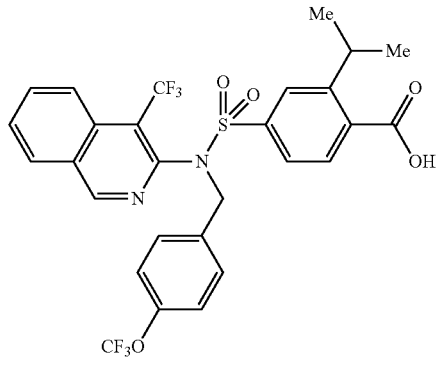 | APCI-MS m/z: 613 [M + H]⁺ |
| 57 | 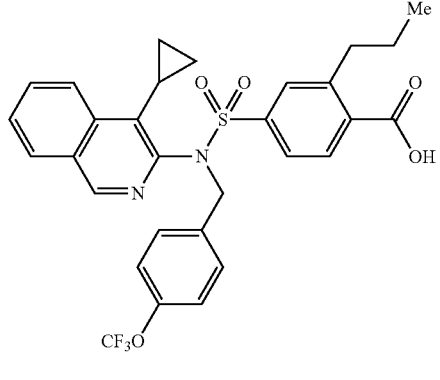 | APCI-MS m/z: 585 [M + H]⁺ |
| 58 | 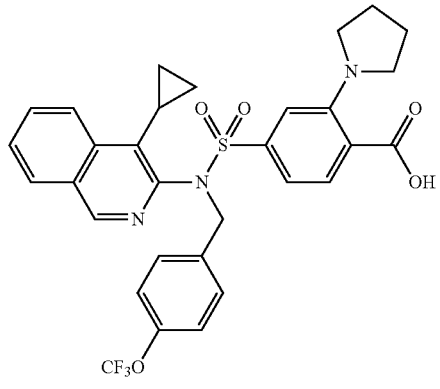 | ESI-MS m/z: 610 [M − H]⁻ |

TABLE 7-continued

| Example | Structure | Physical data |
|---------|-----------|---------------|
| 59 | 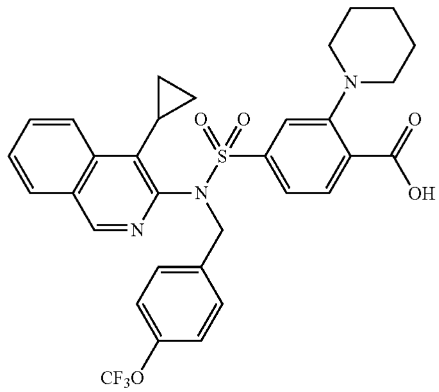 | APCI-MS m/z: 626 [M + H]+ |
| 60 | 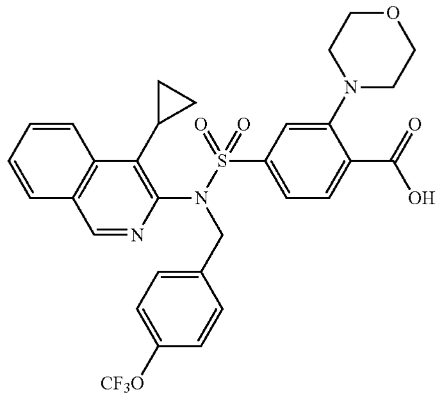 | APCI-MS m/z: 628 [M + H]+ |

Reference Example 1

Preparation of 4-cyano-N-(4-cyclopropylisoquinolin-3-yl)-N-[4-(trifluoromethoxy)benzyl]benzenesulfonamide (1) Synthesis of 4-cyano-N-(4-cyclopropylisoquinolin-3-yl)benzenesulfonamide

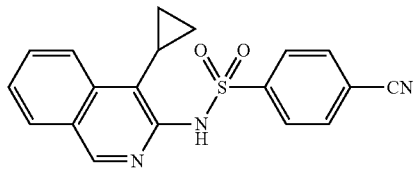 [SMILES: N#Cc1ccc(S(=O)(=O)Nc2ncc3ccccc3c2C2CC2)cc1]

A mixture of 4-cyclopropylisoquinoline-3-amine (635 mg, 3.45 mmol), 4-chlorosulfonylbenznitrile (1265 mg, 3.62 mmol), and pyridine (12 mL) was stirred at room temperature overnight, and additionally stirred at 50° C. for 5 hours. The reaction mixture was concentrated under reduced pressure, then to the residue was added 10% aqueous citric acid solution, and the mixture was extracted with ethyl acetate. The organic layer was separated, then washed with saturated saline, dried over sodium sulfate, filtered, and the filtrate was concentrated under reduced pressure. The obtained residue was purified by a silica gel column chromatography (hexane:ethyl acetate=80:20→40:60) to give 4-cyano-N-(4-cyclopropylisoquinolin-3-yl)benzenesulfonamide (279 mg, 23%) as a pale yellow solid.
APCI-MS m/z: 350 [M+H]+.

(2) Synthesis of 4-cyano-N-(4-cyclopropylisoquinolin-3-yl)-N-[4-(trifluoromethoxy)benzyl]benzenesulfonamide

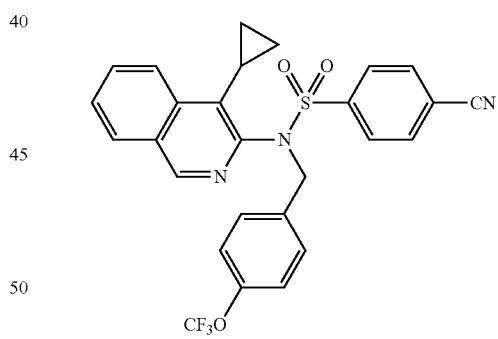

To a solution of the compound obtained in (1) (275 mg, 0.787 mmol) in N,N-dimethylformamide (4 mL) were added 4-trifluoromethoxybenzyl bromide (189 μL, 1.18 mmol) and potassium carbonate (326 mg, 2.36 mmol), and the mixture was stirred at room temperature overnight. To the reaction mixture was added ethyl acetate, then the mixture was washed with water and saturated saline, dried over sodium sulfate, filtered, and concentrated under reduced pressure. The obtained residue was purified by a silica gel column chromatography (hexane:ethyl acetate=90:10→75:25) to give 4-cyano-N-(4-cyclopropylisoquinolin-3-yl)-N-[4-(trifluoromethoxy)benzyl]benzenesulfonamide (347 mg, 84%) as a colorless solid.
APCI-MS m/z: 524 [M+H]+.

Reference Example 2

Preparation of ethyl 4-[((4-cyclopropylisoquinolin-3-yl){[5-(trifluoromethyl)pyridin-2-yl]methyl}amino)sulfonyl]benzoate (1) Synthesis of ethyl 4-{[(4-cyclopropylisoquinolin-3-yl)amino]sulfonyl}benzoate

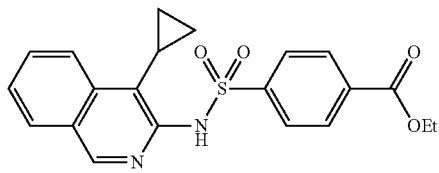 [SMILES: CCOC(=O)c1ccc(S(=O)(=O)Nc2ncc3ccccc3c2C2CC2)cc1]

A mixture of 4-cyclopropylisoquinoline-3-amine (700 mg, 3.80 mmol), 4-chlorosulfonylbenzoic acid ethyl ester (992 mg, 3.99 mmol) and pyridine (12 mL) was stirred at room temperature overnight. The reaction mixture was concentrated under reduced pressure, and to the residue were added ethyl acetate and 0.5 mol/L of hydrochloric acid. The organic layer was separated, washed with saturated saline, dried over sodium sulfate, filtered, and the filtrate was concentrated under reduced pressure. To the obtained residue was added diisopropylether, then the obtained solid was collected by filtration, and dried under reduced pressure to give ethyl 4-{[(4-cyclopropylisoquinolin-3-yl)amino]sulfonyl}benzoate (1286 mg, 85%) as a brown solid.

APCI-MS m/z: 397 [M+H]$^+$.

(2) Synthesis of ethyl 4-[((4-cyclopropylisoquinolin-3-yl){[5-(trifluoromethyl)pyridin-2-yl]methyl}amino)sulfonyl]benzoate

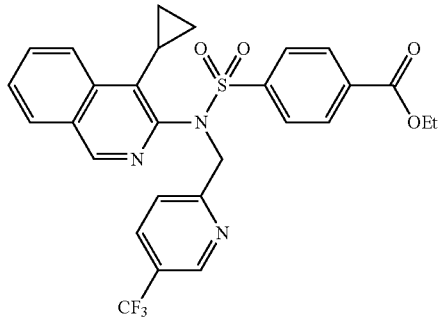 [SMILES: CCOC(=O)c1ccc(S(=O)(=O)N(Cc2ccc(C(F)(F)F)cn2)c2ncc3ccccc3c2C2CC2)cc1]

To a solution of the compound obtained in (1) (888 mg, 2.24 mmol), 2-hydroxymethyl-5-trifluoromethylpyridine (515 mg, 2.91 mmol), and triphenylphosphine (881 mg, 3.36 mmol) in tetrahydrofuran (20 mL) was added diethylazodicarboxylate (2.2 mol/L solution in toluene, 1527 μL, 3.36 mmol) at 0° C., then the reaction temperature was gradually elevated, and the reaction was stirred at room temperature overnight. The reaction mixture was concentrated under reduced pressure, and the obtained residue was purified by a silica gel column chromatography (hexane:ethyl acetate=85:15→65:35) to give ethyl 4-[((4-cyclopropylisoquinolin-3-yl){[5-(trifluoromethyl)pyridin-2-yl]methyl}amino)sulfonyl]benzoate (1144 mg, 92%) as a white viscous material.

APCI-MS m/z: 556 [M+H]$^+$.

Reference Example 3

Preparation of ethyl 4-({(4-cyclopropylisoquinolin-3-yl)[4-(trifluoromethoxy)benzyl]amino}sulfonyl)benzoate (1) Synthesis of ethyl 4-({(4-iodoisoquinolin-3-yl)[4-(trifluoromethoxy)benzyl]amino}sulfonyl)benzoate

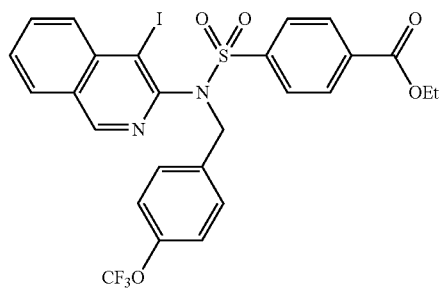

A mixture of 3-aminoisoquinoline (26.5 g, 0.175 mol) and 4-chlorosulfonylbenzoic acid ethyl ester (43.5 g, 0.175 mol) in pyridine (530 mL) was stirred at room temperature for 4 hours. The reaction mixture was added to water (1.5 L), and the precipitate was collected by filtration. The obtained solid was washed with water, and dried under reduced pressure to give a pink solid (53.6 g).

The obtained solid was suspended in acetic acid (55 mL) and N,N-dimethylformamide (330 mL), and heated to 50° C. To the reaction mixture was added N-iodosuccinimide (37.2 g, 0.165 mol), and the mixture was stirred at the same temperature for 15 minutes. After cooled to room temperature, to the reaction mixture were added ethyl acetate and water, and then added an aqueous sodium bicarbonate to neutralize the mixture. The obtained precipitate was collected by filtration, washed with water, and dried under reduced pressure to give a white solid (43.7 g). The organic layer of the filtrate was separated, washed with water and saturated saline, dried over sodium sulfate, filtered, and the filtrate was concentrated under reduced pressure. To the residue was added ethyl acetate, the obtained solid was collected by filtration, and dried under reduced pressure to give a pale brown solid (25.7 g).

The obtained solid was combined, dissolved in N,N-dimethylformamide (590 mL), then 4-trifluoromethoxybenzyl bromide (44.0 g, 0.173 mol) and potassium carbonate (29.8 g, 0.216 mol) were added thereto, and the mixture was stirred at 50° C. for 3 hours. After cooled to room temperature, to the reaction mixture was added ethyl acetate, the mixture was washed with water and saturated saline, dried over sodium sulfate, filtered, and the filtrate was concentrated under reduced pressure. To the residue was added diisopropylether, the obtained solid was collected by filtration, and dried under reduced pressure to give ethyl 4-({(4-iodoisoquinolin-3-yl)[4-(trifluoromethoxy)benzyl]amino}sulfonyl)benzoate (90.8 g, 78%) as a yellow solid.

APCI-MS m/z: 657 [M+H]$^+$.

(2) Synthesis of ethyl 4-({(4-cyclopropylisoquino-lin-3-yl)[4-(trifluoromethoxy)benzyl]amino}sulfonyl)benzoate

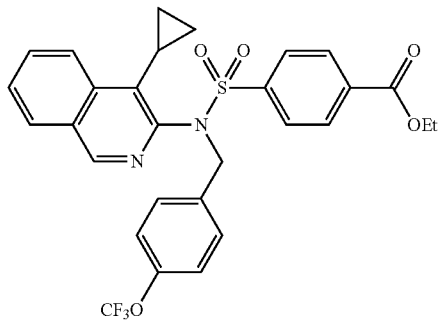

Under argon atmosphere, the compound obtained in (1) (40.0 g, 60.9 mmol), cyclopropylboronic acid (15.7 g, 183 mmol), palladium acetate (1.40 g, 6.11 mmol), tricyclohexylphosphine (3.42 g, 12.2 mmol), and tripotassium phosphate (45.3 g, 213 mmol) in a mixed solution of toluene (340 mL) and water (17 mL) were stirred at 100° C. for 3.5 hours. After cooled to room temperature, to the reaction mixture were added ethyl acetate and water, and the insoluble material was filtered off. The organic layer of the filtrate was separated, washed with water and saturated saline, dried over sodium sulfate, filtered, and the filtrate was concentrated under reduced pressure. To the residue was added diisopropylether, and the obtained solid was collected by filtration. The obtained solid was dissolved in ethanol and ethyl acetate by heating, and active carbon was added thereto. The insoluble material was filtered off, and the filtrate was gradually cooled to room temperature. The obtained precipitate was collected by filtration, washed with diisopropylether, and dried under reduced pressure to give ethyl 4-({(4-cyclopropylisoquinolin-3-yl)[4-(trifluoromethoxy)benzyl]amino}sulfonyl)benzoate (27.1 g, 77%) as a pale brown solid. Further, the filtrate was concentrated under reduced pressure, and the obtained residue was purified by a silica gel column chromatography (hexane:ethyl acetate=95:5→60:40) to give ethyl 4-({(4-cyclopropylisoquinolin-3-yl)[4-(trifluoromethoxy)benzyl]amino}sulfonyl)benzoate (3.31 g, 10%) as a colorless solid.

APCI-MS m/z: 571 [M+H]$^+$.

Reference Example 4

Preparation of 4-cyano-N-[4-(trifluoromethoxy)benzyl]-N-[4-(trifluoromethyl)isoquinolin-3-yl]benzenesulfonamide (1) Synthesis of ethyl 4-({[4-(trifluoromethoxy)benzyl][4-(trifluoromethyl)isoquinolin-3-yl]amino}sulfonyl)benzoate

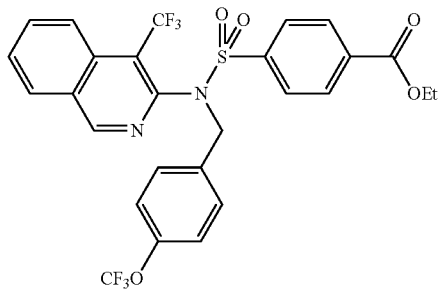

Under argon atmosphere, a mixture of ethyl 4-({(4-iodoisoquinolin-3-yl)[4-(trifluoromethoxy)benzyl]amino}sulfonyl)benzoate obtained in Reference Example 3-(1) (978 mg, 1.49 mmol), methyl 2,2-difluoro-2-(fluorosulfonyl)acetate (2.86 g, 14.9 mmol), copper(I) iodide (2.84 g, 14.9 mmol), and hexamethylphosphorictriamide (2.67 g, 14.9 mmol) in N,N-dimethylformamide (8 mL) was stirred at 70° C. for 5 hours. After cooled to room temperature, to the reaction mixture were added ethyl acetate and water, and the insoluble material was filtered off. The organic layer of the filtrate was separated, washed with water and saturated saline, dried over sodium sulfate, filtered, and the filtrate was concentrated under reduced pressure. To the residue were added ethyl acetate and hexane, then the obtained solid was collected by filtration, and dried under reduced pressure to give ethyl 4-({[4-(trifluoromethoxy)benzyl][4-(trifluoromethyl)isoquinolin-3-yl]amino}sulfonyl)benzoate (804 mg, 90%) as a white solid.

APCI-MS m/z: 599 [M+H]$^+$.

(2) Synthesis of sodium 4-({[4-(trifluoromethoxy)benzyl][4-(trifluoromethyl)isoquinolin-3-yl]amino}sulfonyl)benzoate

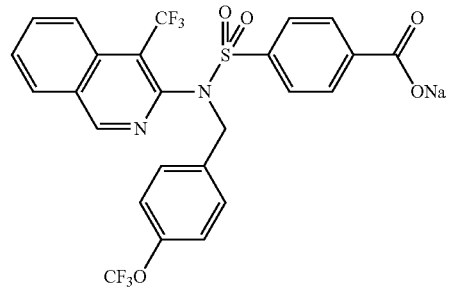

To a solution of the compound obtained in (1) (772 mg, 1.29 mmol) in ethanol (5 mL) and tetrahydrofuran (5 mL) was added an aqueous sodium hydroxide solution (2 mol/L, 1.29 mL, 2.58 mmol), and the mixture was stirred at room temperature for 1 hour. The reaction mixture was concentrated under reduced pressure, to the residue was added 10% aqueous citric acid solution to acidify the mixture, and then the mixture was extracted with ethyl acetate. The organic layer was washed with water and saturated saline, dried over sodium sulfate, filtered, and the filtrate was concentrated under reduced pressure. The obtained residue was dissolved in ethanol (10 mL), then an aqueous sodium hydroxide solution (1 mol/L, 1.25 mL, 1.25 mmol) was added thereto, and the mixture was concentrated under reduced pressure. To the residue were added ethanol and pentane, then the obtained solid was collected by filtration, and dried under reduced pressure to give sodium 4-({[4-(trifluoromethoxy)benzyl][4-(trifluoromethyl)isoquinolin-3-yl]amino}sulfonyl)benzoate (704 mg, 93%) as a white solid.

ESI-MS m/z: 569 [M−Na]$^-$.

(3) Synthesis of 4-({[4-(trifluoromethoxy)benzyl][4-(trifluoromethyl)isoquinolin-3-yl]amino}sulfonyl)benzamide

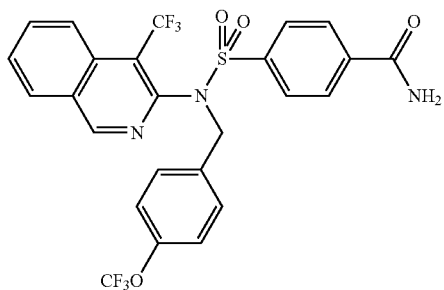

To a solution of the compound obtained in (2) (500.0 mg, 0.844 mmol) in tetrahydrofuran (10.0 mL) were added oxalyl chloride (147 μL, 1.688 mmol) and N,N-dimethylformamide (2 drops), and the mixture was stirred at room temperature for 2 hours. Additional oxalyl chloride (73.5 μL, 0.844 mmol) was added thereto, and the reaction mixture was stirred at room temperature overnight. Additional oxalyl chloride (73.5 μL, 0.844 mmol) was added thereto, and the reaction mixture was stirred at room temperature for 3 hours. To the reaction mixture was added an aqueous ammonia (10.0 mL), the mixture was stirred at room temperature for 3 hours, then water was added thereto, and the mixture was extracted three times with chloroform. The organic layer was combined and dried, and concentrated under reduced pressure. The obtained residue was purified by a silica gel column chromatography (hexane:ethyl acetate=60:40→0:100) to give 4-({[4-(trifluoromethoxy)benzyl][4-(trifluoromethyl)isoquinolin-3-yl]amino}sulfonyl)benzamide (386.0 mg, 80%) as a white solid.

APCI-MS m/z: 570 [M+H]$^+$.

(4) Synthesis of 4-cyano-N-[4-(trifluoromethoxy)benzyl]-N-[4-(trifluoromethyl)isoquinolin-3-yl]benzenesulfonamide

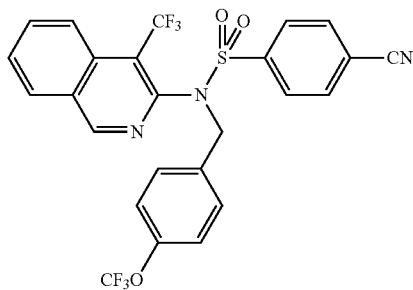

To a solution of the compound obtained in (3) (385.0 mg, 0.676 mmol) in methylene chloride (3.4 mL) were added triethylamine (376.9 μL, 2.704 mmol) and trifluoroacetic acid anhydride (191.0 μL, 1.352 mmol), and the mixture was stirred at room temperature overnight. To the reaction mixture was added water, and the mixture was extracted three times with chloroform. The organic layer was combined and dried, and concentrated under reduced pressure. The obtained residue was purified by a silica gel column chromatography (hexane:ethyl acetate=100:0→70:30) to give 4-cyano-N-[4-(trifluoromethoxy)benzyl]-N-[4-(trifluoromethyl)isoquinolin-3-yl]benzenesulfonamide (352.0 mg, 94%) as a pale yellow solid.

APCI-MS m/z: 552 [M+H]$^+$.

Reference Example 5

Preparation of ethyl 4-({(1-cyclopropyl-4-methylisoquinolin-3-yl)[4-(trifluoromethoxy)benzyl]amino}sulfonyl)benzoate

(1) Synthesis of ethyl 4-({(1-bromo-4-methylisoquinolin-3-yl)[4-(trifluoromethoxy)benzyl]amino}sulfonyl)benzoate

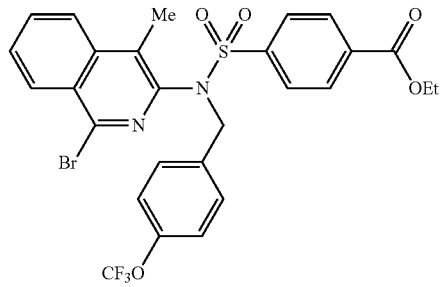

1-Bromo-4-methylisoquinoline-3-amine, ethyl 4-chlorosulfonylbenzoate, and 1-(bromomethyl)-4-(trifluoromethoxy)benzene were treated in a similar manner to Reference Examples 1-(1) and (2) to give ethyl 4-({(1-bromo-4-methylisoquinolin-3-yl)[4-(trifluoromethoxy)benzyl]amino}sulfonyl)benzoate as a colorless solid.

APCI-MS m/z: 623/625 [M+H]$^+$.

(2) Synthesis of ethyl 4-({(1-cyclopropyl-4-methylisoquinolin-3-yl)[4-(trifluoromethoxy)benzyl]amino}sulfonyl)benzoate

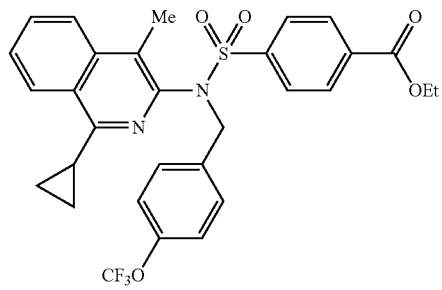

A mixture of the compound obtained in (1) (100 mg, 160 μmol), cyclopropyltrifluoroborate potassium salt (45.9 mg, 321 μmol), palladium acetate (3.7 mg, 16.0 μmol), di(1-adamantyl)butylphosphine (9.1 mg, 24.1 μmol), and cesium carbonate (105 mg, 321 μmol) in water (80 μL) and toluene (802 μL) was heated under reflux for 3 hours under argon atmosphere. After cooling, the reaction mixture was diluted with ethyl acetate, filtered through diatomaceous earth, and concentrated under reduced pressure. The obtained residue was purified by a silica gel column chromatography (hexane:ethyl acetate=19:1→47:3) to give ethyl 4-({(1-cyclopropyl-4-methylisoquinolin-3-yl)[4-(trifluoromethoxy)benzyl]amino}sulfonyl)benzoate (93.0 mg, 99%) as a pale yellow solid.

APCI-MS m/z: 585 [M+H]$^+$, $^1$H-NMR (DMSO-d$_6$) δ 0.25-0.95 (4H, m), 1.37 (3H, t, J=7.3 Hz), 2.38 (3H, s), 2.73-2.82 (1H, m), 4.40 (2H, q, J=7.3 Hz), 4.46-5.12 (2H, m), 7.20 (2H, d, J=8.2 Hz), 7.26

(2H, d, J=8.8 Hz), 7.69-7.75 (1H, m), 7.77-7.84 (3H, m), 8.01 (1H, d, J=8.2 Hz), 8.14 (2H, d, J=8.5 Hz), 8.49 (1H, d, J=8.2 Hz).

Reference Example 6

Preparation of 6-cyano-N-(4-cyclopropylisoquinolin-3-yl)-N-[4-(trifluoromethoxy)benzyl]pyridine-3-sulfonamide (1) Synthesis of 6-chloro-N-(4-cyclopropylisoquinolin-3-yl)pyridine-3-sulfonamide

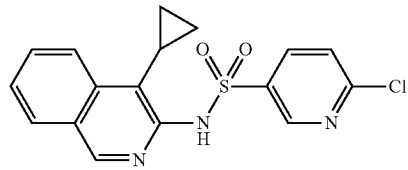 [SMILES: O=S(=O)(Nc1ncc2ccccc2c1C1CC1)c1ccc(Cl)nc1]

4-Cyclopropylisoquinoline-3-amine and 2-chloro-5-chlorosulfonylpyridine were treated in a similar manner to Reference Example 1-(1) to give 6-chloro-N-(4-cyclopropylisoquinolin-3-yl)pyridine-3-sulfonamide.
APCI-MS m/z: 360/362 [M+H]+.

(2) Synthesis of 6-chloro-N-(4-cyclopropylisoquinolin-3-yl)-N-[4-(trifluoromethoxy)benzyl]pyridine-3-sulfonamide

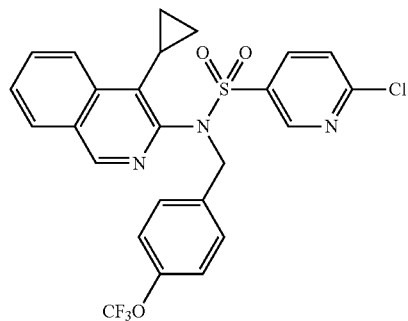

The compound obtained in (1) and 4-trifluoromethoxybenzyl bromide were treated in a similar manner to Reference Example 1-(2) to give 6-chloro-N-(4-cyclopropylisoquinolin-3-yl)-N-[4-(trifluoromethoxy)benzyl]pyridine-3-sulfonamide.
APCI-MS m/z: 534/536 [M+H]+.

(3) Synthesis of 6-cyano-N-(4-cyclopropylisoquinolin-3-yl)-N-[4-(trifluoromethoxy)benzyl]pyridine-3-sulfonamide

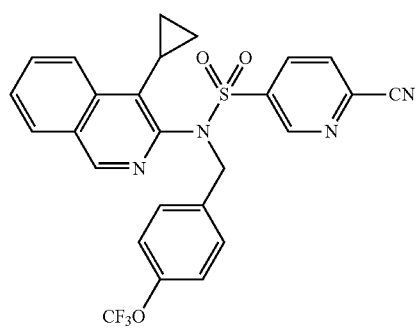

A mixture of the compound obtained in (2) (300 mg, 0.562 mmol), zinc(II) cyanide (63 mg, 0.537 mmol), and tetrakistriphenylphosphinepalladium(0) (71.4 mg, 0.0618 mmol) in N,N-dimethylformamide (7 mL) was stirred at 175° C. for 5 minutes under argon atmosphere and under microwave irradiation. To the reaction mixture was added ethyl acetate, and the mixture was washed with aqueous saturated sodium bicarbonate, water, and saturated saline. The organic layer was dried over sodium sulfate, filtered, and the filtrate was concentrated under reduced pressure. The obtained brown oil was purified by a silica gel column chromatography (hexane:ethyl acetate=90:10→75:25) to give 6-cyano-N-(4-cyclopropylisoquinolin-3-yl)-N-[4-(trifluoromethoxy)benzyl]pyridine-3-sulfonamide (261 mg, 89%) as a colorless solid.
APCI-MS m/z: 525 [M+H]+.

Reference Example 7

Preparation of methyl 4-({(4-cyclopropylisoquinolin-3-yl)[4-(trifluoromethoxy)benzyl]amino}sulfonyl)-2-fluorobenzoate (1) Synthesis of 4-bromo-N-(4-cyclopropylisoquinolin-3-yl)-3-fluorobenzenesulfonamide

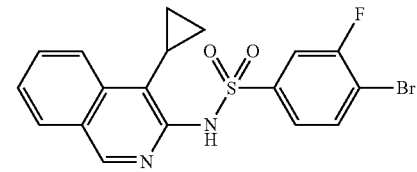 [SMILES: O=S(=O)(Nc1ncc2ccccc2c1C1CC1)c1ccc(Br)c(F)c1]

4-Cyclopropylisoquinoline-3-amine and 4-bromo-3-fluorobenzenesulfonyl chloride were treated in a similar manner to Reference Example 1-(1) to give 4-bromo-N-(4-cyclopropylisoquinolin-3-yl)-3-fluorobenzenesulfonamide.
APCI-MS m/z: 421/423 [M+H]+.

(2) Synthesis of 4-bromo-N-(4-cyclopropylisoquinolin-3-yl)-3-fluoro-N-[4-(trifluoromethoxy)benzyl]benzenesulfonamide

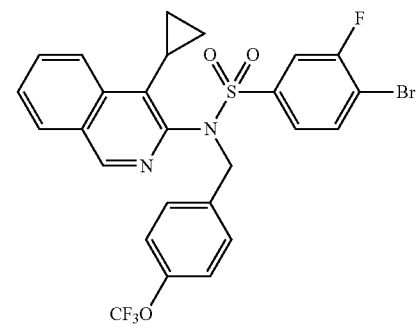

The compound obtained in (1) and 4-trifluoromethoxybenzyl bromide were treated in a similar manner to Reference Example 1-(2) to give 4-bromo-N-(4-cyclopropylisoquinolin-3-yl)-3-fluoro-N-[4-(trifluoromethoxy)benzyl]benzenesulfonamide.
APCI-MS m/z: 595/597 [M+H]+.

(3) Synthesis of methyl 4-({(4-cyclopropylisoquino-lin-3-yl)[4-(trifluoromethoxy)benzyl]amino}sulfonyl)-2-fluorobenzoate

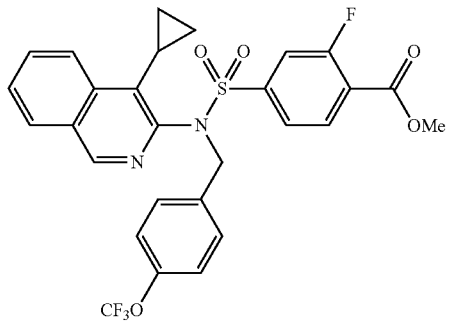

A mixture of the compound obtained in (2) (908 mg, 1.53 mmol), tri-t-butylphosphine tetrafluoroborate (97.3 mg, 0.335 mmol), trans-di(μ-acetato)bis[o-(di-o-tolylphosphino)benzyl]dipalladium(II) (157 mg, 0.167 mmol), molybdenum hexacarbonyl (523 mg, 1.98 mmol), and 1,8-diazabicyclo[5.4.0]undec-7-ene (232 mg, 1.52 mmol) in methanol (13.5 mL) and acetonitrile (4.5 mL) was stirred at 140° C. for 30 minutes under microwave irradiation. After cooling, to the reaction mixture were added ethyl acetate and water, and the mixture was filtered through diatomaceous earth. The organic layer was separated, washed with water, dried over sodium sulfate, filtered, and the filtrate was concentrated under reduced pressure. The obtained residue was purified by a silica gel column chromatography (hexane:ethyl acetate=95:5→80:20) to give methyl 4-({(4-cyclopropylisoquinolin-3-yl)[4-(trifluoromethoxy)benzyl]amino}sulfonyl)-2-fluorobenzoate (415 mg, 47%) as a colorless solid.

APCI-MS m/z: 575 [M+H]$^+$.

Reference Example 8

Preparation of 4-cyclopropylisoquinoline-3-amine (1) Synthesis of 4-bromoisoquinoline-3-amine

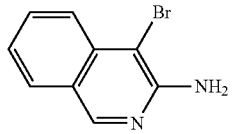 [SMILES: Nc1ncc2ccccc2c1Br]

To a solution of 3-aminoisoquinoline (4.00 g, 27.7 mmol) in ethanol (40 mL) and methylene chloride (80 mL) was added N-bromosuccinimide (5.18 g, 29.1 mmol) in divided portions at 5° C., then the mixture was stirred at 5° C. for 2 hours and 20 minutes, and stirred at room temperature overnight. The reaction mixture was concentrated under reduced pressure, and the obtained brown residue was purified by a silica gel column chromatography (hexane:ethyl acetate=50:50, hexane:ethyl acetate=85:15→70:30, hexane:ethyl acetate=90:10→75:25) to give 4-bromoisoquinoline-3-amine (4.65 g, 75%) as a pale yellow solid.

APCI-MS m/z: 223/225 [M+H]$^+$.

(2) Synthesis of 4-cyclopropylisoquinoline-3-amine

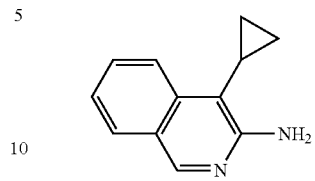

A mixture of the compound obtained in (1) (5.74 g, 25.7 mmol), cyclopropylboronic acid (6.63 g, 77.2 mmol), tricyclohexylphosphine (1.44 g, 5.13 mmol), palladium(II) acetate (578 mg, 2.57 mmol), and tripotassium phosphate (19.1 g, 90.0 mmol) in toluene (130 mL) and water (6.5 mL) was stirred at 100° C. for 4 hours under argon atmosphere. To the reaction mixture were added water and ethyl acetate, insoluble material was filtered off, and the filtrate was washed with saturated saline. The organic layer was dried over sodium sulfate, filtered, and the filtrate was concentrated under reduced pressure. The obtained brown oil was purified by an NH silica gel column chromatography (hexane:chloroform=70:30→0:100). The obtained yellow solid was suspended in a mixed solvent of ethyl acetate and diisopropylether, stirred, and then collected by filtration to give 4-cyclopropylisoquinoline-3-amine (3.11 g, 66%) as a pale yellow solid.

APCI-MS m/z: 185 [M+H]$^+$.

Reference Example 9

Preparation of 4-(trifluoromethyl)isoquinoline-3-amine

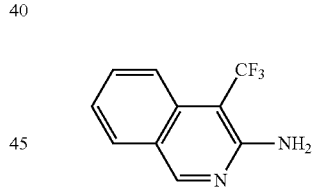

A mixture of 1-trifluoromethyl-3,3-dimethyl-1,2-benziodoxole (2.75 g, 8.32 mmol), tris(trimethylsilyl)silylchloride (2.36 g, 8.32 mmol), and 3-aminoisoquinoline (1.0 g, 6.94 mmol) in acetonitrile (35 mL) was stirred at 80° C. for 50 minutes. After cooled to room temperature, the reaction mixture was concentrated under reduced pressure. The obtained residue was purified by a silica gel column chromatography (hexane:ethyl acetate=98:2→80:20) to give 4-(trifluoromethyl)isoquinoline-3-amine (737 mg, 50%) as a yellow solid.

APCI-MS m/z: 213 [M+H]$^+$.

Reference Example 10

The corresponding starting compound was treated in a similar manner to Reference Example 2 to give the following compound of Table 8.

TABLE 8

| Reference Example | Structure | Physical data |
|---|---|---|
| 10 | [structure] | APCI-MS m/z: 509 [M + H]+ |

Reference Example 11

The corresponding starting compound was treated in a similar manner to Reference Example 3-(1), Reference Example 4-(1), and Reference Example 6 to Give the Following compound of Table 9.

TABLE 9

| Reference Example | Structure | Physical data |
|---|---|---|
| 11 | [structure] | APCI-MS m/z: 553 [M + H]+ |

Reference Examples 12 and 13

The corresponding starting compounds were treated in a similar manner to Reference Examples 4-(2), (3), and (4) to give the following compounds of Table 10.

TABLE 10

| Reference Example | Structure | Physical data |
|---|---|---|
| 12 | [structure] | APCI-MS m/z: 538 [M + H]+ |
| 13 | [structure] | APCI-MS m/z: 538 [M + H]+ |

Reference Example 14

The corresponding starting compound was treated in a similar manner to Reference Example 6 to give the following compound of Table 11.

TABLE 11

| Reference Example | Structure | Physical data |
|---|---|---|
| 14 | [structure] | APCI-MS m/z: 525 [M + H]+ |

Reference Example 15

Preparation of methyl 4-({(4-cyclopropylisoquino-lin-3-yl)[4-(trifluoromethoxy)benzyl]amino}sulfonyl)-2-methylbenzoate (1) Synthesis of methyl 4-{[(4-cyclopropylisoquino-lin-3-yl)amino]sulfonyl}-2-methylbenzoate

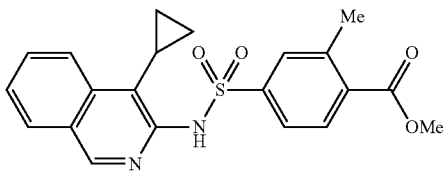 [SMILES: COC(=O)c1ccc(S(=O)(=O)Nc2ncc3ccccc3c2C2CC2)cc1C]

To a solution of 4-methoxycarbonyl-3-methylbenzenesulfonyl chloride (405 mg, 1.63 mmol) in pyridine (5 mL) was added 3-amino-4-cyclopropylisoquinoline (300 mg, 1.63 mmol) at 5° C. The reaction temperature was gradually elevated, and the reaction mixture was stirred at room temperature overnight. The reaction mixture was concentrated under reduced pressure, toluene was added thereto to carry out azeotropy, then ethyl acetate was added thereto, and the mixture was poured into 10% aqueous citric acid solution. The organic layer was separated, washed with 10% aqueous citric acid solution and saturated saline, dried over magnesium sulfate, filtered, and the filtrate was concentrated. The obtained red oil was purified by a silica gel column chromatography (hexane:ethyl acetate=95:5→85:15) to give methyl 4-{[(4-cyclopropylisoquinolin-3-yl)amino]sulfonyl}-2-methylbenzoate (529 mg, 82%) as a yellow solid.

APCI-MS m/z: 397 [M+H]$^+$.

(2) Synthesis of methyl 4-({(4-cyclopropylisoquino-lin-3-yl)[4-(trifluoromethoxy)benzyl]amino}sulfonyl)-2-methylbenzoate

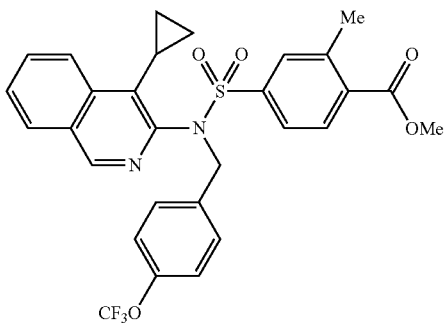

To a solution of the compound obtained in (1) (306 mg, 0.927 mmol) in N,N-dimethylformamide (5 mL) were added potassium carbonate (128 mg, 0.811 mmol) and 4-trifluoromethoxybenzyl bromide (207 mg, 0.811 mmol) at 5° C. The reaction temperature was gradually elevated, and the reaction mixture was stirred at room temperature overnight. To the reaction mixture was added ethyl acetate, the mixture was poured into saturated saline, and extracted with ethyl acetate. The organic layer was dried over magnesium sulfate, filtered, and the filtrate was concentrated under reduced pressure. The obtained yellow oil was purified by a silica gel column chromatography (hexane:ethyl acetate=100:0→80:20) to give methyl 4-({(4-cyclopropylisoquinolin-3-yl)[4-(trifluoromethoxy)benzyl]amino}sulfonyl)-2-methylbenzoate (417 mg, 95%) as a white solid.

APCI-MS m/z: 571 [M+H]$^+$.

Reference Example 16

Preparation of methyl 4-[((4-cyclopropylisoquino-lin-3-yl){[5-(trifluoromethyl)pyridin-2-yl]methyl}amino)sulfonyl]-2-methylbenzoate

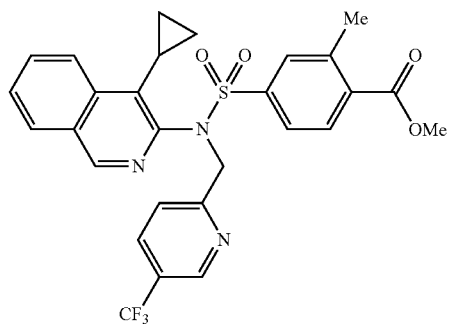 [SMILES: COC(=O)c1ccc(S(=O)(=O)N(Cc2ccc(C(F)(F)F)cn2)c2ncc3ccccc3c2C2CC2)cc1C]

To a solution of methyl 4-{[(4-cyclopropylisoquinolin-3-yl)amino]sulfonyl}-2-methylbenzoate obtained in Reference Example 15-(1) (100 mg, 0.252 mmol), 2-hydroxymethyl-5-trifluoromethylpyridine (53.6 mg, 0.303 mmol), and triphenylphosphine (99.2 mg, 0.378 mmol) in tetrahydrofuran (3 mL) was added diethylazodicarboxylate (2.2 mol/L solution in toluene, 172 μL, 0.378 mmol) at 5° C. The reaction temperature was gradually elevated, and the reaction mixture was stirred at room temperature overnight. The reaction mixture was concentrated under reduced pressure, and the obtained residue was purified by a silica gel column chromatography (hexane:ethyl acetate=100:0→80:20) to give methyl 4-[((4-cyclopropylisoquinolin-3-yl){[5-(trifluoromethyl)pyridin-2-yl]methyl}amino)sulfonyl]-2-methylbenzoate (110 mg, 78%) as a white solid.

APCI-MS m/z: 556 [M+H]$^+$.

Reference Example 17

Preparation of methyl 4-({(4-cyclopropylisoquino-lin-3-yl)[4-(trifluoromethoxy)benzyl]amino}sulfonyl)-3-methylbenzoate (1) Synthesis of 4-bromo-N-(4-cyclopropylisoqui-nolin-3-yl)-2-methylbenzenesulfonamide

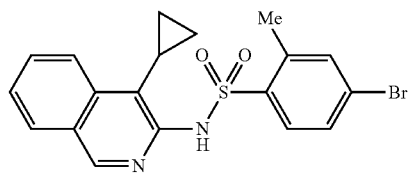 [SMILES: Cc1cc(Br)ccc1S(=O)(=O)Nc1ncc2ccccc2c1C1CC1]

To a solution of 3-amino-4-cyclopropylisoquinoline (250 mg, 1.36 mmol) in pyridine (5 mL) was added 4-bromo-2-methylbenzenesulfonyl chloride (366 mg, 1.36 mmol) at 5° C. The reaction temperature was gradually elevated, and the reaction mixture was stirred at room temperature overnight. The reaction mixture was concentrated under reduced pressure, toluene was added thereto to carry out azeotropy, ethyl acetate was added thereto, and the mixture was poured into 10% aqueous citric acid solution. The organic layer was separated, washed with 10% aqueous citric acid solution and saturated saline, dried over magnesium sulfate, filtered, and the filtrate was concentrated to give a crude product of 4-bromo-N-(4-cyclopropylisoquinolin-3-yl)-2-methylbenzenesulfonamide (515 mg) as a red solid. The resultant was used in the next step without further purification.

APCI-MS m/z: 417/419 [M+H]$^+$.

(2) Synthesis of 4-bromo-N-(4-cyclopropylisoquinolin-3-yl)-2-methyl-N-[4-(trifluoromethoxy)benzyl]benzenesulfonamide

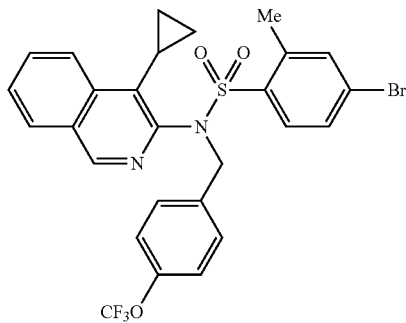

The crude product obtained in (1) (400 mg) and 4-trifluoromethoxybenzyl bromide were treated in a similar manner to Reference Example 15-(2) to give 4-bromo-N-(4-cyclopropylisoquinolin-3-yl)-2-methyl-N-[4-(trifluoromethoxy)benzyl]benzenesulfonamide (443 mg, yield for two steps: 71%) as a white solid.

APCI-MS m/z: 591/593 [M+H]$^+$.

(3) Synthesis of methyl 4-({(4-cyclopropylisoquinolin-3-yl)[4-(trifluoromethoxy)benzyl]amino}sulfonyl)-3-methylbenzoate

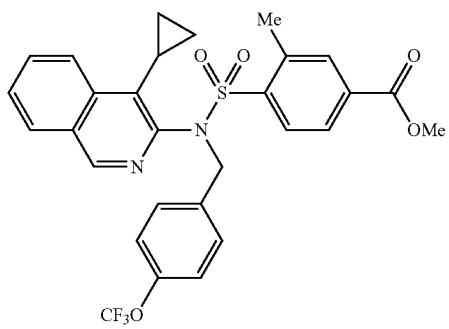

A mixture of the compound obtained in (2) (100 mg, 0.169 mmol), tri-t-butylphosphine tetrafluoroborate (10.8 mg, 0.037 mmol), trans-di(μ-acetato)bis[o-(di-o-tolylphosphino)benzyl]dipalladium(II) (17.4 mg, 0.019 mmol), molybdenum hexacarbonyl (45.1 mg, 0.17 mmol), and 1,8-diazabicyclo[5.4.0]undec-7-ene (25.5 μL, 0.17 mmol) in methanol (3 mL) and acetonitrile (1 mL) was stirred at 145° C. for 30 minutes under microwave irradiation. After cooling, the reaction mixture was filtered using diatomaceous earth, the diatomaceous earth was washed with methanol, and the filtrate was concentrated under reduced pressure. The obtained residue was purified by a silica gel column chromatography (hexane:ethyl acetate=100:0→80:20) to give methyl 4-({(4-cyclopropylisoquinolin-3-yl)[4-(trifluoromethoxy)benzyl]amino}sulfonyl)-3-methylbenzoate (67.5 mg, 70%) as a white solid.

APCI-MS m/z: 571 [M+H]$^+$.

Reference Example 18

Preparation of methyl 4-({(4-cyclopropylisoquinolin-3-yl)[4-(trifluoromethoxy)benzyl]amino}sulfonyl)-2-fluoro-6-methylbenzoate (1) Synthesis of 4-bromo-N-(4-cyclopropylisoquinolin-3-yl)-3-fluoro-5-methylbenzenesulfonamide

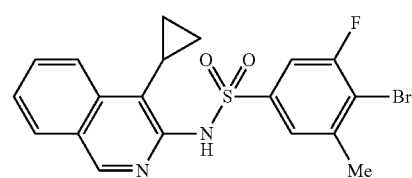 [SMILES: Cc1cc(S(=O)(=O)Nc2ncc3ccccc3c2C2CC2)cc(F)c1Br]

4-Cyclopropylisoquinoline-3-amine and 4-bromo-3-fluoro-5-methylbenzenesulfonyl chloride were treated in a similar manner to Reference Example 17-(1) to give 4-bromo-N-(4-cyclopropylisoquinolin-3-yl)-3-fluoro-5-methylbenzenesulfonamide.

APCI-MS m/z: 435/437 [M+H]$^+$.

(2) Synthesis of 4-bromo-N-(4-cyclopropylisoquinolin-3-yl)-3-fluoro-5-methyl-N-[4-(trifluoromethoxy)benzyl]benzenesulfonamide

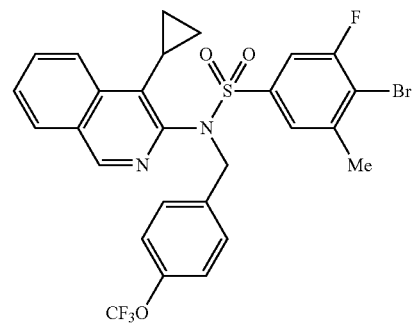

The compound obtained in (1) and 4-trifluoromethoxybenzyl bromide were treated in a similar manner to Reference Example 15-(2) to give 4-bromo-N-(4-cyclopropylisoquinolin-3-yl)-3-fluoro-5-methyl-N-[4-(trifluoromethoxy)benzyl]benzenesulfonamide APCI-MS m/z: 609/611 [M+H]$^+$.

(3) Synthesis of methyl 4-({(4-cyclopropylisoquino-lin-3-yl)[4-(trifluoromethoxy)benzyl]amino}sulfonyl)-2-fluoro-6-methylbenzoate

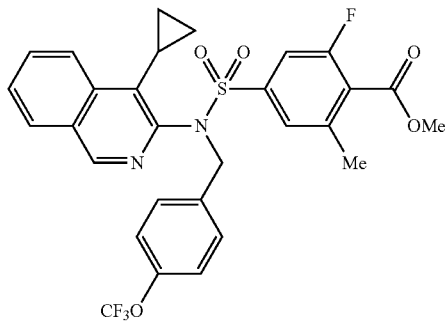

A mixture of the compound obtained in (2) (200 mg, 0.328 mmol), palladium acetate (9.0 mg, 0.040 mmol), 1,1'-bis(diphenylphosphino)ferrocene (38.8 mg, 0.0700 mmol), triethylamine (92 µL, 0.66 mmol), and methanol (534 µL, 13.2 mmol) in N,N-dimethylacetamide (1.7 mL) was stirred at 80° C. for 17 hours under carbon monoxide atmosphere. After cooled to room temperature, to the reaction mixture was added water, and the mixture was extracted twice with ethyl acetate. The organic layer was combined, washed with water and saturated saline, dried over anhydrous sodium sulfate, filtered, and concentrated under reduced pressure. The obtained residue was purified by a silica gel column chromatography (hexane:ethyl acetate=100:0→80:20) to give methyl 4-({(4-cyclopropylisoquinolin-3-yl)[4-(trifluoromethoxy)benzyl]amino}sulfonyl)-2-fluoro-6-methylbenzoate (49.0 mg, 20%) as a colorless viscous material.

APCI-MS m/z: 589 [M+H]⁺.

Reference Example 19

Preparation of methyl 4-({(4-cyclopropylisoquino-lin-3-yl)[4-(trifluoromethoxy)benzyl]amino}sulfonyl)-2-(methoxymethyl)benzoate

(1) Synthesis of ethyl 2-bromo-5-(chlorosulfonyl)benzoate

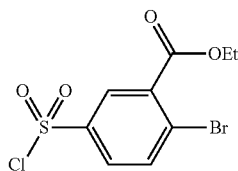 [SMILES: CCOC(=O)c1cc(S(=O)(=O)Cl)ccc1Br]

A mixture of 4-bromo-3-carboxybenzenesulfonyl chloride (1.0 g, 3.34 mmol) and thionyl chloride (10 mL) was stirred under reflux for 3 hours. The reaction mixture was concentrated under reduced pressure, ethanol (5 mL) was added thereto under ice-cooling, the mixture was stirred at room temperature for 20 minutes, and concentrated under reduced pressure. The residue was purified by a silica gel column chromatography (hexane:ethyl acetate=100:0→90: 10) to give ethyl 2-bromo-5-(chlorosulfonyl)benzoate (871 mg, 80%) as a colorless liquid.

1H-NMR (DMSO-d6) δ 1.33 (3H, t, J=7.2 Hz), 4.34 (2H, q, J=7.0 Hz), 7.64 (1H, dd, J=2.4 Hz, 8.5 Hz), 7.72 (1H, d, J=8.5 Hz), 7.93 (1H, d, J=2.1 Hz).

(2) Synthesis of ethyl 2-bromo-5-{[(4-cyclopropylisoquinolin-3-yl)amino]sulfonyl}benzoate

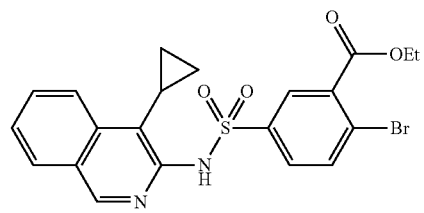 [SMILES: CCOC(=O)c1cc(S(=O)(=O)Nc2ncc3ccccc3c2C2CC2)ccc1Br]

To a solution of the compound obtained in (1) (711 mg, 2.17 mmol) in pyridine (10 mL) was added 3-amino-4-cyclopropylisoquinoline (400 mg, 2.17 mmol) under ice-cooling. The reaction temperature was gradually elevated, and the reaction mixture was stirred at room temperature overnight. To the reaction mixture was added ethyl acetate, the mixture was poured into 10% aqueous citric acid solution, and extracted with ethyl acetate. The organic layer was washed with 10% aqueous citric acid solution and saturated saline, dried over magnesium sulfate, filtered, and the filtrate was concentrated under reduced pressure. The obtained red oil was purified by a silica gel column chromatography (hexane:ethyl acetate=95:5→75:25) to give ethyl 2-bromo-5-{[(4-cyclopropylisoquinolin-3-yl)amino]sulfonyl}benzoate (890 mg, 86%) as a yellow solid.

APCI-MS m/z: 475/477 [M+H]⁺.

(3) Synthesis of ethyl 2-bromo-5-({(4-cyclopropylisoquinolin-3-yl)[4-(trifluoromethoxy)benzyl]amino}sulfonyl)benzoate

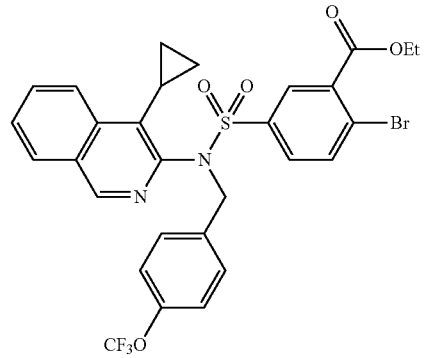

To a solution of the compound obtained in (2) (773 mg, 1.63 mmol) in N,N-dimethylformamide (10 mL) were added potassium carbonate (270 mg, 1.95 mmol) and 4-trifluoromethoxybenzyl bromide (435 mg, 1.71 mmol) under ice-cooling. The reaction temperature was gradually elevated, and the reaction mixture was stirred at room temperature overnight. To the reaction mixture was added ethyl acetate, the mixture was poured into saturated saline, and extracted with ethyl acetate. The organic layer was dried over magnesium sulfate, filtered, and the filtrate was concentrated under reduced pressure. The obtained yellow oil was purified by a silica gel column chromatography (hexane:ethyl acetate=100:0→84:16) to give ethyl 2-bromo-5-({(4-cyclopropylisoquinolin-3-yl)[4-(trifluoromethoxy)benzyl]amino}sulfonyl)benzoate (976 mg, 92%) as a white solid.

APCI-MS m/z: 649/651 [M+H]$^+$.

(4) Synthesis of 4-bromo-N-(4-cyclopropylisoquinolin-3-yl)-3-(hydroxymethyl)-N-[4-(trifluoromethoxy)benzyl]benzenesulfonamide

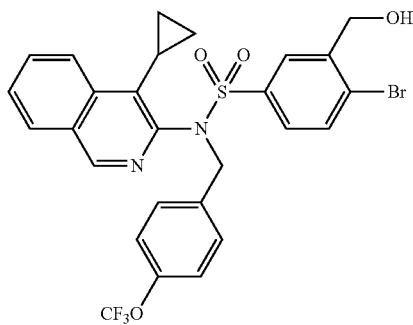

To a solution of the compound obtained in (3) (168 mg, 0.258 mmol) in tetrahydrofuran (5 mL) was added dropwise diisobutylaluminum hydride (1 mol/L solution in methylene chloride, 1.0 mL, 1.0 mmol) at −70° C. The reaction mixture was stirred at −70° C. for 3 hours, and additional diisobutylaluminum hydride (1 mol/L solution in methylene chloride, 1.3 mL, 1.3 mmol) was added dropwise thereto at the same temperature. The reaction mixture was stirred at −70° C. for 1 hour, then the reaction temperature was gradually elevated, and the mixture was stirred at room temperature overnight. The reaction mixture was cooled to −70° C. again, diisobutylaluminum hydride (1 mol/L solution in methylene chloride, 3.0 mL, 3.0 mmol) was added dropwise thereto at the same temperature, and the mixture was stirred overnight. Methanol was added thereto at −70° C., the mixture was warmed to room temperature, ethyl acetate was added thereto, and the mixture was poured into an aqueous potassium sodium tartrate solution. The mixture was stirred at room temperature for 8 hours, then extracted with ethyl acetate, the organic layer was washed with saturated saline, dried over magnesium sulfate, filtered, and the filtrate was concentrated under reduced pressure. The obtained yellow oil was purified by a silica gel column chromatography (hexane:ethyl acetate=100:0→75:25) to give 4-bromo-N-(4-cyclopropylisoquinolin-3-yl)-3-(hydroxymethyl)-N-[4-(trifluoromethoxy)benzyl]benzenesulfonamide (127 mg, 81%) as a white solid.

APCI-MS m/z: 607/609 [M+H]$^+$.

(5) Synthesis of 4-bromo-N-(4-cyclopropylisoquinolin-3-yl)-3-(methoxymethyl)-N-[4-(trifluoromethoxy)benzyl]benzenesulfonamide

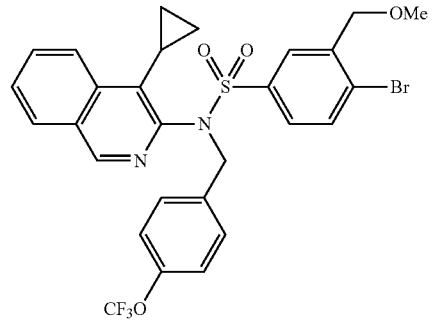

To a solution of the compound obtained in (4) (120 mg, 0.198 mmol) in N,N-dimethylformamide (3 mL) was added sodium hydride (60% oil dispersion, 9.5 mg, 0.237 mmol) under ice-cooling, and the mixture was stirred for 20 minutes under ice-cooling. Methyl iodide (25 μL, 0.395 mmol) was added thereto, the reaction temperature was gradually elevated, and the reaction mixture was stirred at room temperature overnight. To the reaction mixture was added ethyl acetate, the mixture was poured into saturated saline, and extracted with ethyl acetate. The organic layer was dried over magnesium sulfate, filtered, and the filtrate was concentrated under reduced pressure. The obtained pale yellow oil was purified by a silica gel column chromatography (hexane:ethyl acetate=100:0→80:20) to give 4-bromo-N-(4-cyclopropylisoquinolin-3-yl)-3-(methoxymethyl)-N-[4-(trifluoromethoxy)benzyl]benzenesulfonamide (119 mg, 96%) as a colorless oil.

APCI-MS m/z: 620/622 [M+H]$^+$.

(6) Synthesis of methyl 4-({(4-cyclopropylisoquinolin-3-yl)[4-(trifluoromethoxy)benzyl]amino}sulfonyl)-2-(methoxymethyl)benzoate

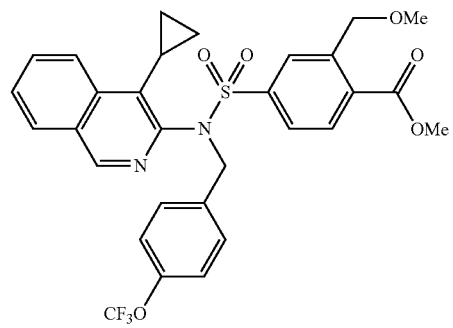

A mixture of the compound obtained in (5) (116 mg, 0.187 mmol), tri-t-butylphosphine tetrafluoroborate (11.9 mg, 0.041 mmol), trans-di(μ-acetato)bis[o-(di-o-tolylphosphino)benzyl]dipalladium(II) (19.3 mg, 0.021 mmol), molybdenum hexacarbonyl (49.8 mg, 0.19 mmol), and 1,8-diazabicyclo[5.4.0]undec-7-ene (28.2 μL, 0.19 mmol) in methanol (3 mL) and acetonitrile (1 mL) was stirred at 150° C. for 40 minutes under microwave irradiation. After cooling, the reaction mixture was filtered using diatomaceous earth, and the diatomaceous earth was washed with methanol. The filtrate was concentrated under reduced pressure, the obtained brown gumlike solid was dissolved in N,N-dimethylformamide (2 mL), potassium carbonate (13 mg, 0.09 mmol) and methyl iodide (5.8 μL, 0.1 mmol) were added thereto at room temperature, and the mixture was stirred at room temperature overnight. To the reaction mixture was added ethyl acetate, the mixture was poured into saturated saline, and extracted with ethyl acetate. The organic layer was dried over magnesium sulfate, filtered, and concentrated under reduced pressure. The obtained brown oil was purified by a silica gel column chromatography (hexane:ethyl acetate=75:25) to give methyl 4-({(4-cyclopropylisoquinolin-3-yl)[4-(trifluoromethoxy)benzyl]amino}sulfonyl)-2-(methoxymethyl)benzoate (44 mg, 39%) as a colorless oil.

APCI-MS m/z: 601 [M+H]$^+$.

Reference Example 20

Preparation of methyl 2-cyclopropyl-4-({(4-cyclopropylisoquinolin-3-yl)[4-(trifluoromethoxy)benzyl]amino}sulfonyl)benzoate (1) Synthesis of methyl 2-bromo-4-{[(4-cyclopropylisoquinolin-3-yl)amino]sulfonyl}benzoate

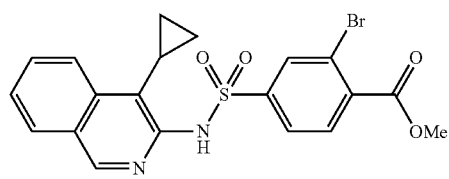

4-Cyclopropylisoquinoline-3-amine and 3-bromo-4-methoxycarbonylbenzenesulfonyl chloride were treated in a similar manner to Reference Example 15-(1) to give methyl 2-bromo-4-{[(4-cyclopropylisoquinolin-3-yl)amino]sulfonyl}benzoate.

APCI-MS m/z: 461/463 [M+H]$^+$.

(2) Synthesis of methyl 2-bromo-4-({(4-cyclopropylisoquinolin-3-yl)[4-(trifluoromethoxy)benzyl]amino}sulfonyl)benzoate

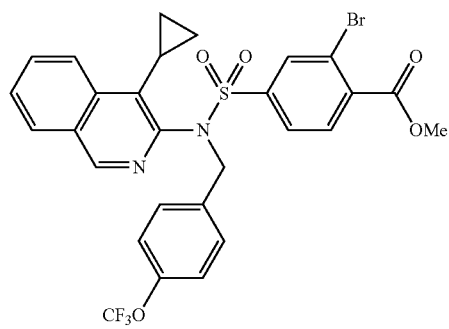

The compound obtained in (1) and 4-trifluoromethoxybenzyl bromide were treated in a similar manner to Reference Example 15-(2) to give methyl 2-bromo-4-({(4-cyclopropylisoquinolin-3-yl)[4-(trifluoromethoxy)benzyl]amino}sulfonyl)benzoate.

APCI-MS m/z: 635/637 [M+H]$^+$.

(3) Synthesis of methyl 2-cyclopropyl-4-({(4-cyclopropylisoquinolin-3-yl)[4-(trifluoromethoxy)benzyl]amino}sulfonyl)benzoate

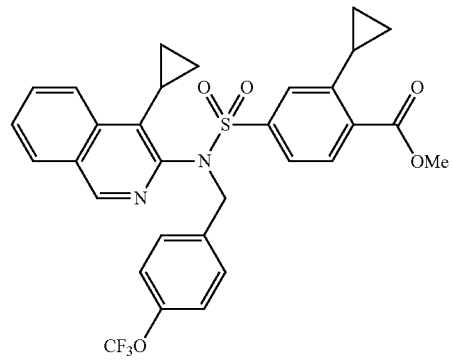

A mixture of the compound obtained in (2) (71.0 mg, 0.112 mmol), cyclopropylboronic acid (28.8 mg, 0.335 mmol), tricyclohexylphosphine (6.3 mg, 0.022 mmol), tripotassium phosphate (83.0 mg, 0.391 mmol), and palladium acetate (2.5 mg, 0.011 mmol) in toluene (1.4 mL) and water (0.1 mL) was stirred at 100° C. for 3 hours under argon atmosphere. After cooled to room temperature, to the reaction mixture was added water, and the mixture was extracted three times with ethyl acetate. The organic layer was combined and dried, and concentrated under reduced pressure. The obtained residue was purified by a silica gel column chromatography (hexane:ethyl acetate=100:0→80:20) to give methyl 2-cyclopropyl-4-({(4-cyclopropylisoquinolin-3-yl)[4-(trifluoromethoxy)benzyl]amino}sulfonyl)benzoate (53.0 mg, 79%) as a white viscous material.

APCI-MS m/z: 597 [M+H]$^+$.

Reference Example 21

Preparation of methyl 4-({(4-cyclopropylisoquinolin-3-yl)[4-(trifluoromethoxy)benzyl]amino}sulfonyl)-2-isopropylbenzoate (1) Synthesis of methyl 4-({(4-cyclopropylisoquinolin-3-yl)[4-(trifluoromethoxy)benzyl]amino}sulfonyl)-2-isopropenylbenzoate

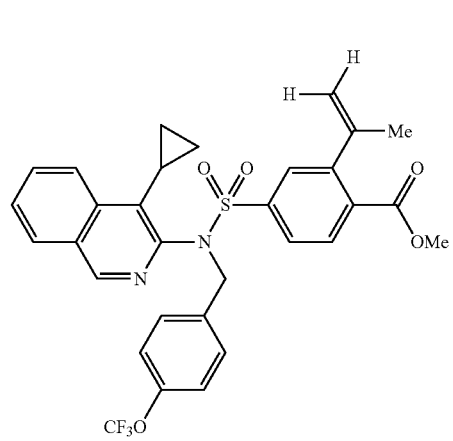

Methyl 2-bromo-4-({(4-cyclopropylisoquinolin-3-yl)[4-(trifluoromethoxy)benzyl]amino}sulfonyl)benzoate obtained in Reference Example 20-(2) and isopropenylboronic acid pinacol ester were treated in a similar manner to Reference Example 20-(3) to give methyl 4-({(4-cyclopropylisoquinolin-3-yl)[4-(trifluoromethoxy)benzyl]amino}sulfonyl)-2-isopropenylbenzoate.

APCI-MS m/z: 597 [M+H]$^+$.

(2) Synthesis of methyl 4-({(4-cyclopropylisoquinolin-3-yl)[4-(trifluoromethoxy)benzyl]amino}sulfonyl)-2-isopropylbenzoate

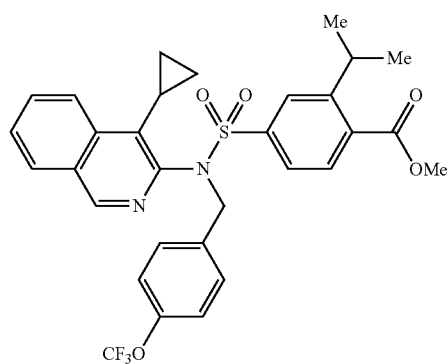

A mixture of the compound obtained in (1) (57.0 mg, 0.096 mmol) and 5% palladium carbon (17.0 mg) in methanol (1.1 mL) was stirred at room temperature for 7 hours under hydrogen gas atmosphere (0.1 MPa). The reaction mixture was filtered, and the filtrate was concentrated under reduced pressure. The obtained residue was purified by a silica gel column chromatography (hexane:ethyl acetate=100:0→80:20) to give methyl 4-({(4-cyclopropylisoquinolin-3-yl)[4-(trifluoromethoxy)benzyl]amino}sulfonyl)-2-isopropylbenzoate (49.0 mg, 86%) as a white viscous material.

APCI-MS m/z: 599 [M+H]$^+$.

Reference Example 22

Preparation of methyl 4-({(1-cyclopropyl-4-methylisoquinolin-3-yl)[4-(trifluoromethoxy)benzyl]amino}sulfonyl)-2-methylbenzoate (1) Synthesis of methyl 4-{[(1-bromo-4-methylisoquinolin-3-yl)amino]sulfonyl}-2-methylbenzoate

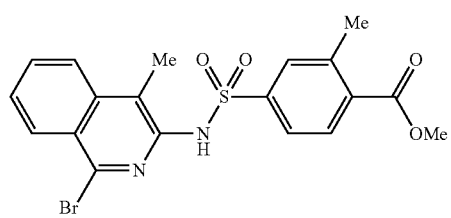 [SMILES: COC(=O)c1ccc(S(=O)(=O)Nc2nc(Br)c3ccccc3c2C)cc1C]

1-Bromo-4-methylisoquinoline-3-amine (300 mg, 1.27 mmol) and 4-methoxycarbonyl-3-methylbenzenesulfonyl chloride were treated in a similar manner to Reference Example 15-(1) to give methyl 4-{[(1-bromo-4-methylisoquinolin-3-yl)amino]sulfonyl}-2-methylbenzoate (460 mg, 81%) as a pale brown solid.

APCI-MS m/z: 449/451 [M+H]$^+$.

(2) Synthesis of methyl 4-({(1-bromo-4-methylisoquinolin-3-yl)[4-(trifluoromethoxy)benzyl]amino}sulfonyl)-2-methylbenzoate

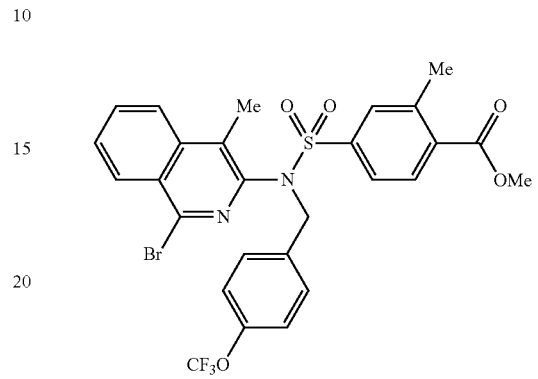

The compound obtained in (1) (455 mg, 1.01 mmol) and 4-trifluoromethoxybenzyl bromide were treated in a similar manner to Reference Example 15-(2) to give methyl 4-({(1-bromo-4-methylisoquinolin-3-yl)[4-(trifluoromethoxy)benzyl]amino}sulfonyl)-2-methylbenzoate (580 mg, 92%) as a colorless viscous material.

APCI-MS m/z: 623/625 [M+H]$^+$.

(3) Synthesis of methyl 4-({(1-cyclopropyl-4-methylisoquinolin-3-yl)[4-(trifluoromethoxy)benzyl]amino}sulfonyl)-2-methylbenzoate

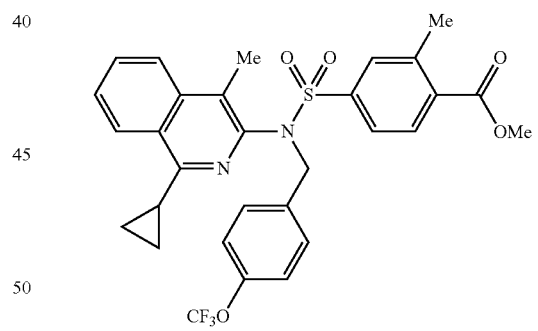

A mixture of the compound obtained in (2) (575 mg, 0.922 mmol), cyclopropyltrifluoroborate potassium salt (273 mg, 1.84 mmol), palladium acetate (21 mg, 0.0922 mmol), di(1-adamantyl)butylphosphine (50 mg, 0.138 mmol), and cesium carbonate (600 mg, 1.84 mmol) in water (500 µL) and toluene (5 mL) was heated under reflux for 3 hours under argon atmosphere. After cooled to room temperature, to the reaction mixture were added ethyl acetate and water, and the mixture was extracted with ethyl acetate. The organic layer was washed with saturated saline, dried over sodium sulfate, filtered, and the filtrate was concentrated under reduced pressure. The obtained residue was purified by a silica gel column chromatography (hexane:ethyl acetate=90:10→80:20) to give methyl 4-({(1-cyclopropyl- 4-methylisoquinolin-3-yl)[4-(trifluoromethoxy)benzyl]amino}sulfonyl)-2-methylbenzoate (525 mg, 97%) as a pale yellow viscous material.

APCI-MS m/z: 585 [M+H]+.

Reference Example 23

Preparation of methyl 4-({(4-cyclopropylisoquinolin-3-yl)[4-(trifluoromethoxy)benzyl]amino}sulfonyl)-2-(dimethylamino)benzoate

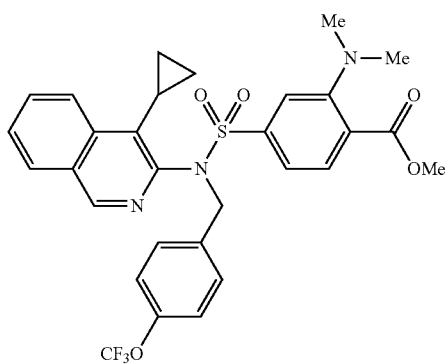

A solution of methyl 4-({(4-cyclopropylisoquinolin-3-yl)[4-(trifluoromethoxy)benzyl]amino}sulfonyl)-2-fluorobenzoate obtained in Reference Example 7 (30.0 mg, 0.052 mmol) and dimethylamine (2 mol/L solution in tetrahydrofuran, 131 μL, 0.261 mmol) in N,N-dimethylformamide (1.2 mL) was stirred at 150° C. overnight. After cooled to room temperature, to the reaction mixture was added water, and the mixture was extracted three times with ethyl acetate. The organic layer was combined, washed twice with water, dried, and concentrated under reduced pressure. The obtained residue was purified by a silica gel column chromatography (hexane:ethyl acetate=100:0→70:30) to give methyl 4-({(4-cyclopropylisoquinolin-3-yl)[4-(trifluoromethoxy)benzyl]amino}sulfonyl)-2-(dimethylamino)benzoate (15.1 mg, 48%) as a pale yellow solid.

APCI-MS m/z: 600 [M+H]+.

Reference Example 24

Preparation of methyl 2-amino-4-({(4-cyclopropylisoquinolin-3-yl)[4-(trifluoromethoxy)benzyl]amino}sulfonyl)benzoate

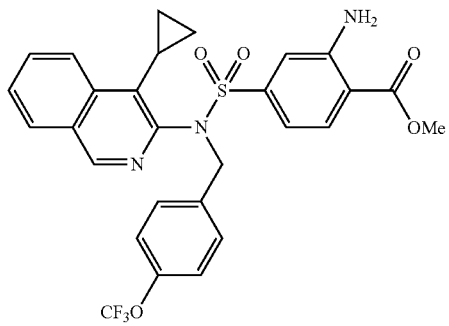

A mixture of methyl 2-bromo-4-({(4-cyclopropylisoquinolin-3-yl)[4-(trifluoromethoxy)benzyl]amino}sulfonyl)benzoate obtained in Reference Example 20-(2) (60.0 mg, 0.094 mmol), copper (12.0 mg, 0.188 mmol), trimethylsilyl azide (25.1 μL, 0.188 mmol), and 2-aminoethanol (14.3 μL, 0.236 mmol) in N,N-dimethylacetamide (1.2 mL) was stirred at 95° C. overnight under argon atmosphere. After cooled to room temperature, to the reaction mixture was added an aqueous saturated sodium hydrogen carbonate solution, and the mixture was extracted three times with ethyl acetate. The organic layer was combined, washed twice with water, dried, and the filtrate was concentrated under reduced pressure. The obtained residue was purified by a silica gel column chromatography (hexane:ethyl acetate=100:0→70:30) to give methyl 2-amino-4-({(4-cyclopropylisoquinolin-3-yl)[4-(trifluoromethoxy)benzyl]amino}sulfonyl)benzoate (23.0 mg, 43%) as a pale yellow solid.

APCI-MS m/z: 572 [M+H]+.

Reference Example 25

Preparation of methyl 2-bromo-4-(chlorosulfonyl)benzoate

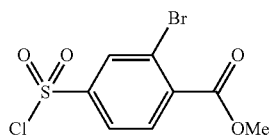

(1-A)

To a solution of copper(I) chloride (76.8 mg, 0.737 mmol) in water (25 mL) was added dropwise thionyl chloride (4.2 mL) under ice-cooling, then the reaction temperature was gradually elevated, and the mixture was stirred at room temperature overnight.

(1-B)

To a solution of 4-amino-2-bromobenzoic acid methyl ester (1700 mg, 7.368 mmol) in concentrated hydrochloric acid (27 mL) and water (102 mL) was added dropwise a solution of sodium nitrite (567 mg, 8.104 mmol) in water (25 mL) at −5° C., and the mixture was stirred at −5° C. for 30 minutes. To the reaction mixture was added dropwise a solution prepared in (1-A) at −5° C., the reaction temperature was gradually elevated, and the mixture was stirred at room temperature for 2 hours. The obtained viscous material was collected by filtration, the obtained viscous material was dissolved in chloroform, dried, and concentrated under reduced pressure. The obtained residue was purified by a silica gel column chromatography (hexane:ethyl acetate=100:0→60:40) to give methyl 2-bromo-4-(chlorosulfonyl)benzoate (997 mg, 43%) as an orange solid.

$^1$H-NMR (DMSO-$d_6$) δ 3.86 (3H, s), 7.66 (1H, dd, J=1.5 Hz, 7.9 Hz), 7.76 (1H, d, J=7.9 Hz), 7.84 (1H, d, J=1.5 Hz).

Reference Example 26

Preparation of methyl 4-(chlorosulfonyl)-2-methoxybenzoate

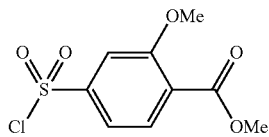 [SMILES: COC(=O)c1ccc(S(=O)(=O)Cl)cc1OC]

4-Amino-2-methoxybenzoic acid methyl ester was treated in a similar manner to Reference Example 25 to give methyl 4-(chlorosulfonyl)-2-methoxybenzoate.

$^1$H-NMR (DMSO-$d_6$) δ 3.78 (3H, s), 3.82 (3H, s), 7.23 (1H, dd, J=1.2 Hz, 7.9 Hz), 7.30 (1H, d, J=1.2 Hz), 7.62 (1H, d, J=7.9 Hz).

Reference Example 27

Preparation of 4-bromo-3-fluoro-5-methylbenzenesulfonyl chloride

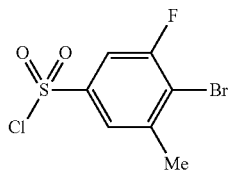 [SMILES: Cc1cc(S(=O)(=O)Cl)cc(F)c1Br]

4-Bromo-3-fluoro-5-methylaniline was treated in a similar manner to Reference Example 25 to give 4-bromo-3-fluoro-5-methylbenzenesulfonyl chloride.

$^1$H-NMR (CDCl$_3$, 400 MHz) δ 7.73 (d, J=2.1 Hz, 1H), 7.63 (dd, J=6.7, 2.1 Hz, 1H), 2.57 (s, 3H).

Reference Example 28

Preparation of 4-bromo-N-(4-cyclopropylisoquinolin-3-yl)-3,5-dimethylbenzenesulfonamide (1) Synthesis of 4-bromo-3,5-dimethylbenzenesulfonyl chloride (1-A)

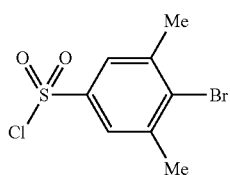

To a solution of copper(I) chloride (26.0 g, 0.250 mmol) in water (7.5 mL) was added dropwise thionyl chloride (1.3 mL) under ice-cooling, then the reaction temperature was gradually elevated, and the mixture was stirred at room temperature overnight.

(1-B)

To a mixture of 3,5-dimethyl-4-bromoaniline (500 mg, 2.499 mmol) in concentrated hydrochloric acid (2.5 mL) and water (0.5 mL) was added dropwise a solution of sodium nitrite (193 mg, 2.749 mmol) in water (1.3 mL) at −5° C. After stirred at −5° C. for 30 minutes, to the mixture was added dropwise a solution prepared in (1-A) at the same temperature. The reaction temperature was gradually elevated, and the reaction mixture was stirred at room temperature overnight. The reaction mixture was extracted three times with chloroform, the organic layer was combined, dried, and concentrated under reduced pressure to give a crude product of 4-bromo-3,5-dimethylbenzenesulfonyl chloride (375 mg). The resultant was used in the next step without further purification.

(2) Synthesis of 4-bromo-N-(4-cyclopropylisoquinolin-3-yl)-3,5-dimethylbenzenesulfonamide

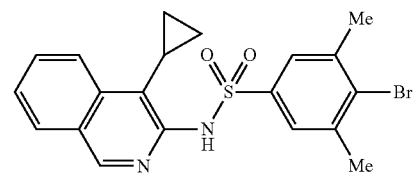

To a solution of 3-amino-4-cyclopropylisoquinoline (100 mg, 0.543 mmol) in pyridine (2.7 mL) was added the crude product obtained in (1-B) (154 mg) at room temperature, and the mixture was stirred at room temperature for 1 hour. To the reaction mixture was added additional crude product obtained in (1-B) (215 mg), and the mixture was stirred at room temperature overnight. The reaction mixture was concentrated under reduced pressure, and toluene was added thereto to carry out azeotropy. The obtained residue was purified by a silica gel column chromatography (hexane:ethyl acetate=100:0→70:30) to give 4-bromo-N-(4-cyclopropylisoquinolin-3-yl)-3,5-dimethylbenzenesulfonamide (61.0 mg, yield for two steps: 6%) as a yellow viscous material.

APCI-MS m/z: 431/433 [M+H]$^+$.

Reference Examples 29 to 32

The corresponding starting compounds were treated in a similar manner to Reference Example 15 to give the following compounds of Table 12.

TABLE 12

| Reference Example | Structure | Physical data |
|---|---|---|
| 29 | 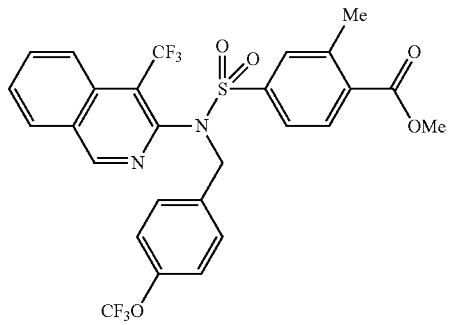 | APCI-MS m/z: 599 [M + H]$^+$ |
| 30 | 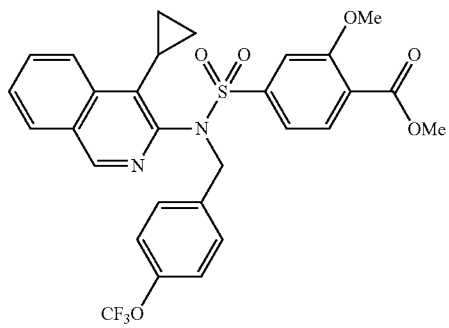 | APCI-MS m/z: 587 [M + H]$^+$ |
| 31 | 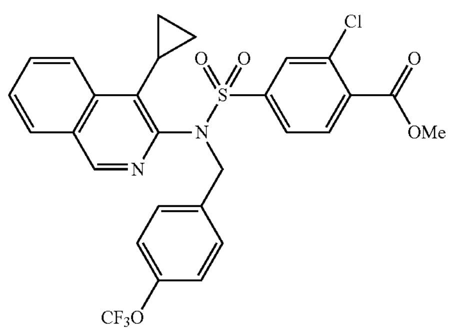 | APCI-MS m/z: 591/593 [M + H]$^+$ |
| 32 | 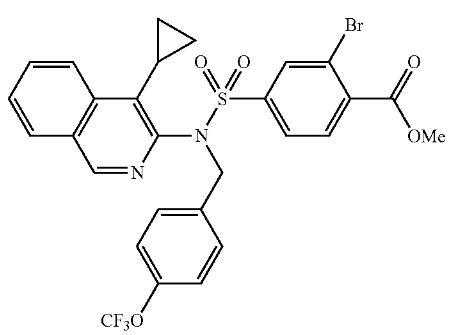 | APCI-MS m/z: 635/637 [M + H]$^+$ |

Reference Examples 33 to 35

The corresponding starting compounds were treated in a similar manner to Reference Example 17 and/or 18 to give the following compounds of Table 13.

TABLE 13

| Reference Example | Structure | Physical data |
|---|---|---|
| 33 | (4-cyclopropylisoquinolin-3-yl)-N-(4-methoxybenzyl)-sulfonamide with 4-(methoxycarbonyl)-3-(trifluoromethyl)phenyl and 4-(trifluoromethoxy)benzyl groups | APCI-MS m/z: 625 [M + H]+ |
| 34 | Analogous structure with 2,6-dimethyl-4-(methoxycarbonyl)phenyl sulfonyl group | APCI-MS m/z: 585 [M + H]+ |
| 35 | Analogous structure with 3-fluoro-4-(ethoxycarbonyl)phenyl sulfonyl group | APCI-MS m/z: 589 [M + H]+ |

Reference Examples 36 to 38

The corresponding starting compounds were treated in a similar manner to Reference Example 20 to give the following compounds of Table 14.

TABLE 14

| Reference Example | Structure | Physical data |
|---|---|---|
| 36 | 4-(trifluoromethyl)isoquinolin-3-yl sulfonamide with 2-ethyl-4-(methoxycarbonyl)phenyl and 4-(trifluoromethoxy)benzyl groups | APCI-MS m/z: 613 [M + H]+ |

TABLE 14-continued
| Reference Example | Structure | Physical data |
|---|---|---|
| 37 | 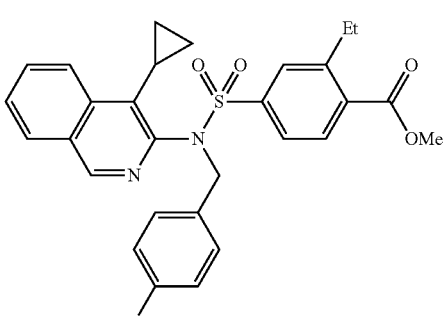 | APCI-MS m/z: 585 [M + H]+ |
| 38 | 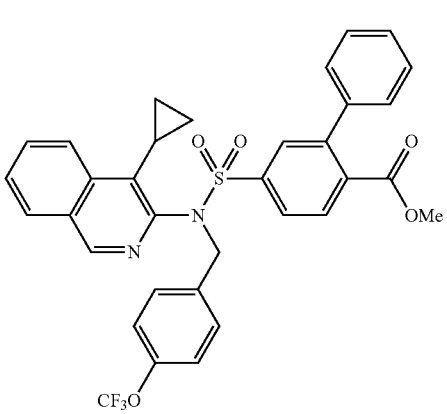 | APCI-MS m/z: 633 [M + H]+ |
Reference Examples 39 and 40
The corresponding starting compounds were treated in a similar manner to Reference Example 23 to give the following compounds of Table 15.
TABLE 15
| Reference Example | Structure | Physical data |
|---|---|---|
| 39 | 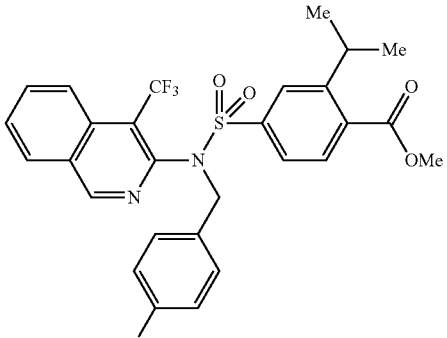 | APCI-MS m/z: 626 [M + H]+ |

TABLE 15-continued

| Reference Example | Structure | Physical data |
|---|---|---|
| 40 | (structure) | APCI-MS m/z: 599 [M + H]+ |

Reference Examples 41 to 43

The corresponding starting compounds were treated in a similar manner to Reference Example 23 to give the following compounds of Table 16.

TABLE 16

| Reference Example | Structure | Physical data |
|---|---|---|
| 41 | (structure) | APCI-MS m/z: 626 [M + H]+ |
| 42 | (structure) | APCI-MS m/z: 640 [M + H]+ |

TABLE 16-continued

| Reference Example | Structure | Physical data |
|---|---|---|
| 43 | [Structure diagram of a compound containing isoquinoline with cyclopropyl group, sulfonamide linker, benzyl group with 4-OCF₃ substituent, and phenyl ring with morpholine and methyl ester substituents] | APCI-MS m/z: 642 [M + H]$^+$ |

Pharmacological Experiment

1. TRPM8 Inhibition Assay

Test Compound:

The compounds of the above Examples were used in a TRPM8 inhibition assay.

Method:

The functional activity of a test compound was determined by measuring change in intracellular calcium concentration using a calcium sensitive fluorescent dye. The change in fluorescent signal was measured by the cell imaging technology by Hamamatsu Photonics's Functional Drug Screening System (FDSS). Increase in intracellular calcium concentration was readily detected upon activation with menthol.

HEK293 cells stably expressing human TRPM8 were grown in a flask. On assay day, the culture medium was removed from the flask, and cells were washed with phosphate-buffered saline (PBS) and harvested with PBS containing 2 mmol/L of ethylenediaminetetraacetic acid disodium salt (EDTA-2Na). The cells were then incubated with assay solution containing 3 µmol/L of Fura-2AM and 0.01% Pluronic F-127 for 60 minutes. Subsequently, suspended 20,000 to 50,000 cells per well were incubated with a test compound (at varying concentrations) in each well at 37° C. for 20 minutes. Change in intracellular calcium concentration evoked by 100 µmol/L of menthol was measured for 2 minutes using FDSS. The 50% inhibitory concentration (IC$_{50}$ value) was determined from four-point concentration-response studies. The concentration-response curve was generated using the average of quadruplicate wells for each data point.

Results:

The following Table 17 shows an IC$_{50}$ value of each test compound.

TABLE 17

| Test Compound (Example No.) | TRPM8 Blocking Test (IC$_{50}$/nmol/L) |
|---|---|
| 1 | 0.3 |
| 2 | 0.7 |
| 3 | 7.6 |
| 4 | 1.1 |
| 5 | 3.4 |
| 6 | 1.7 |
| 7 | 1.0 |
| 8 | 2.3 |
| 9 | 1.1 |
| 10 | 23.9 |
| 11 | 29.5 |
| 12 | 40.2 |
| 13 | 4.3 |
| 14 | 0.7 |
| 15 | 2.0 |
| 16 | 1.6 |
| 17 | 0.3 |
| 18 | 0.9 |
| 19 | 3.5 |
| 20 | 3.2 |
| 21 | 1.1 |
| 22 | 0.6 |
| 23 | 0.5 |
| 24 | 1.2 |
| 25 | 0.7 |
| 26 | 1.0 |
| 27 | 0.8 |
| 28 | 3.5 |
| 29 | 2.2 |
| 30 | 1.1 |
| 31 | 1.1 |
| 32 | 2.7 |
| 33 | 3.6 |
| 34 | 0.5 |
| 35 | 9.6 |
| 36 | 1.4 |
| 37 | 9.5 |
| 38 | 0.7 |
| 39 | 1.4 |
| 40 | 6.5 |
| 41 | 1.1 |
| 42 | 1.5 |
| 43 | 10.1 |
| 44 | 5.6 |
| 45 | 2.9 |
| 46 | 3.3 |
| 47 | 3.8 |
| 48 | 6.3 |
| 49 | 18.1 |
| 50 | 11.7 |
| 51 | 10.9 |
| 52 | 1.0 |
| 53 | 3.0 |
| 54 | 2.1 |
| 55 | 13.6 |
| 56 | 6.6 |

TABLE 17-continued

| Test Compound (Example No.) | TRPM8 Blocking Test (IC$_{50}$/nmol/L) |
|---|---|
| 57 | 2.5 |
| 58 | 4.6 |
| 59 | 10.3 |
| 60 | 19.6 |

2. In Vivo TRPM8 Antagonistic Assay in Rat

Test Compound:

The compounds of the above Examples were used in a TRPM8 antagonistic assay in rat.

Method:

The in vivo antagonistic activity of the test compound was assessed in the wet-dog shakes (WDS) model in rat. A rat exhibits shaking behavior in response to menthol, a TRPM8 agonist. Pretreatment of a rat with a TRPM8 antagonist prior to menthol administration inhibits the observed shaking behavior.

To assess the activity of a TRPM8 antagonist to inhibit menthol-induced shaking behavior in a Sprague Dawley (SD) male rat, each test compound (3 mg/kg, oral administration, a solution in 0.5% methylcellulose; N=3-4/group) was administered 1, 2, or 4 hours prior to menthol challenge (50 mg/kg, intraperitoneal administration, in 10% Macrogol 15 Hydroxystearate/physiological saline solution). Spontaneous WDS were counted for 5 minutes post menthol dosing. Inhibition of the spontaneous WDS behavior relative to vehicle pretreatment is expressed as percent (%) inhibition, calculated as follows:

% Inhibition=[1−(WDS count in the group treated with a test compound/WDS count in the group treated with vehicle)]×100.

INDUSTRIAL APPLICABILITY

The compound of the formula (I) of the present invention is useful for the prevention and treatment of various diseases involving TRPM8 (e.g., a chronic pain such as neuropathic pain (preferably, neuropathic pain caused by cold allodynia or diabetic neuropathy)).

The invention claimed is:

1. A compound of the formula (I):

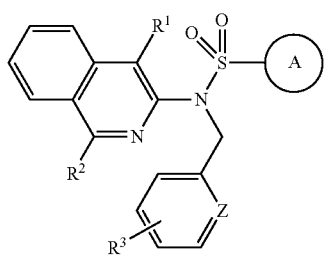

wherein $R^1$ is optionally substituted alkyl or optionally substituted cycloalkyl,
$R^2$ is a hydrogen atom or optionally substituted cycloalkyl,
$R^3$ is optionally substituted alkyl or optionally substituted alkoxy,
Z is CH or N,
Ring A is the following formula (i), (ii), or (ix):

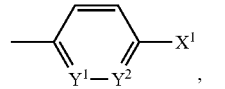

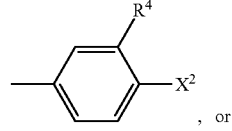

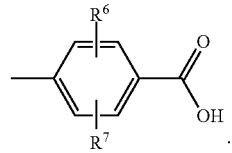

$R^4$ is optionally substituted alkyl,
$R^6$ is optionally substituted alkyl, optionally substituted cycloalkyl, optionally substituted alkoxy, optionally substituted alkylamino, optionally substituted dialkylamino, an optionally substituted monocyclic nitrogen-containing non-aromatic heterocyclic group, optionally substituted phenyl, or halogen,
$R^7$ is a hydrogen atom, optionally substituted alkyl, or halogen,
$X^1$ and $X^2$ are each independently tetrazolyl, tetrazolinonyl, optionally substituted triazolyl, triazolinonyl, oxadiazolonyl, optionally substituted alkanoylaminomethyl, or optionally substituted alkylsulfonylaminomethyl, or
$R^4$ and $X^2$ combine with each other at their terminals together with the adjacent benzene to form indazolinonyl or benzoisoxazolonyl, and
$Y^1$ and $Y^2$ are both CH, or one of $Y^1$ and $Y^2$ is CH, and the other is N, or a pharmaceutically acceptable salt thereof.

2. The compound according to claim 1, wherein
$R^1$ is $C_1$-$C_6$ alkyl, $C_1$-$C_6$ halogenoalkyl, or $C_3$-$C_7$ cycloalkyl, and
$R^2$ is a hydrogen atom or $C_3$-$C_7$ cycloalkyl,
or a pharmaceutically acceptable salt thereof.

3. The compound according to claim 1, wherein $R^3$ is $C_1$-$C_6$ halogenoalkyl or $C_1$-$C_6$ halogenoalkoxy, or a pharmaceutically acceptable salt thereof.

4. The compound according to claim 1, wherein
$R^1$ is $C_1$-$C_6$ alkyl, $C_1$-$C_6$ halogenoalkyl, or $C_3$-$C_7$ cycloalkyl,
$R^2$ is a hydrogen atom or $C_3$-$C_7$ cycloalkyl, and
$R^3$ is $C_1$-$C_6$ halogenoalkyl or $C_1$-$C_6$ halogenoalkoxy,
or a pharmaceutically acceptable salt thereof.

5. The compound according to any one of claims 1-4, wherein
Ring A is the formula (i) or formula (ii),
$R^4$ is $C_1$-$C_6$ alkyl, and
$X^1$ and $X^2$ are each independently tetrazolyl, tetrazolinonyl, triazolyl, $C_1$-$C_6$ alkyltriazolyl, $C_1$-$C_6$ halogenoalkyltriazolyl, triazolinonyl, oxadiazolonyl, $C_2$-$C_7$ alkanoylaminomethyl, $C_1$-$C_6$ alkylsulfonylaminomethyl, or $C_1$-$C_6$ halogenoalkylsulfonylaminomethyl, or
$R^4$ and $X^2$ combine with each other at their terminals together with the adjacent benzene to form indazolinonyl or benzoisoxazolonyl,
or a pharmaceutically acceptable salt thereof.

6. The compound according to any one of claims 1-4, wherein
  Ring A is the formula (i) or formula (ii),
  $R^4$ is $C_1$-$C_6$ alkyl, and
  $X^1$ and $X^2$ are each independently tetrazolyl, tetrazolinonyl, triazolyl, $C_1$-$C_6$ alkyltriazolyl, $C_1$-$C_6$ halogenoalkyltriazolyl, triazolinonyl, or oxadiazolonyl,
  $R^4$ and $X^2$ combine with each other at their terminals together with the adjacent benzene to form indazolinonyl or benzoisoxazolonyl,
or a pharmaceutically acceptable salt thereof.

7. The compound according to claim 1, wherein
  $R^1$ is $C_1$-$C_6$ alkyl, $C_1$-$C_6$ halogenoalkyl, or $C_3$-$C_7$ cycloalkyl,
  $R^2$ is a hydrogen atom or $C_3$-$C_7$ cycloalkyl,
  $R^3$ is $C_1$-$C_6$ halogenoalkyl or $C_1$-$C_6$ halogenoalkoxy,
  Ring A is the formula (i) or (ii),
  $R^4$ is $C_1$-$C_6$ alkyl, and
  $X^1$ and $X^2$ are each independently tetrazolyl, tetrazolinonyl, triazolyl, alkyltriazolyl, $C_1$-$C_6$ halogenoalkyltriazolyl, triazolinonyl, oxadiazolonyl, $C_2$-$C_7$ alkanoylaminomethyl, $C_1$-$C_6$ alkylsulfonylaminomethyl, or $C_1$-$C_6$ halogenoalkylsulfonylaminomethyl, or
  $R^4$ and $X^2$ combine with each other at their terminals together with the adjacent benzene to form indazolinonyl or benzoisoxazolonyl,
or a pharmaceutically acceptable salt thereof.

8. The compound according to any one of claims 1-4, wherein
  Ring A is the formula (i) or formula (ii),
  $R^4$ is $C_1$-$C_6$ alkyl, and
  $X^1$ and $X^2$ are each independently the following formula (iii), (iv), (v), (vi), or (vii):

(iii)

(iv)

(v)

(vi)

(vii)

wherein $R^5$ is a hydrogen atom, $C_1$-$C_6$ alkyl, or $C_1$-$C_6$ halogenoalkyl, and $V^1$ is NH or O, or
  $R^4$ and $X^2$ combine with each other at their terminals together with the adjacent benzene to form the following formula (viii):

(viii)

wherein $V^2$ is NH or O,
or a pharmaceutically acceptable salt thereof.

9. The compound according to any one of claims 1-4, wherein
  Ring A is the formula (i) or formula (ii),
  $R^4$ is $C_1$-$C_6$ alkyl,
  $X^1$ and $X^2$ are each independently the following formula (iii), (iv), (v-a), or (vii-a):

(iii)

(iv)

(v-a)

(vii-a)

wherein $R^{5a}$ is a hydrogen atom or $C_1$-$C_6$ alkyl, or
  $R^4$ and $X^2$ combine with each other at their terminals together with the adjacent benzene to form the following formula (vii-a):

(viii-a)

$Y^1$ is CH, and
  $Y^2$ is CH or N,
or a pharmaceutically acceptable salt thereof.

10. The compound according to claim 1, wherein
  $R^1$ is cyclopropyl,
  $R^2$ is a hydrogen atom,
  $R^3$ is $C_1$-$C_6$ fluoroalkyl or $C_1$-$C_6$ fluoroalkoxy, and
  Ring A is the formula (i) or formula (ii),
or a pharmaceutically acceptable salt thereof.

11. The compound according to claim 1, wherein
  $R^1$ is trifluoromethyl,
  $R^2$ is a hydrogen atom,
  $R^3$ is $C_1$-$C_6$ fluoroalkoxy,
  Z is CH, and Ring A is the formula (i) or formula (ii),
or a pharmaceutically acceptable salt thereof.

12. The compound according to claim 1, wherein
$R^1$ is methyl,
$R^2$ is cyclopropyl,
$R^3$ is $C_1$-$C_6$ fluoroalkoxy,
Z is CH, and
Ring A is the formula (i) or formula (ii),
or a pharmaceutically acceptable salt thereof.

13. The compound according to claim 1, wherein
$R^1$ is $C_1$-$C_6$ alkyl, $C_1$-$C_6$ halogenoalkyl, or $C_3$-$C_7$ cycloalkyl,
$R^2$ is a hydrogen atom or $C_3$-$C_7$ cycloalkyl,
$R^3$ is $C_1$-$C_6$ halogenoalkyl or $C_1$-$C_6$ halogenoalkoxy,
Z is CH or N,
Ring A is the formula (i) or (ii),
$R^4$ is $C_1$-$C_6$ alkyl,
$X^1$ and $X^2$ are each independently the following formula (iii), (iv), (v-a), or (vii-a)

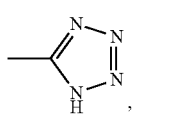
(iii)

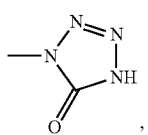
(iv)

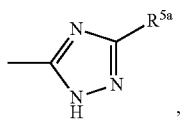
(v-a)

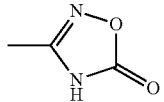
(vii-a)

wherein $R^{5a}$ is a hydrogen atom or $C_1$-$C_6$ alkyl, or
$R^4$ and $X^2$ combine with each other at their terminals together with the adjacent benzene to form the following formula (viii-a):

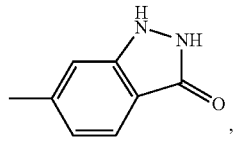
(viii-a)

$Y^1$ is CH, and
$Y^2$ is CH or N,
or a pharmaceutically acceptable salt thereof.

14. The compound according to claim 13 wherein
$R^1$ is $C_1$-$C_6$ halogenoalkyl or $C_3$-$C_7$cycloalkyl,
$R^2$ is a hydrogen atom,
$R^3$ is $C_1$-$C_6$ halogenoalkoxy,
Ring A is the formula (i),
$X^1$ is formula (iv), (v-a), or (vii-a), and
Z is CH,
or a pharmaceutically acceptable salt thereof.

15. A compound selected from the group consisting of
N-(4-cyclopropylisoquinolin-3-yl)-4-(5-oxo-4,5-dihydro-1H-tetrazol-1-yl)-N-[4-(trifluoromethoxy)benzyl]benzenesulfonamide;
N-(4-cyclopropylisoquinolin-3-yl)-6-(5-oxo-4,5-dihydro-1,2,4-oxadiazol-3-yl)-N-[4-(trifluoromethoxy)benzyl]pyridine-3-sulfonamide;
N-(4-(trifluoromethyl)isoquinolin-3-yl)-6-(1H-1,2,4-triazol-5-yl)-N-[4-(trifluoromethoxy)benzyl]pyridine-3-sulfonamide;
N-(4-(trifluoromethyl)isoquinolin-3-yl)-6-(3-methyl-1H-1,2,4-triazol-5-yl)-N-[4-(trifluoromethoxy)benzyl]pyridine-3-sulfonamide;
4-({(4-cyclopropylisoquinolin-3-yl)[4-(trifluoromethoxy)benzyl]amino}sulfonyl)-2-methylbenzoic acid; and
4-({(4-cyclopropylisoquinolin-3-yl[4-(trifluoromethoxy)benzyl]amino}sulfonyl)-2-(dimethylamino)benzoic acid,
or a pharmaceutically acceptable salt thereof.

16. A pharmaceutical composition comprising the compound according to claim 1 or a pharmaceutically acceptable salt thereof as an active ingredient.

17. A method for treating a TRPM8-involving disease selected from the group consisting of chronic pain, cephalalgia, urologic disease, carcinoma, respiratory disease, gastrointestinal disease, psychiatric disease, neurological disease and dermatosis by administering to a patient in need thereof the compound of any one of claims 1-4.

* * * * *